(12) United States Patent
Shia et al.

(10) Patent No.: US 8,962,845 B2
(45) Date of Patent: Feb. 24, 2015

(54) PYRAZOLE COMPOUNDS

(71) Applicant: National Health Research Institutes, Miaoli County (TW)

(72) Inventors: Kak-Shan Shia, Taipei (TW); Chun-Ping Chang, Taichung (TW); Yu-Sheng Chao, New York, NY (US)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 13/626,035

(22) Filed: Sep. 25, 2012

(65) Prior Publication Data

US 2013/0085126 A1  Apr. 4, 2013

Related U.S. Application Data

(60) Provisional application No. 61/541,182, filed on Sep. 30, 2011.

(51) Int. Cl.

| | | |
|---|---|---|
| *C07D 417/14* | (2006.01) | |
| *C07D 409/14* | (2006.01) | |
| *C07D 413/14* | (2006.01) | |
| *C07D 487/08* | (2006.01) | |
| *C07D 401/14* | (2006.01) | |
| *A61K 31/4427* | (2006.01) | |
| *C07D 403/12* | (2006.01) | |
| *C07D 231/14* | (2006.01) | |
| *C07D 409/04* | (2006.01) | |
| *C07D 413/12* | (2006.01) | |
| *C07D 471/08* | (2006.01) | |

(52) U.S. Cl.
CPC ............ *C07D 487/08* (2013.01); *C07D 409/14* (2013.01); *C07D 413/14* (2013.01); *C07D 417/14* (2013.01); *C07D 401/14* (2013.01); *C07D 403/12* (2013.01); *C07D 231/14* (2013.01); *C07D 409/04* (2013.01); *C07D 413/12* (2013.01); *C07D 471/08* (2013.01)
USPC ........ 546/184; 546/187; 546/211; 546/374.1; 514/210.2; 514/236.5; 514/316; 514/253.09; 514/227.8

(58) Field of Classification Search
USPC .............................. 546/184, 374.1; 514/210.2
See application file for complete search history.

(56) References Cited

U.S. PATENT DOCUMENTS

| | | | |
|---|---|---|---|
| 6,028,084 | A | 2/2000 | Barth et al. |
| 7,485,730 | B2 * | 2/2009 | Lazzari et al. ............. 548/359.5 |
| 2004/0192667 | A1 | 9/2004 | Makriyannis et al. |
| 2007/0149512 | A1 * | 6/2007 | Antel et al. ................. 514/227.5 |
| 2008/0200527 | A1 | 8/2008 | Amengual et al. |

FOREIGN PATENT DOCUMENTS

| | | | |
|---|---|---|---|
| CN | 1827603 | A | 9/2006 |
| CN | 101087763 | A | 12/2007 |
| CN | 101535260 | A | 9/2009 |
| CN | 101795569 | A | 8/2010 |
| EP | 1571147 | A | 7/2005 |
| JP | 2000500479 | A | 1/2000 |
| JP | 2005503428 | A | 2/2005 |
| JP | 2005255685 | A | 9/2005 |
| JP | 2008525404 | A | 7/2008 |
| JP | 2008526887 | A | 7/2008 |
| JP | 2009529540 | A | 8/2009 |
| JP | 2010-070514 | | 4/2010 |
| JP | 2010539088 | A | 12/2010 |
| WO | WO 03/020217 | | 3/2003 |
| WO | 03026648 | A | 4/2003 |
| WO | WO 2006/067443 | | 6/2006 |
| WO | 2006074445 | A | 7/2006 |
| WO | 2007106721 | A | 9/2007 |
| WO | WO 2008/057681 | A2 | 5/2008 |
| WO | 2008074982 | A | 6/2008 |
| WO | WO 2009/029727 | | 3/2009 |
| WO | WO 2009/033125 | | 3/2009 |
| WO | WO 2009/074782 | * | 6/2009 |

OTHER PUBLICATIONS

Ming-Shiu Hung, Chun-Ping Chang, Ting-Chieh Li, Teng-Kuang Yeh, Jen-Shin Song, Yinchiu Lin, Chien- Huang Wu, Po-Chu Kuo, Prashanth K. Amancha, Ying-Chieh Wong, Wen-Chi Hsiao, Yu-Sheng Chao, and Kak-Shan Shia; ChemMedChem 2010, 5, 1439-1443.*
Wermuth, Camille Georges (2008). Practice of Medicinal Chemistry (3rd Edition). Elsevier Chapters 18 and 20.*
Wermuth; Practice of Medicinal Chemistry, Third Ed, 2008, chapters 14 and 18.*
Seo; Bioorganic & Medicinal Chemistry 18 (2010) 1149-1162.*
Pertwee; Phil. Trans. R. Soc. B, 2012, 367, 3353-3363.*

(Continued)

*Primary Examiner* — John Mabry
*Assistant Examiner* — Daniel Carcanague
(74) *Attorney, Agent, or Firm* — Cesari and McKenna, LLP

(57) ABSTRACT

Compounds of formula (I):

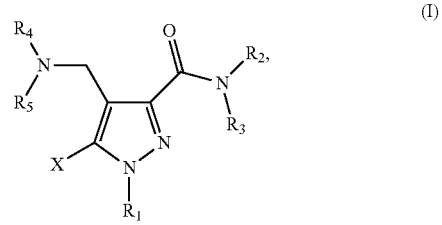

wherein $R_1$, $R_2$, $R_3$, $R_4$, $R_5$, and X are defined herein. Also disclosed are pharmaceutical compositions and methods related to use of these compounds.

11 Claims, No Drawings

(56) References Cited

OTHER PUBLICATIONS

Jinhwa Lee, Hee Jeong Seo, Suk Ho Lee, Jeongmin Kim, Myung Eun Jung, Sung-Han Lee, Kwang-Seop Song, Junwon Lee, Suk Youn Kang, Min Ju Kim, Mi-Soon Kim, Eun-Jung Son, Minwoo Lee, Ho-Kyun Han, Discovery of 2-(4-((1H-1,2,4-triazol-1-yl)methyl)-5-(4-bromophenyl)-1-(2-chlorophenyl)-1H-pyrazol-3-yl)-5-tert-butyl-1,3,4-thiadiazole (GCC2680) as a potent, selective and orally efficacious cannabinoid-1 receptor antagonist, Bioorganic & Medicinal Chemistry 18 (2010) 6377-6388.

Suk Ho Lee, Hee Jeong Seo, Sung-Han Lee, Myung Eun Jung, Ji-Hyun Park, Hyun-Ju Park, Jakyung Yoo, Hoseop Yun, Jooran Na, Suk Youn Kang, Kwang-Seop Song, Min-Ah Kim, Chong-Hwan Chang, Jeongmin Kim, and Jinhwa Lee, Biarylpyrazolyl Oxadiazole as Potent, Selective, Orally Bioavailable Cannabinoid-1 Receptor Antagonists for the Treatment of Obesity, J. Med. Chem. 2008, 51, 7216-7233.

* cited by examiner

PYRAZOLE COMPOUNDS

CROSS REFERENCE TO RELATED APPLICATIONS

This application claims priority to U.S. Provisional Application No. 61/541,182, filed Sep. 30, 2011, the content of which is incorporated herein by reference in its entirety.

BACKGROUND

Central cannabinoid 1 (CB1) receptors are expressed in the brain. Their functions affect many neurological and psychological events. See, e.g., Goutopoulos et al., Pharmacol. Ther., 2002, 95, 103-7; and Shia et al., U.S. Pat. No. 7,834,046. Rimonabant, a central CB1 receptor antagonist, has been used to treat obesity. However, this drug has adverse psychiatric side effects. See e.g., Wu et al., Curr. Top. Med. Chem., 2011, 11, 1421-29.

CB1 receptors are also expressed in several peripheral tissues, e.g., liver, fat tissues, adipose tissues, and adrenal glands. See Marzo et al., Nat. Rev. Endocrinol., 2009, 5, 633-638. Peripheral CB1 receptor antagonists are potential drugs for treating many disorders, such as obesity, overweight, non-alcoholic fatty liver diseases, type 2 diabetes, nephropathy, kidney fibrosis, osteoporosis, and osteoarthritis. See e.g., Bioorg. Med. Chem. Lett. 2009, 19, 639-643; J. Clin. Invest. 2010, 120, 2953-2966; Bioorg. Med. Chem. Lett. 2010, 20, 4573-4577; and Diabetes 2010, 59, 1046-1054. It is widely accepted that such drugs should not have undesirable side effects as observed with rimonabant. See e.g., Wu et al., Curr. Top. Med. Chem., 2011, 11, 1421-29.

Safe and efficacious drug candidates remain to be identified from peripheral CB1 receptor antagonists, both synthesized and not yet synthesized.

SUMMARY

This invention is based on the discovery that certain pyrazole compounds are effective in treating peripheral CB1 receptor mediated disorders.

In one aspect, this invention features pyrazole compounds of formula (I):

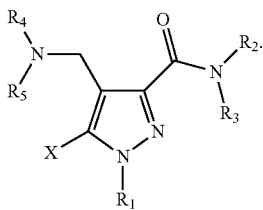

(I)

In this formula, $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; each of $R_2$ and $R_3$, independently, is H, $C_1$-$C_{10}$ alkyl, $C_3$-$C_{20}$ cycloalkyl, $C_3$-$C_{20}$ heterocycloalkyl, aryl, or heteroaryl; or $R_2$, together with $R_3$ and the nitrogen atom to which they are attached, is $C_3$-$C_{20}$ heterocycloalkyl, $C_3$-$C_{20}$ heterocycloalkenyl, or heteroaryl; each of $R_4$ and $R_5$, independently, is H, $C_1$-$C_{10}$ alkyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl, $C(O)R_a$, $C(O)OR_a$, $C(O)NR_aR_b$, $C(S)NR_aR_b$, $C(=NH)NR_aR_b$, $C(=N-CN)NR_aR_b$, $C(=N-NO_2)$) $NR_aR_b$, $S(O)R_a$, $S(O_2)R_a$, $S(O)NR_aR_b$, or $S(O_2)NR_aR_b$; or $R_4$, together with $R_5$ and the nitrogen atom to which they are attached, is $C_3$-$C_{20}$ heterocycloalkyl, $C_3$-$C_{20}$ heterocycloalkenyl, or heteroaryl; in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl; or $R_a$, together with $R_b$ and the nitrogen atom to which they are attached, is $C_3$-$C_{20}$ heterocycloalkyl, $C_3$-$C_{20}$ heterocycloalkenyl, or heteroaryl; and X is

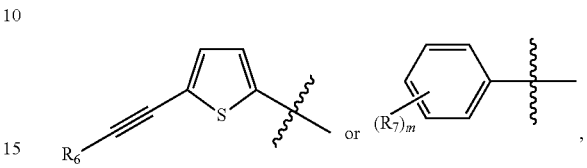

in which $R_6$ is H, $C_1$-$C_{10}$ alkyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl; $R_7$ is H, halo, trifluoromethyl, $C_1$-$C_{10}$ alkyl, $C_1$-$C_{10}$ alkoxy, nitro, cyano, amino, or hydroxyl; and m is 0, 1, 2, 3, 4, or 5.

One subset of the just-described compounds are pyrazole compounds, in which X is

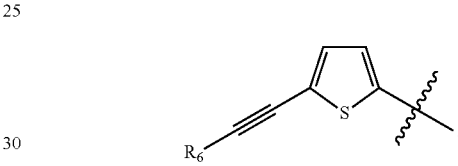

In these compounds, $R_1$ is aryl substituted with halo (e.g., 2,4-dichlorophenyl); each of $R_2$ and $R_3$, independently, is H or piperidinyl; each of $R_4$ and $R_5$, independently, is H or $S(O_2)NR_aR_b$, in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl; or $R_a$, together with $R_b$ and the nitrogen atom to which they are attached, is $C_3$-$C_{20}$ heterocycloalkyl, $C_3$-$C_{20}$ heterocycloalkenyl or heteroaryl; $R_6$ is $C_1$-$C_{10}$ alkyl, $C_3$-$C_{20}$ cycloalkyl, or aryl.

Another subset of the compounds described above are pyrazole compounds, in which X is

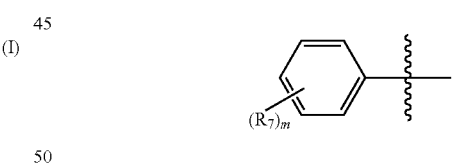

In these compounds, $R_1$ is aryl substituted with halo (e.g., 2,4-dichlorophenyl); each of $R_2$ and $R_3$, independently, is H or piperidinyl; each of $R_4$ and $R_5$, independently, is H or $S(O_2)NR_aR_b$, in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl; or $R_a$, together with $R_b$ and the nitrogen atom to which they are attached, is $C_3$-$C_{20}$ heterocycloalkyl, $C_3$-$C_{20}$ heterocycloalkenyl, or heteroaryl; $R_7$ is H, halo, or trifluoromethyl; and m is 1.

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—CH₃. The term "alkoxy" refers to an —O-alkyl. Examples of alkoxy include, but are not limited to, methoxy, ethoxy, n-propoxy, isopropoxy, n-butoxy, iso-butoxy, sec-butoxy, and tert-butoxy. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, alkoxy, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention features a method for treating a peripheral CB1 receptor mediated disorder. The method includes administering to a subject in need thereof an effective amount of one or more pyrazole compounds of formula (I) shown above. Examples of peripheral CB1 receptor mediated disorders include obesity, overweight, type 2 diabetes, a non-alcoholic fatty liver disease, hyperlipidemia, dyslipidemia, atherosclerosis, myocardial infarction, stroke, hypertension, bronchodilation, haemorrhagic shock, liver fibrosis, liver cirrhosis, neurological disorders, addictive disorders, metabolic disorders, glaucoma, osteoporosis, osteoarthritis, nephropathy, kidney fibrosis, and a chronic inflammatory disease.

The term "treating" or "treatment" refers to administering one or more pyrazole compounds to a subject, who has an above-described disorder, a symptom of such a disorder, or a predisposition toward such a disorder, with the purpose to confer a therapeutic effect, e.g., to cure, relieve, alter, affect, ameliorate, or prevent the above-described disorder, the symptom of it, or the predisposition toward it.

The pyrazole compounds described above include the compounds themselves, as well as their salts, prodrugs, and solvates, if applicable. A salt, for example, can be formed between an anion and a positively charged group (e.g., amino) on a pyrazole compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a pyrazole compound. Suitable cations include sodium ion, potassium ion, magnesium ion, calcium ion, and an ammonium cation such as tetramethylammonium ion. The pyrazole compounds also include those salts containing quaternary nitrogen atoms. Examples of prodrugs include esters and other pharmaceutically acceptable derivatives, which, upon administration to a subject, are capable of providing active pyrazole compounds. A solvate refers to a complex formed between an active pyrazole compound and a pharmaceutically acceptable solvent. Examples of pharmaceutically acceptable solvents include water, ethanol, isopropanol, ethyl acetate, acetic acid, and ethanolamine.

Also within the scope of this invention is a pharmaceutical composition containing one or more of the pyrazole compounds described above for use in treating one of the above-described disorders, and the use of such a composition for the manufacture of a medicament for this treatment.

The details of one or more embodiments of the invention are set forth in the description below. Other features, objects, and advantages of the invention will be apparent from the description and from the claims.

DETAILED DESCRIPTION

Shown below are exemplary compounds of this invention:

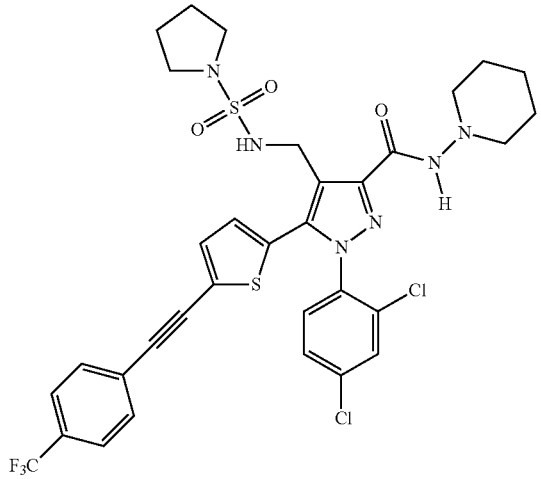

Compound 10

Compound 11
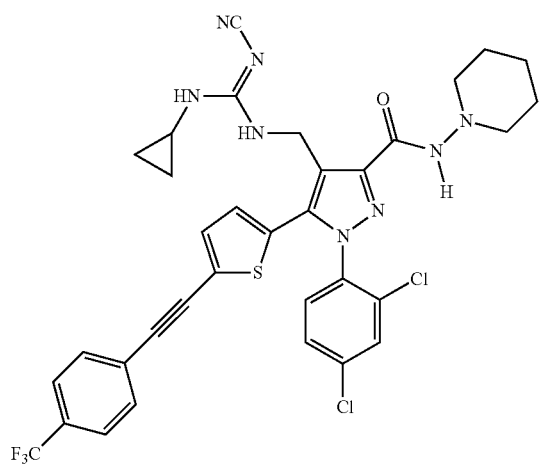
Compound 14
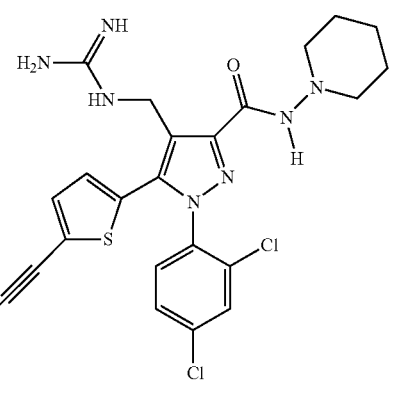
Compound 12
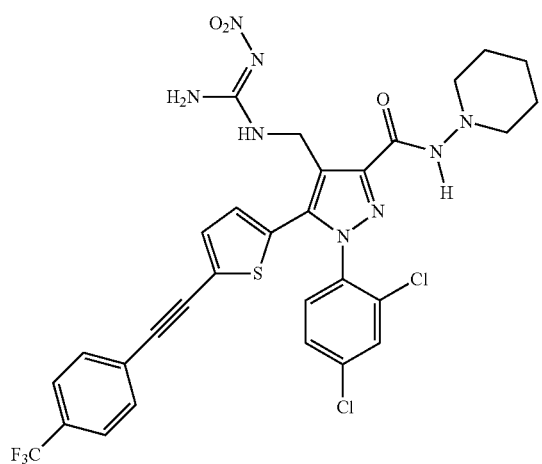
Compound 15
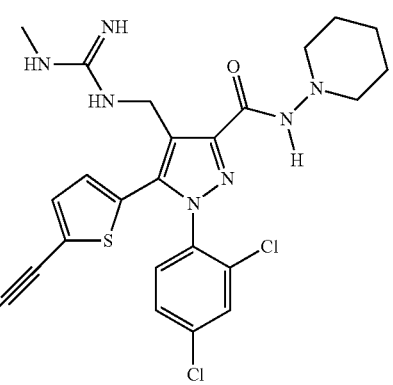
Compound 13
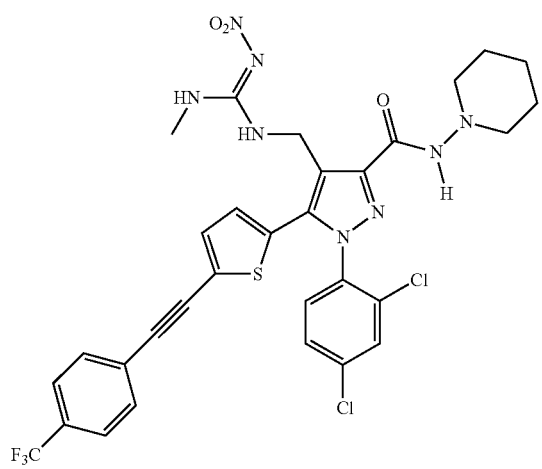
Compound 16
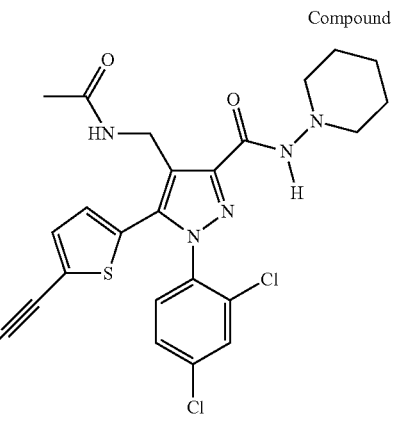

Compound 17
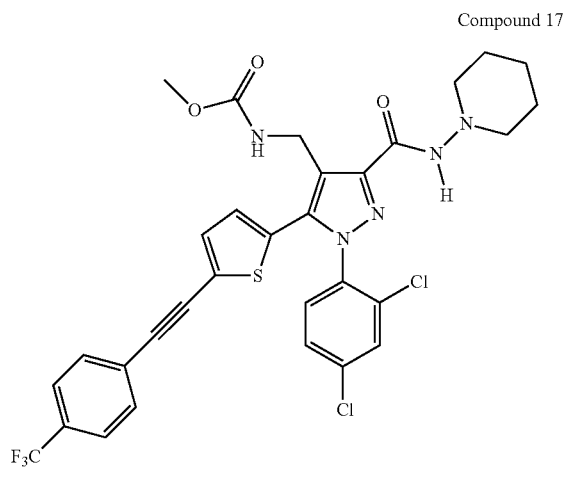
Compound 20
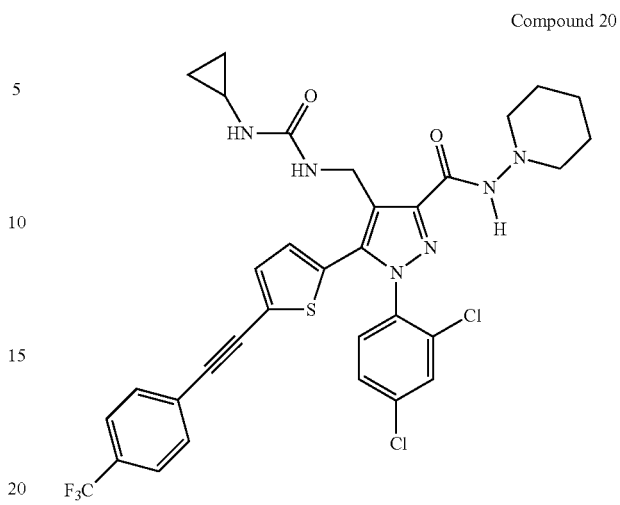
Compound 18
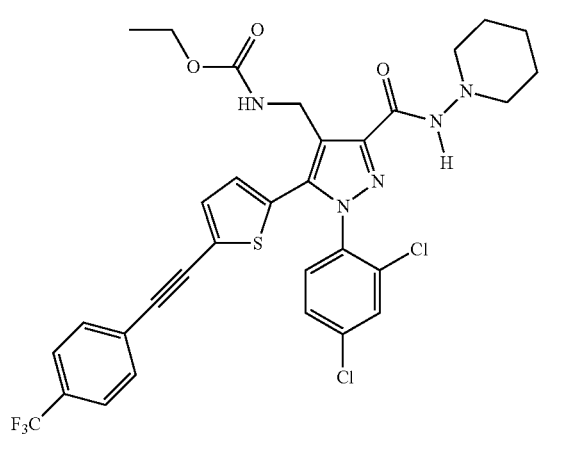
Compound 21
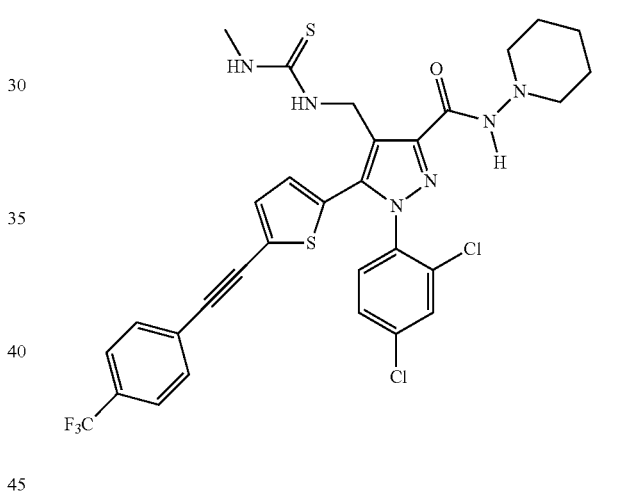
Compound 19
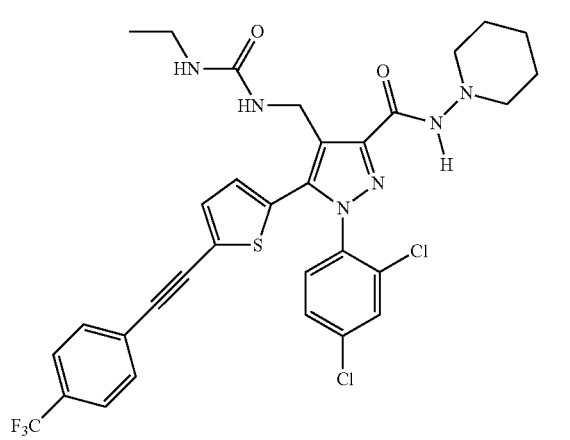
Compound 22
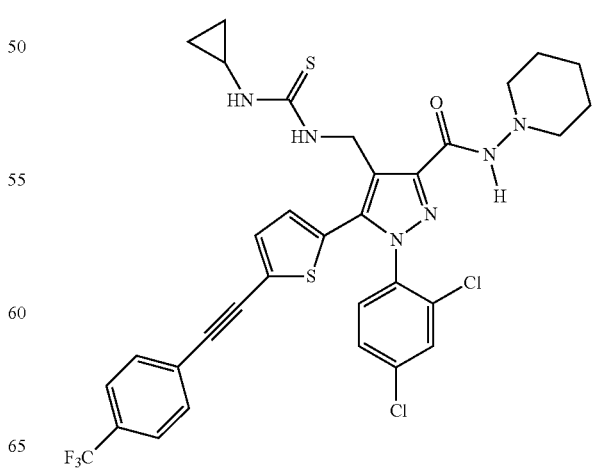

Compound 23
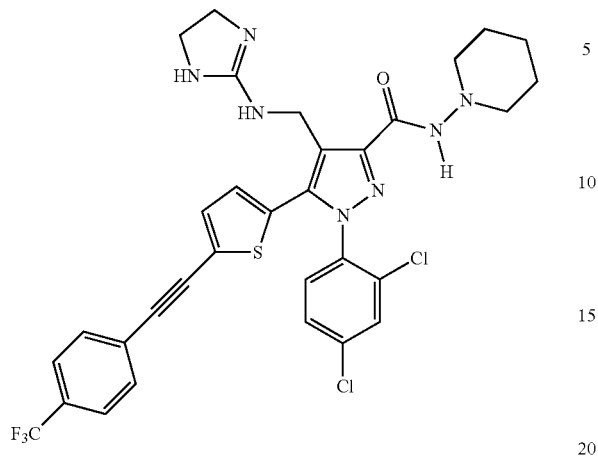
Compound 26
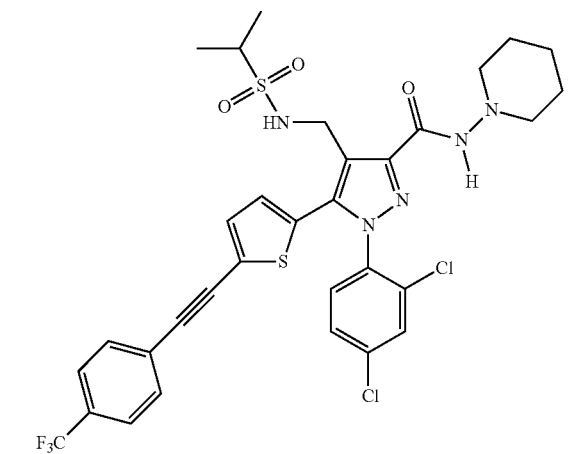
Compound 24
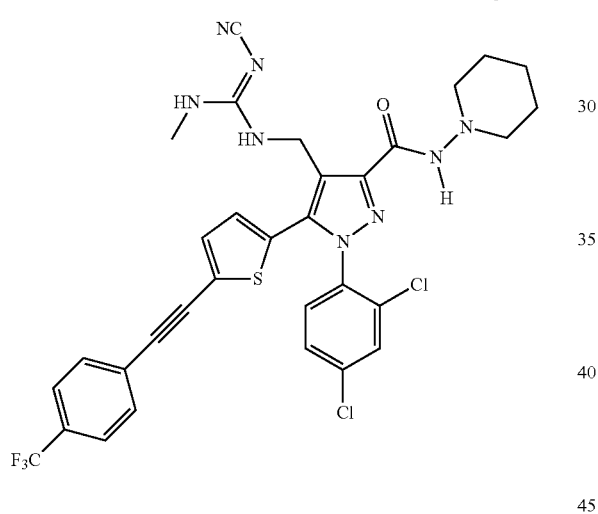
Compound 27
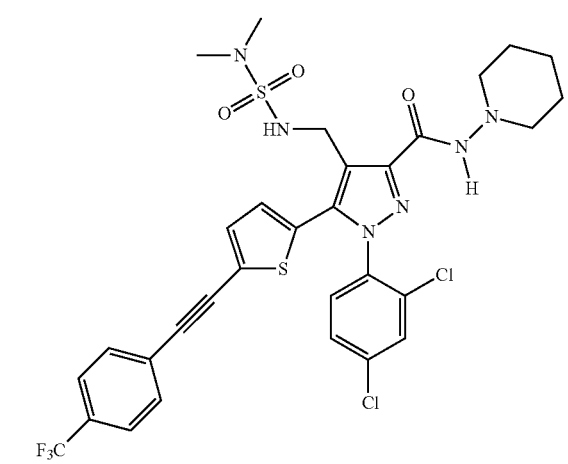
Compound 25
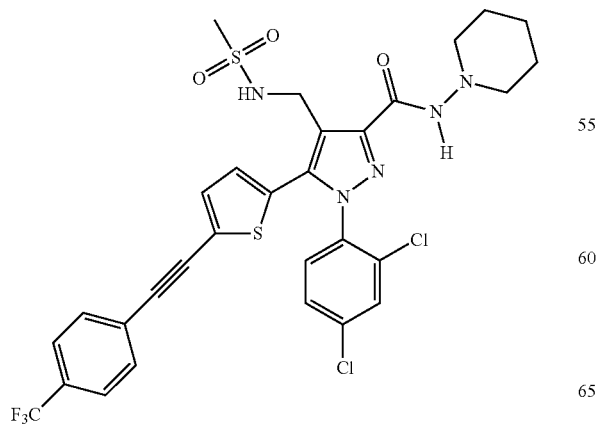
Compound 28
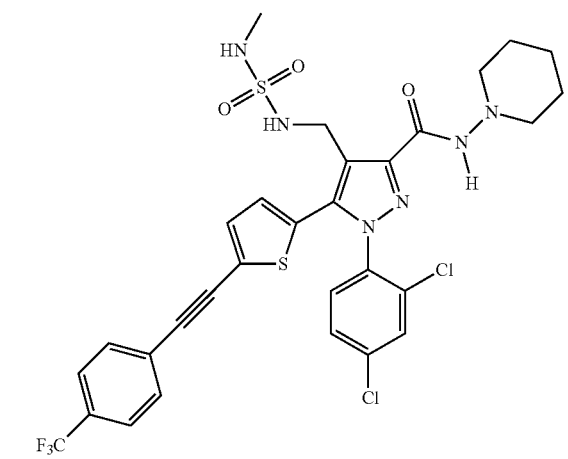

Compound 29
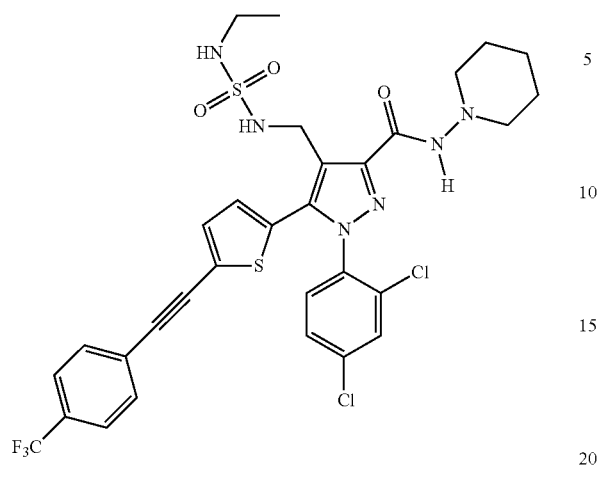
Compound 32
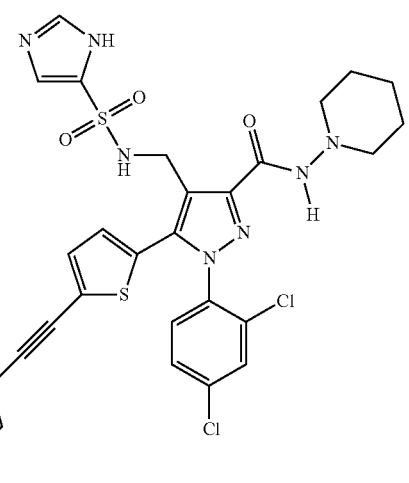
Compound 30
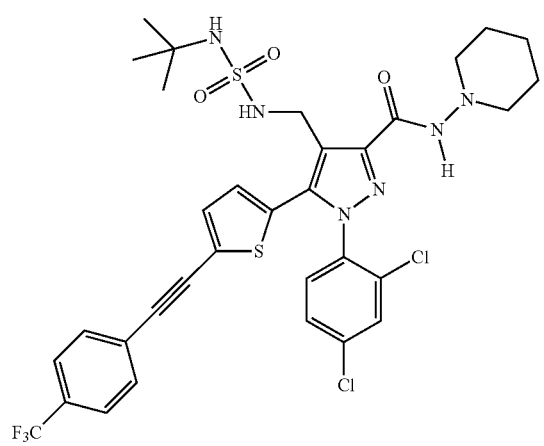
Compound 33
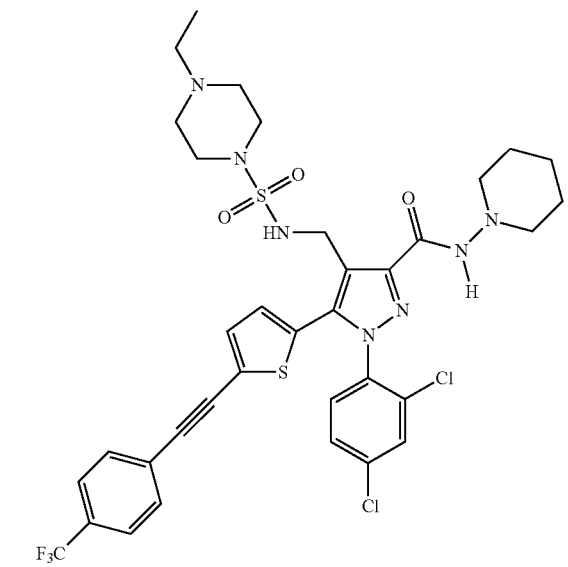
Compound 31
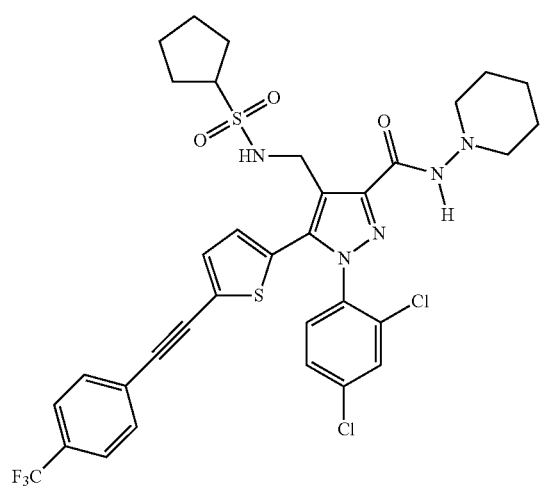
Compound 34

Compound 35
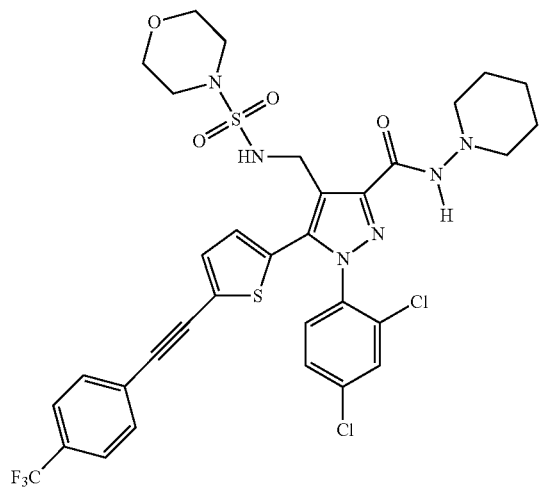
Compound 36
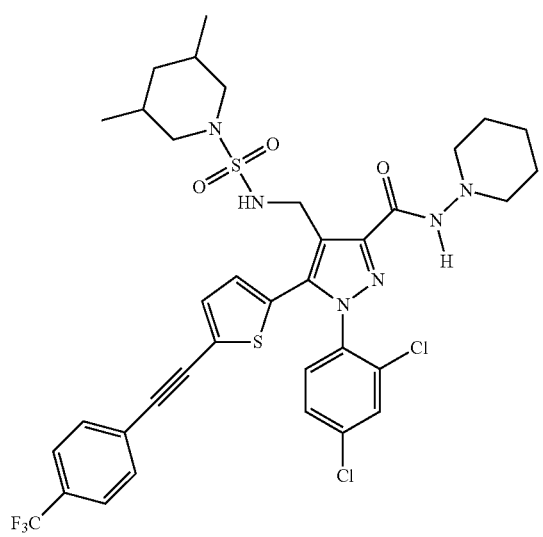
Compound 37
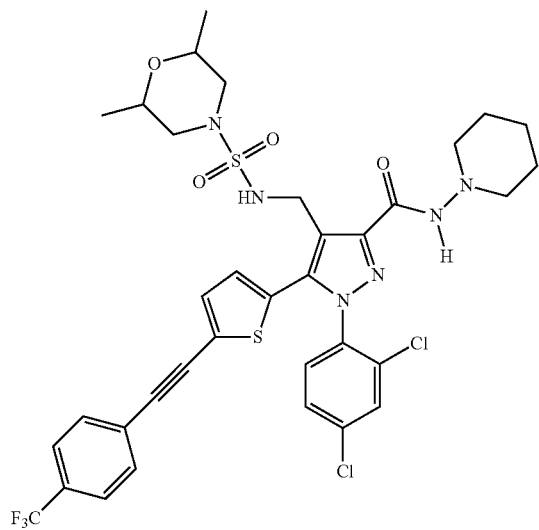
Compound 38
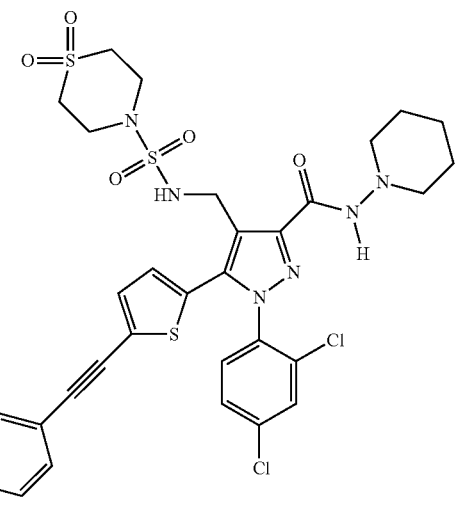
Compound 39
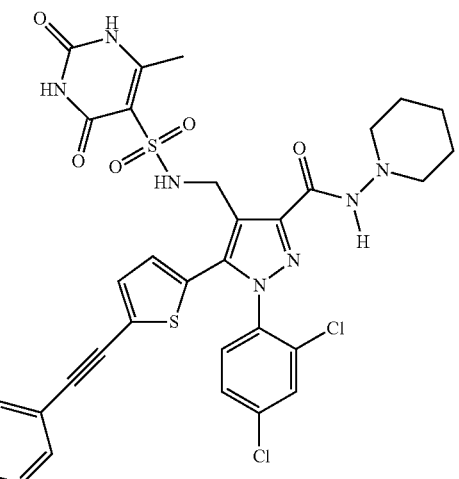
Compound 40
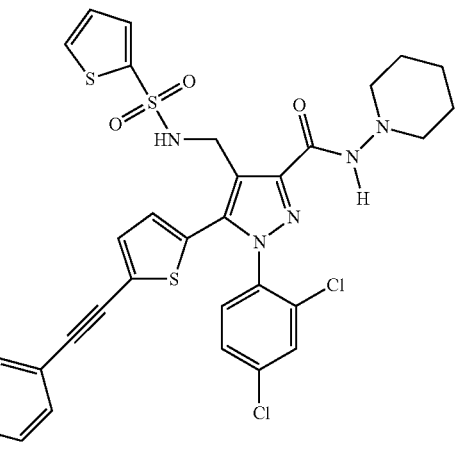

Compound 41
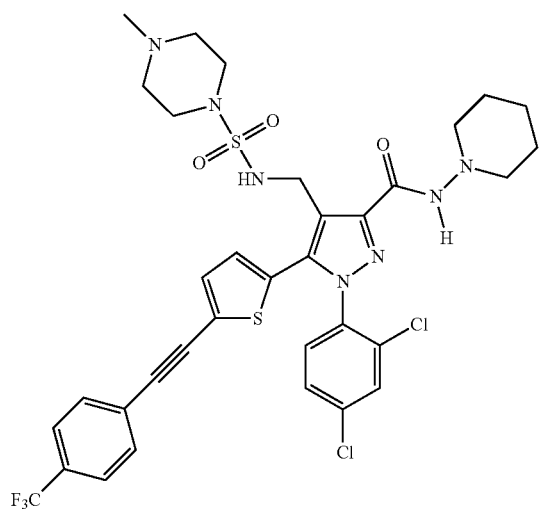
Compound 44
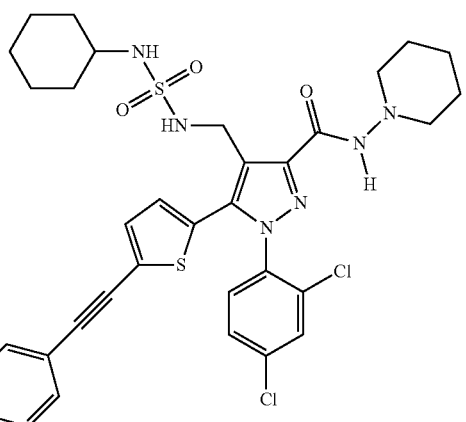
Compound 42
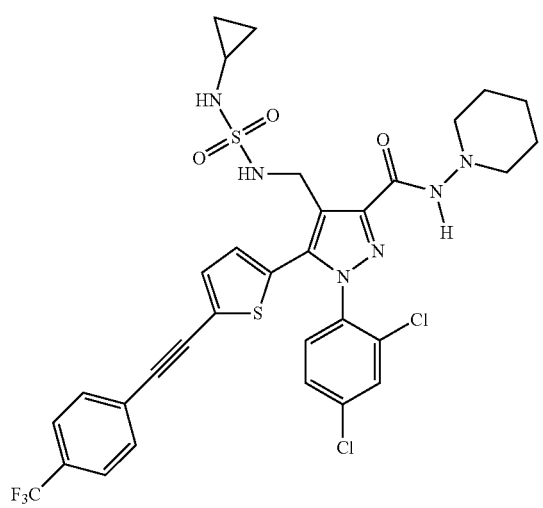
Compound 45
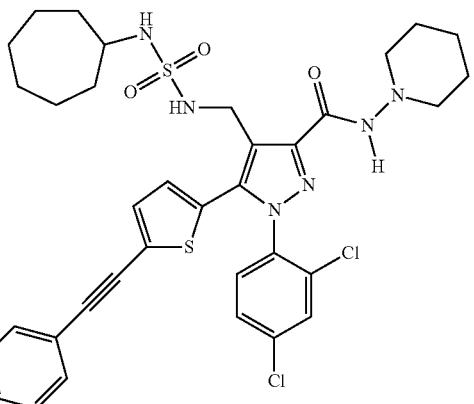
Compound 43
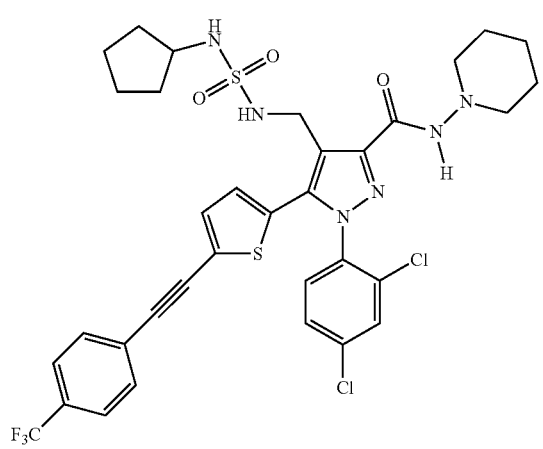
Compound 46
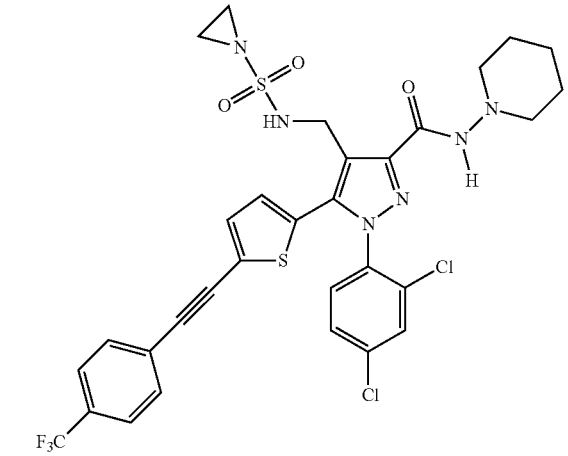

Compound 47
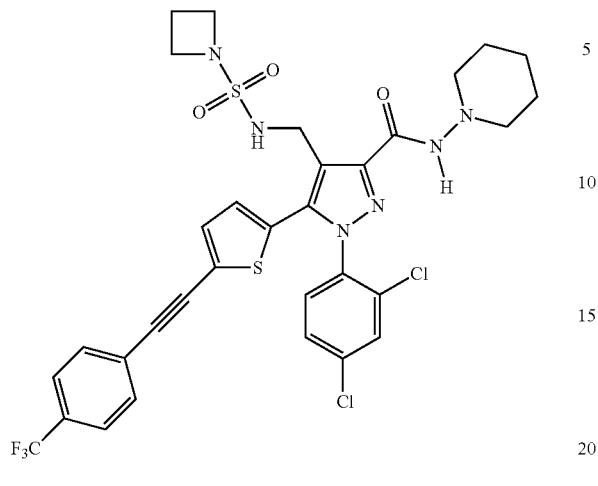
Compound 50
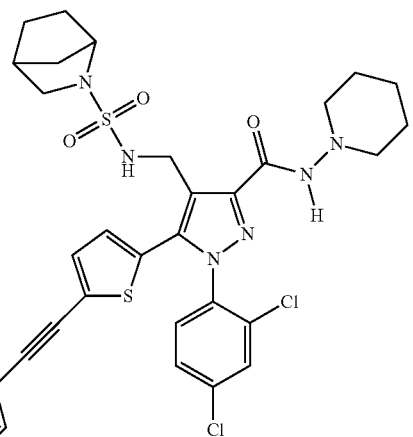
Compound 48
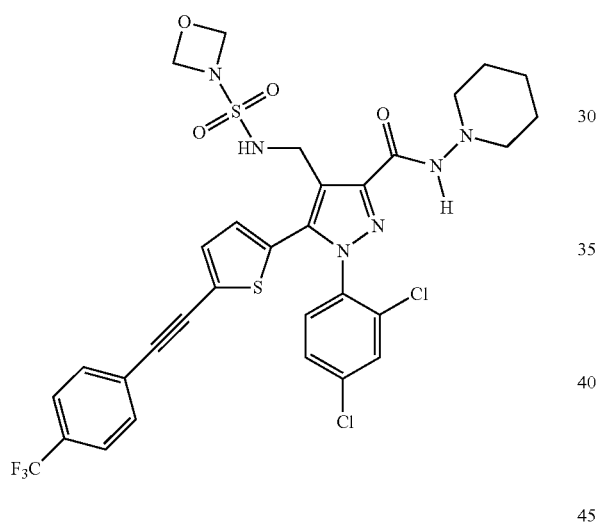
Compound 51
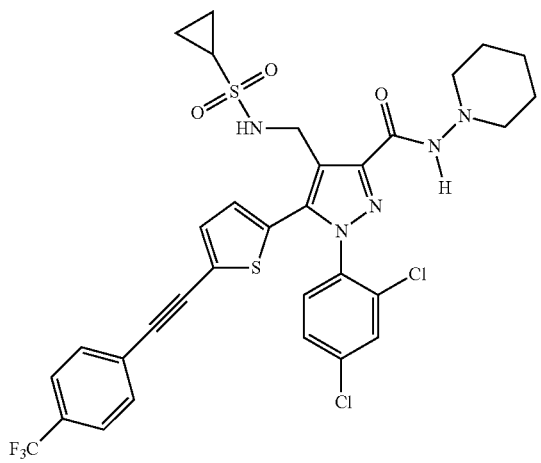
Compound 49
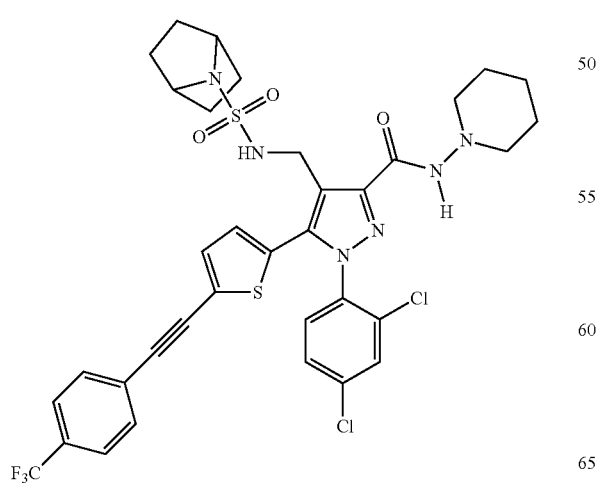
Compound 52
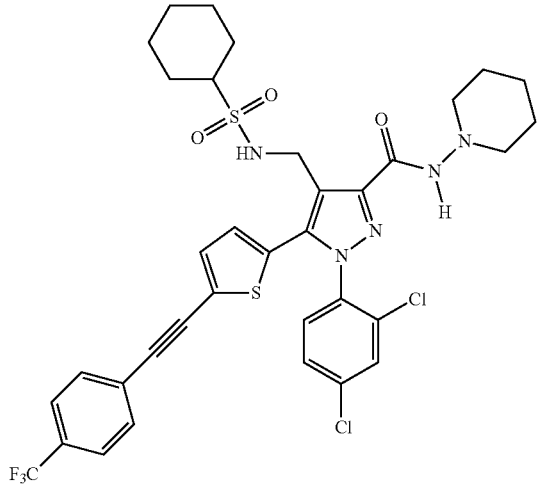

Compound 53
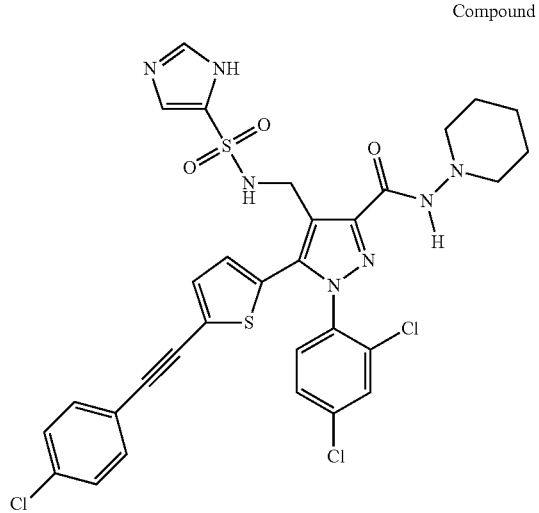
Compound 56
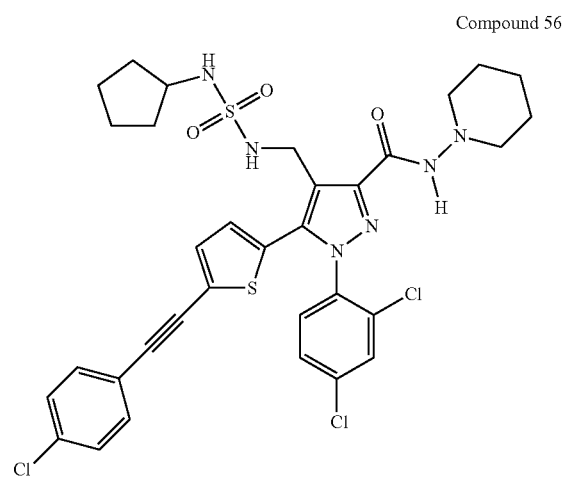
Compound 54
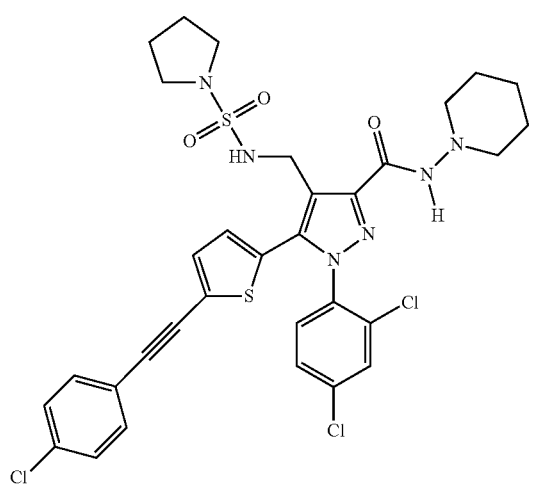
Compound 57
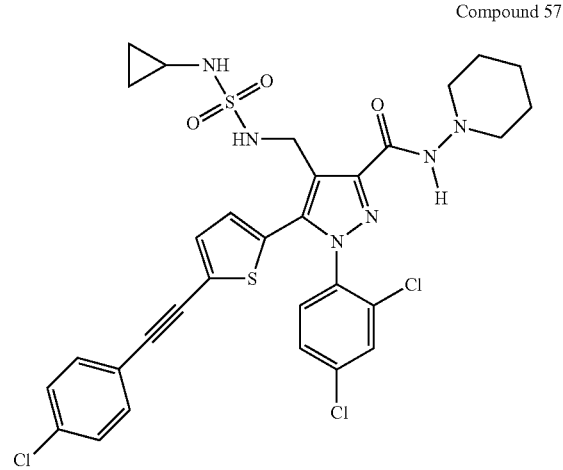
Compound 55
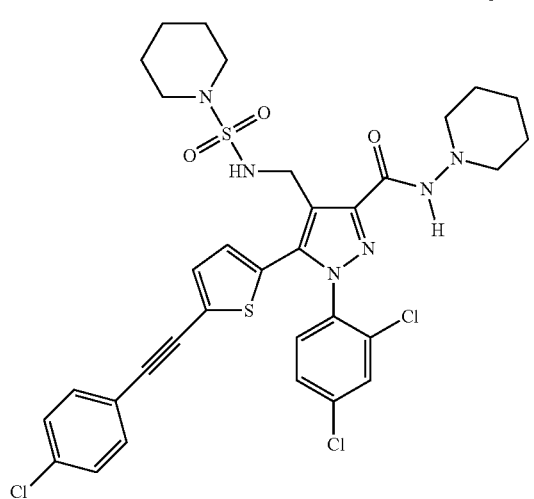
Compound 58
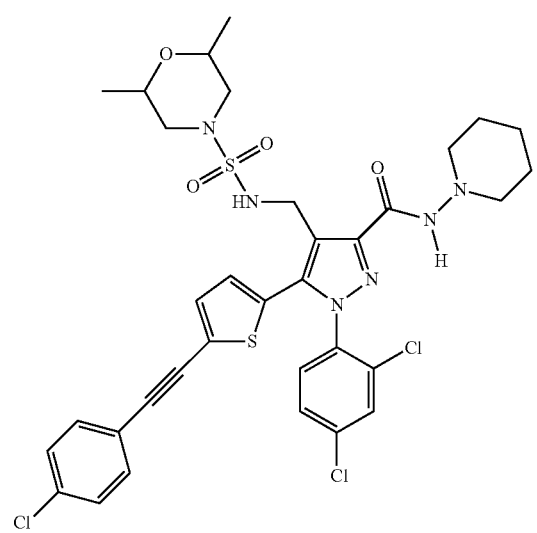

Compound 59
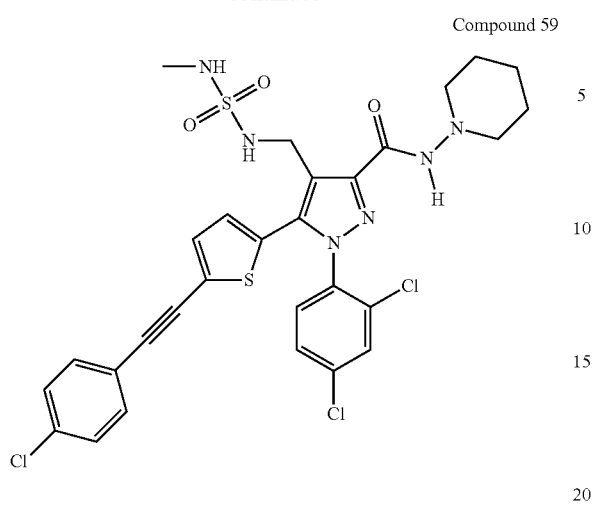
Compound 62
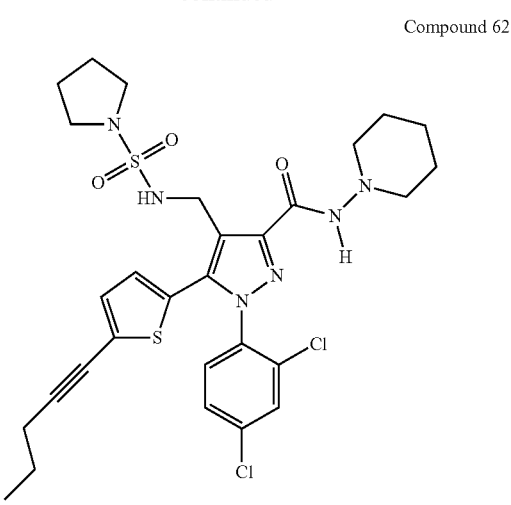
Compound 60
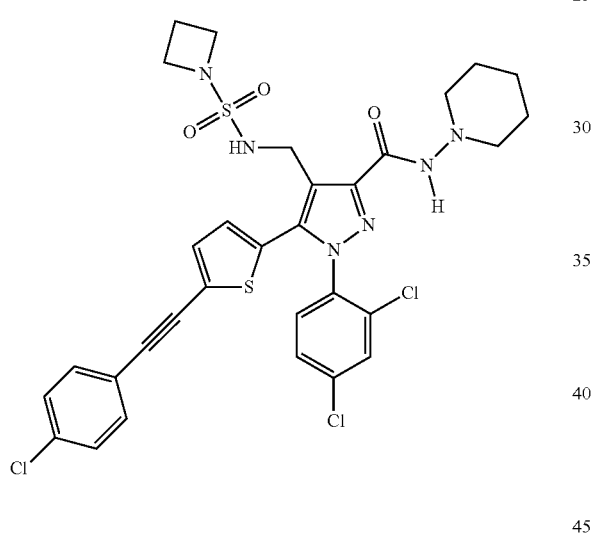
Compound 63
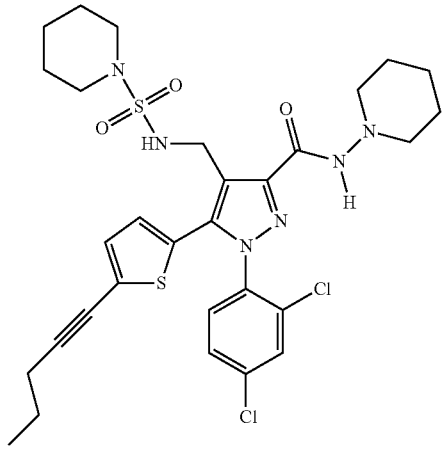
Compound 61
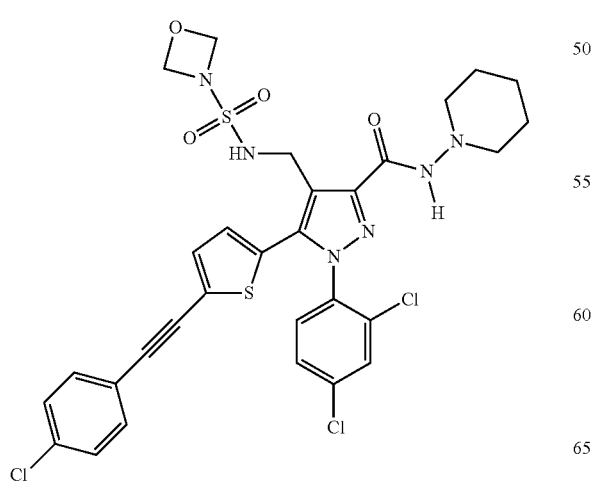
Compound 64
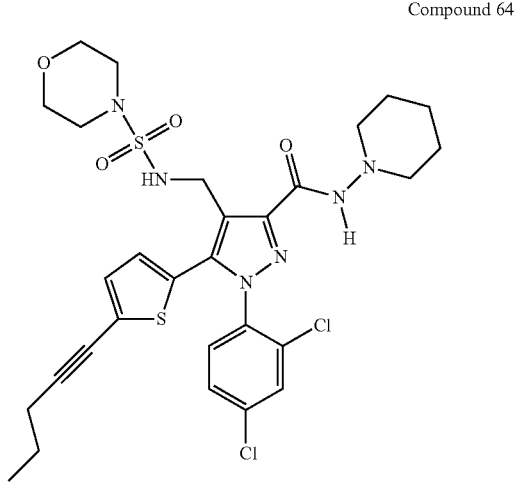

Compound 65
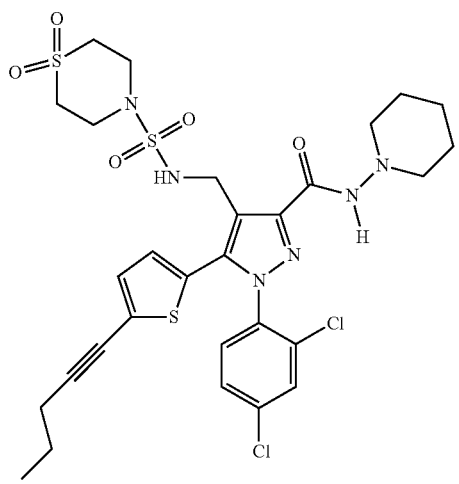
Compound 68
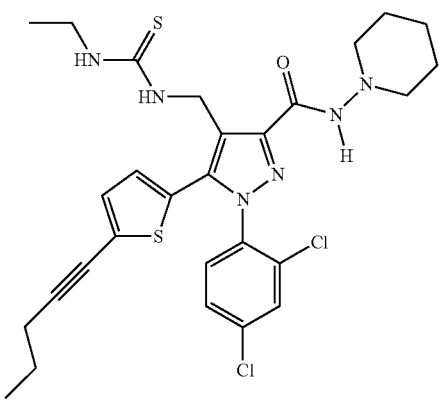
Compound 66
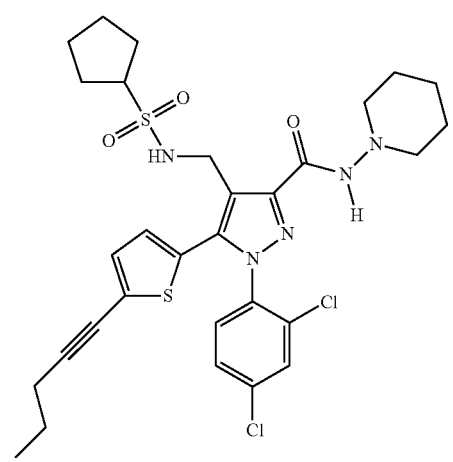
Compound 69
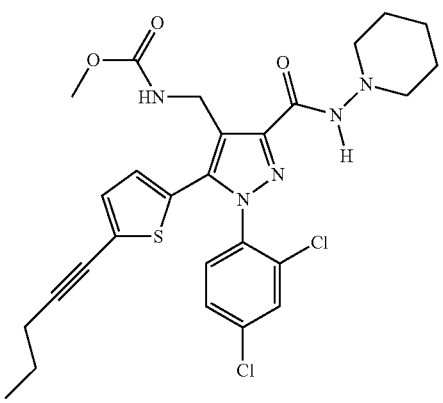
Compound 67
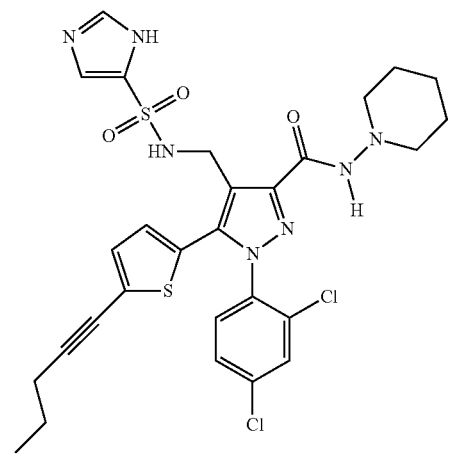
Compound 70
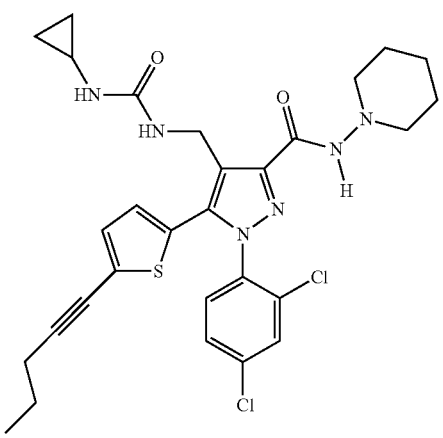

Compound 71
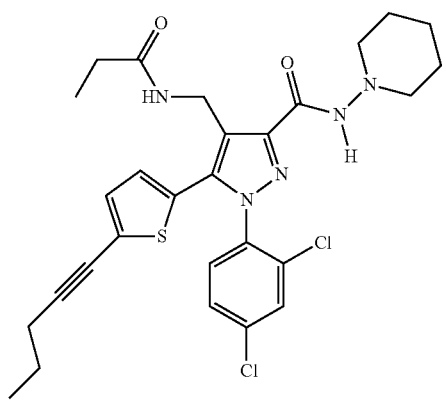
Compound 74
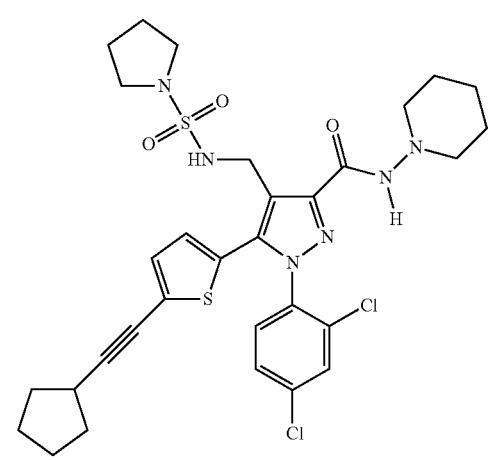
Compound 72
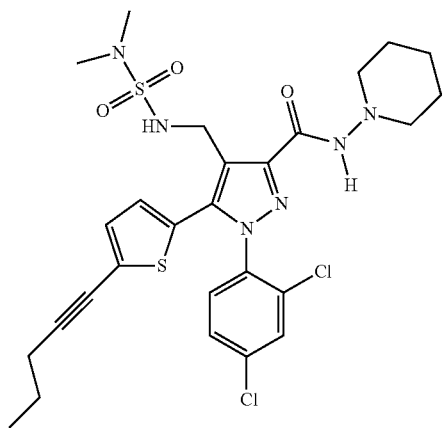
Compound 75
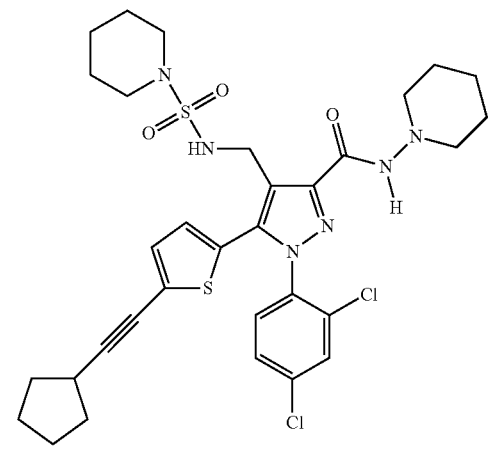
Compound 73
Compound 76
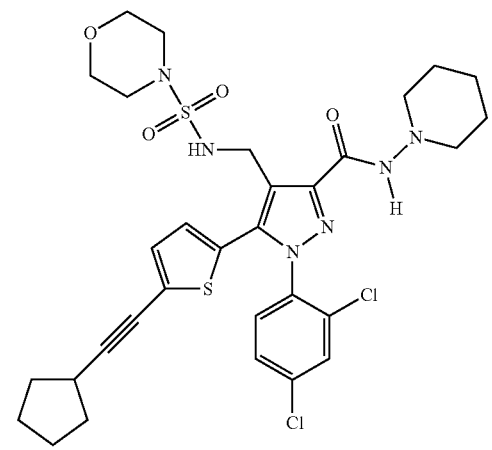

Compound 77
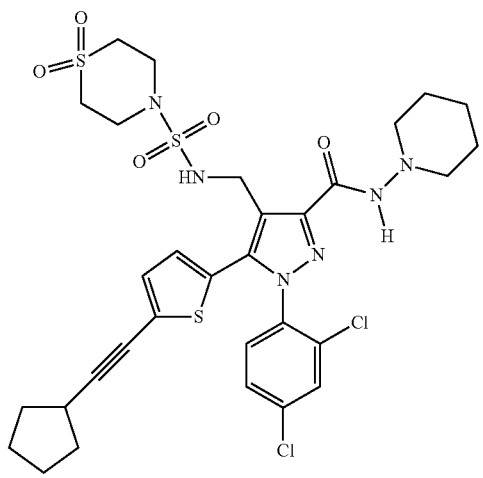
Compound 78
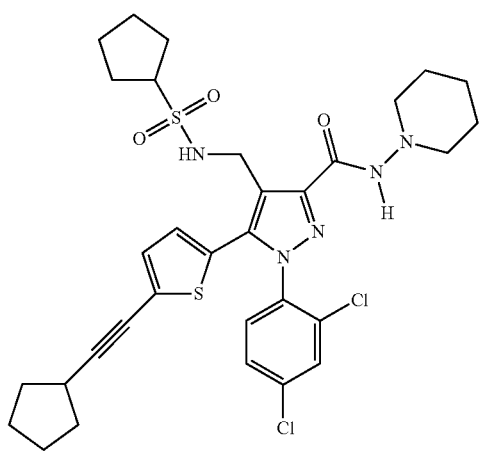
Compound 79
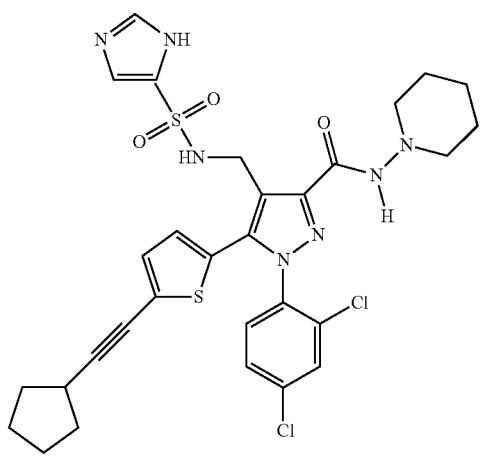
Compound 80
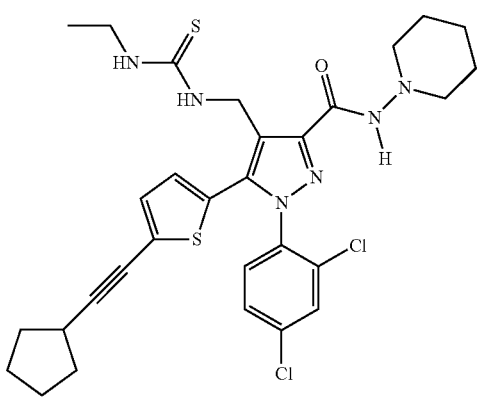
Compound 81
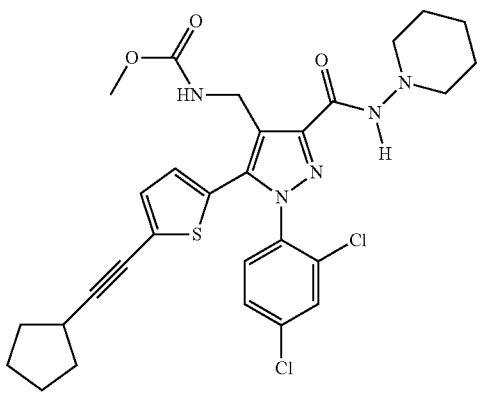
Compound 82
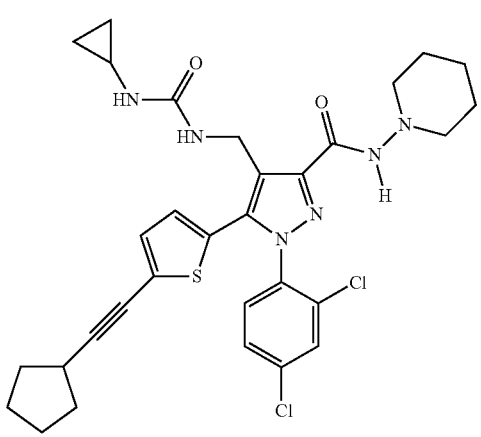

Compound 83
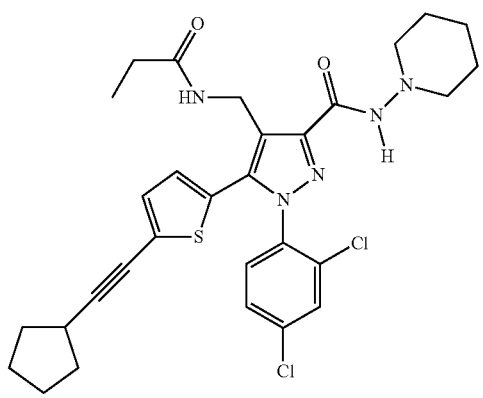
Compound 87
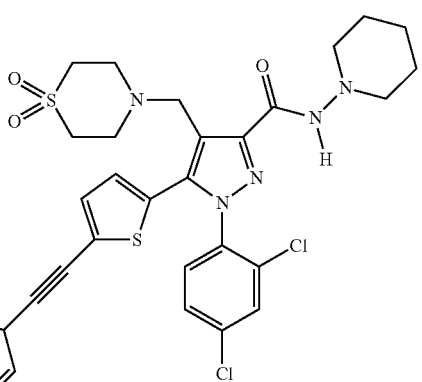
Compound 84
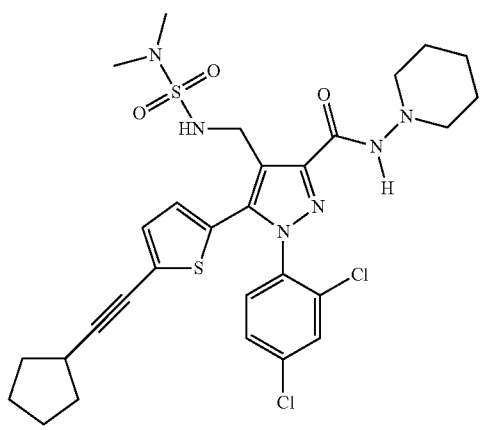
Compound 88
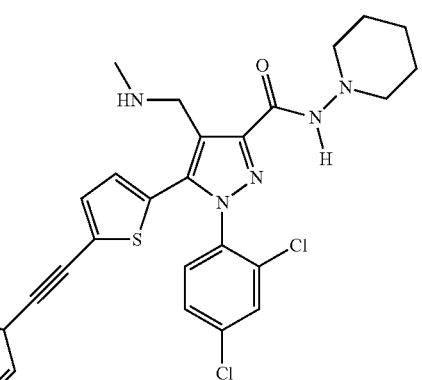
Compound 85
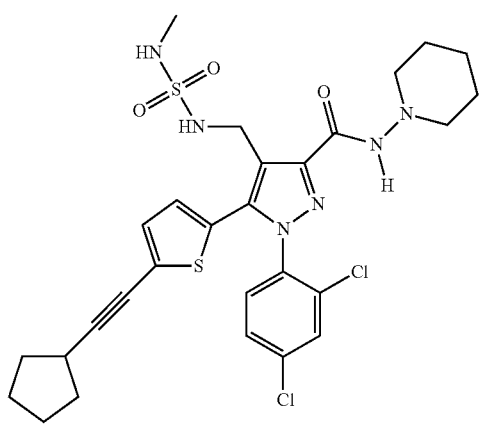
Compound 89
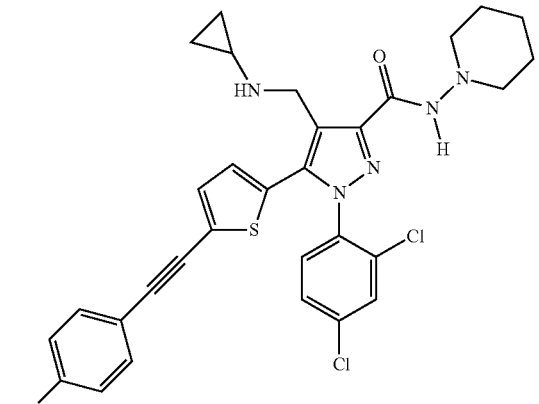

Compound 90
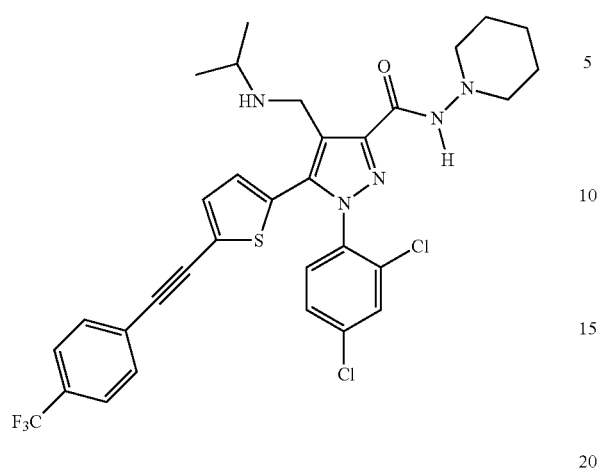
Compound 91
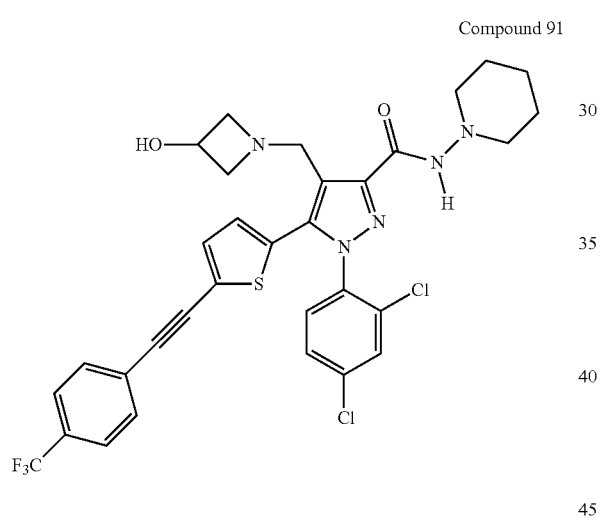
Compound 92
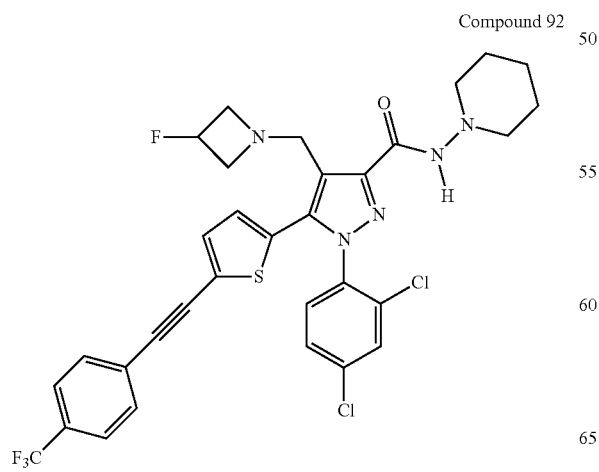
Compound 93
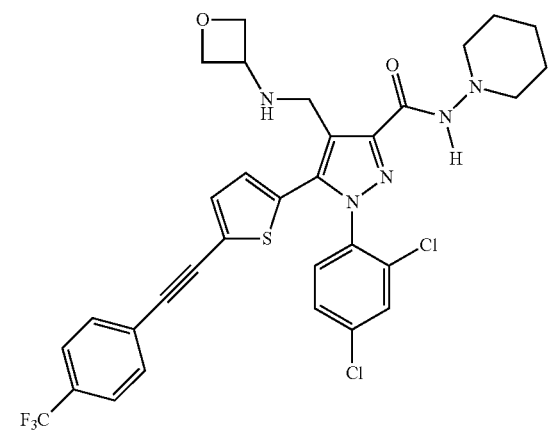
Compound 94
Compound 95
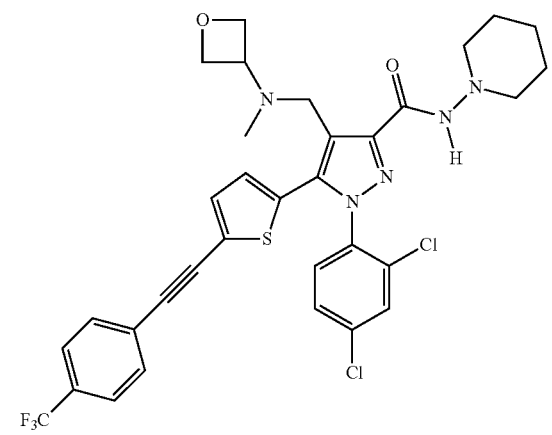

Compound 96
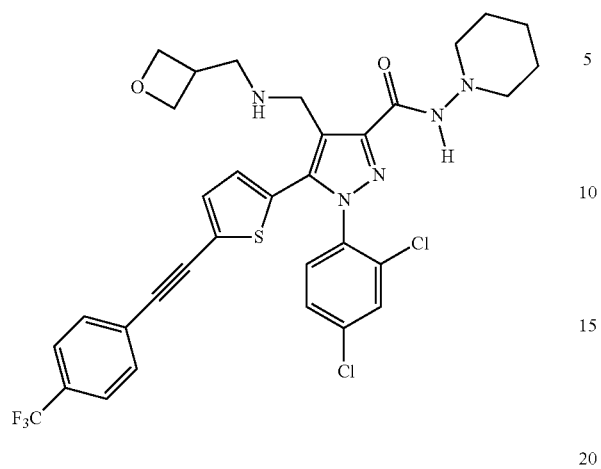
Compound 99
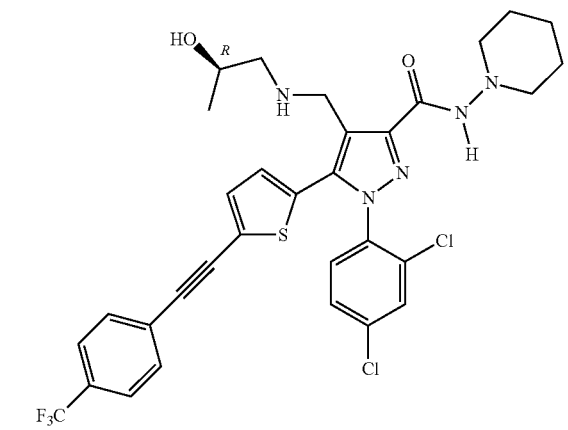
Compound 97
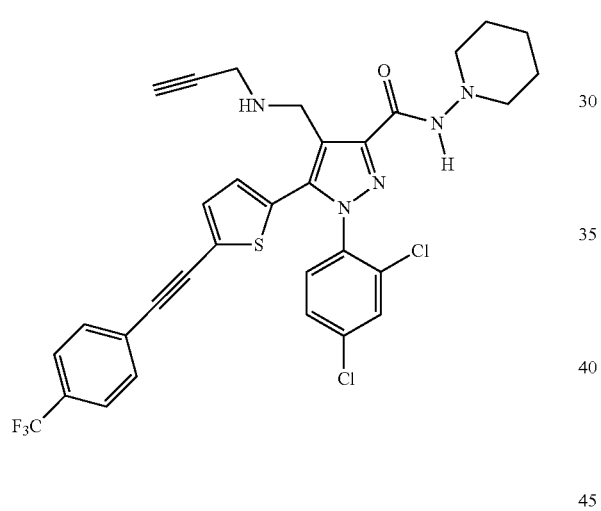
Compound 100
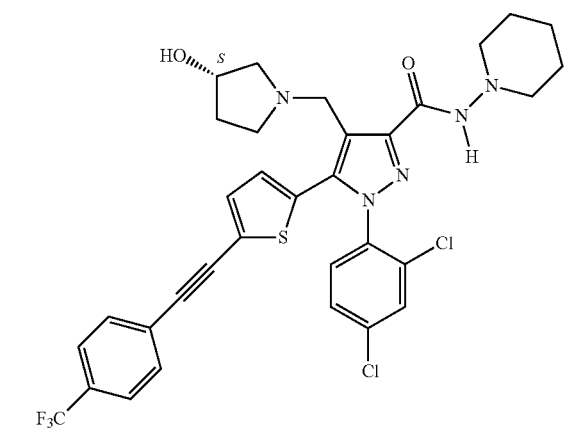
Compound 98
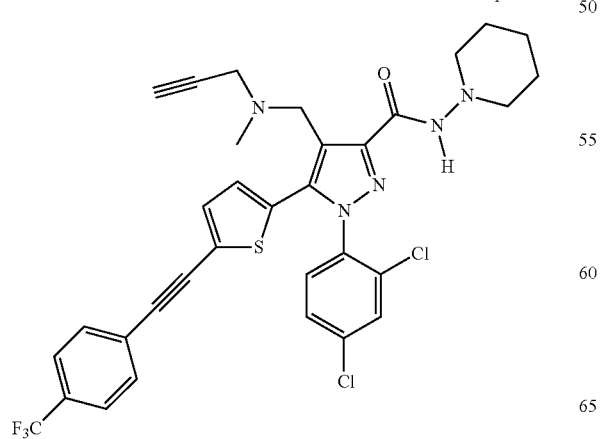
Compound 101
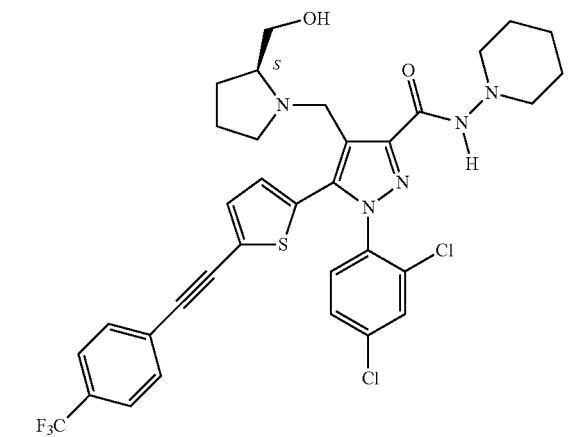

Compound 102
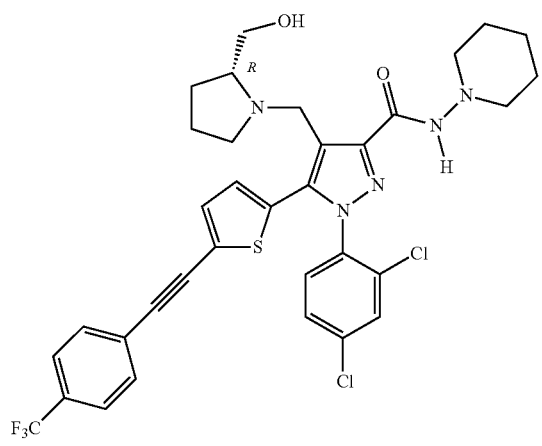
Compound 105
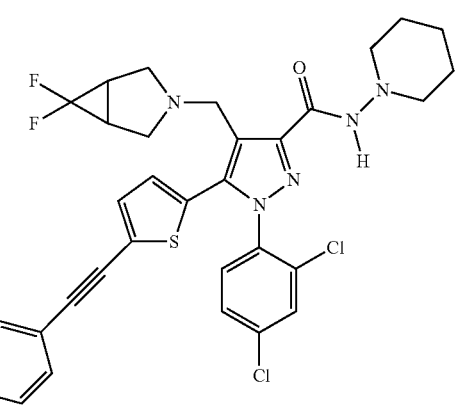
Compound 103
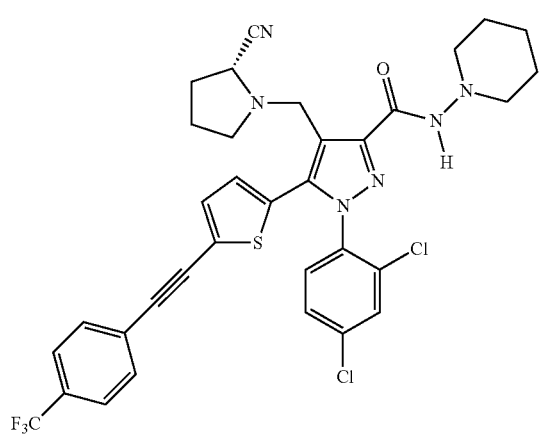
Compound 106
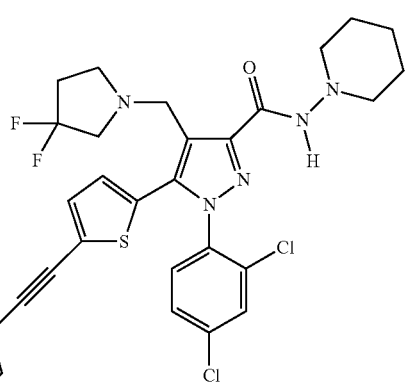
Compound 104
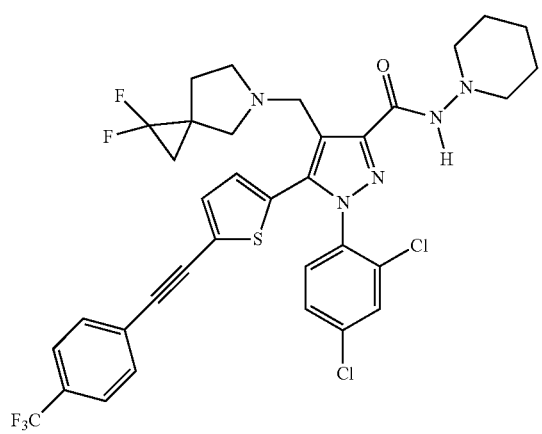
Compound 107
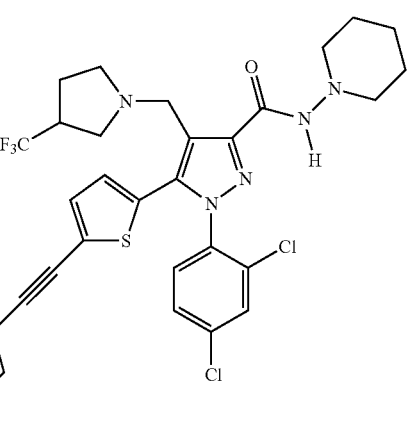

Compound 108
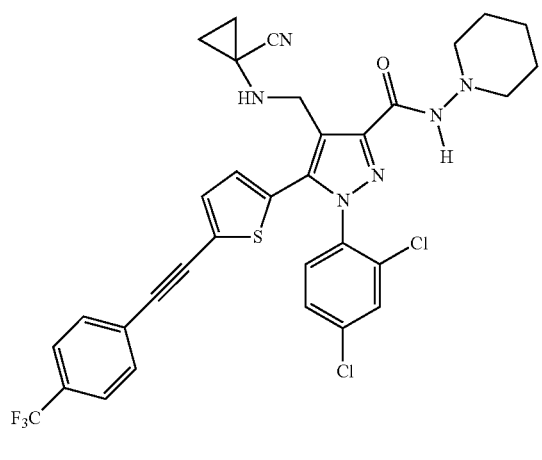
Compound 109
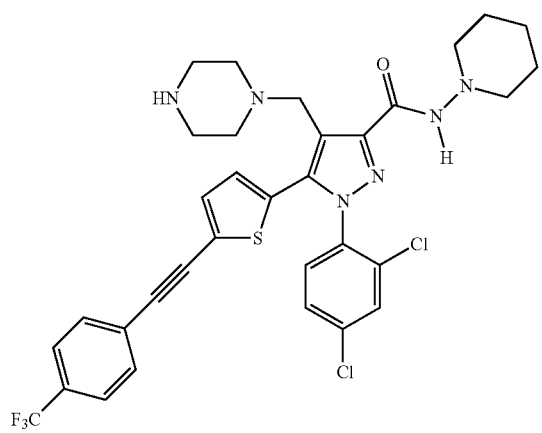
Compound 110
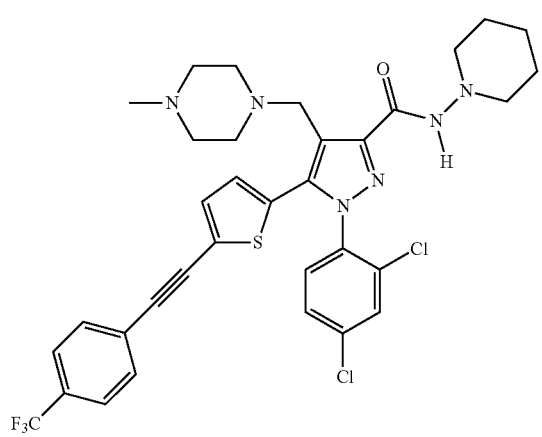
Compound 111
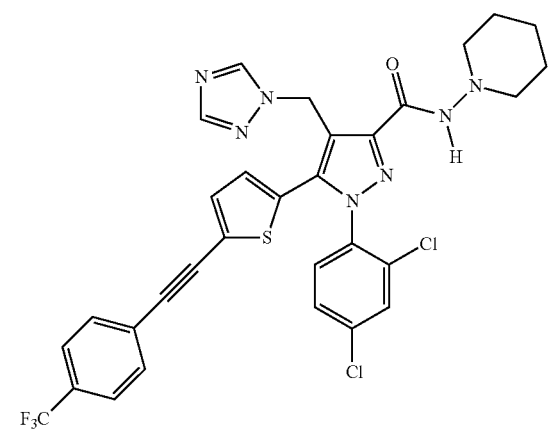
Compound 112
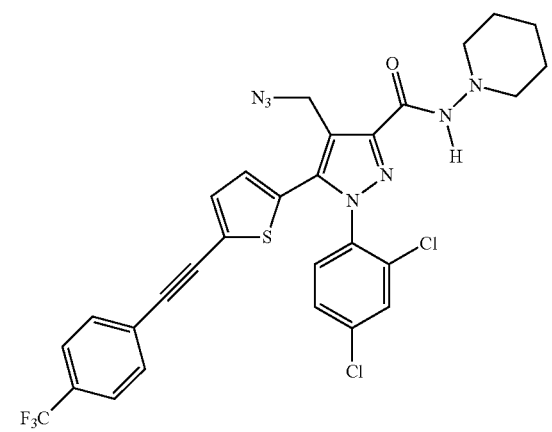
Compound 113
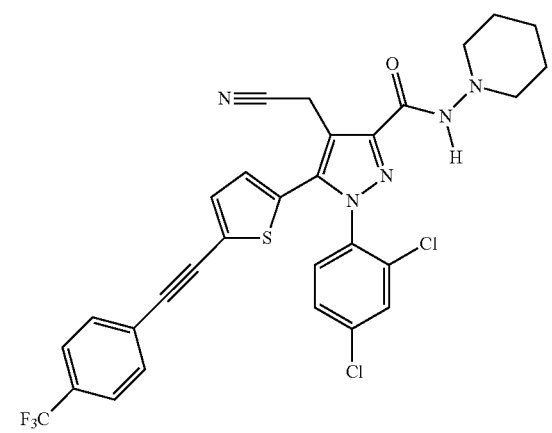

Compound 119
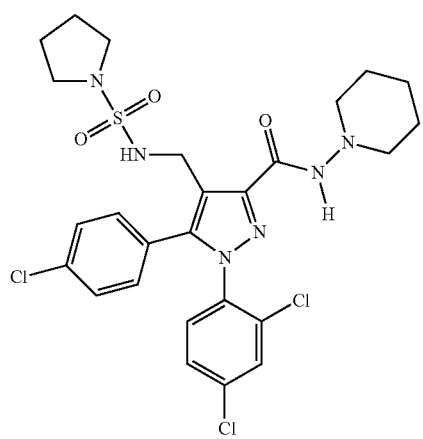
Compound 122
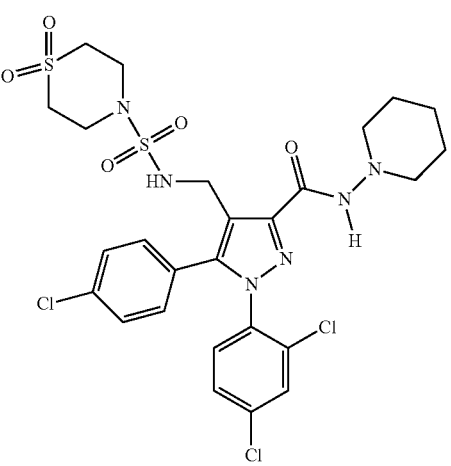
Compound 120
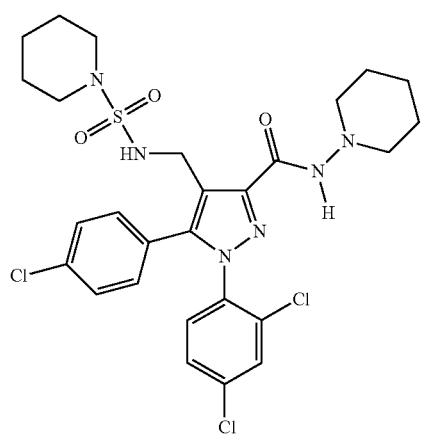
Compound 123
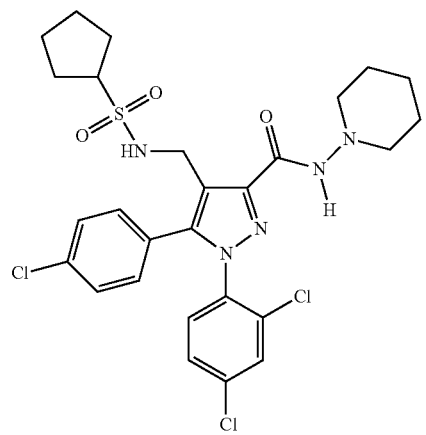
Compound 121
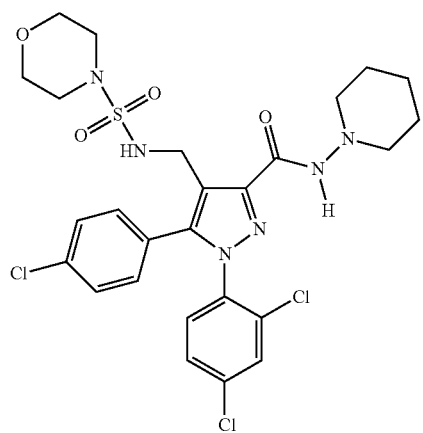
Compound 124
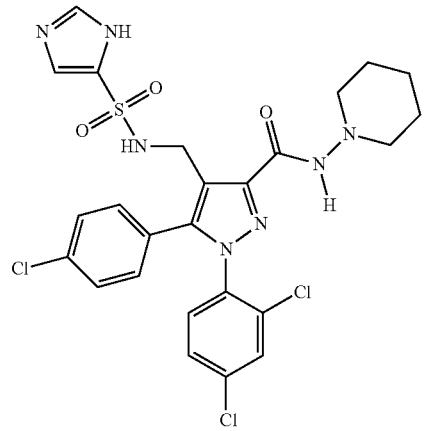

Compound 125
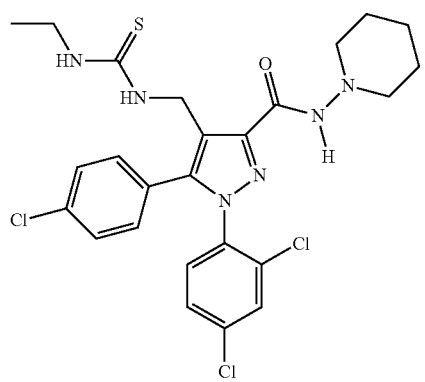
Compound 126
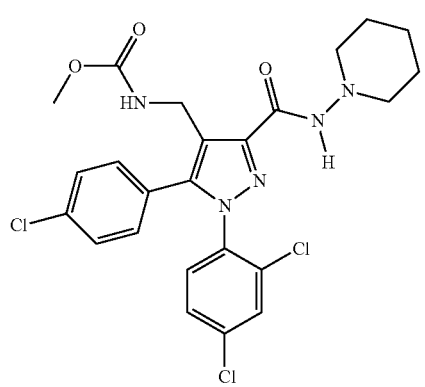
Compound 127
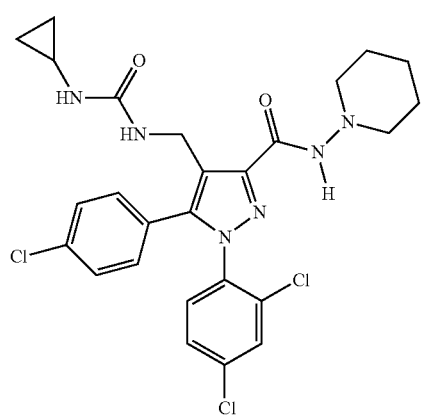
Compound 128
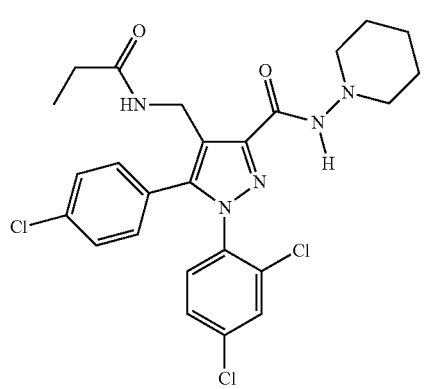
Compound 129
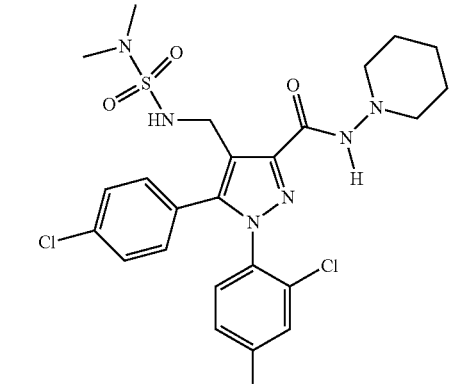
Compound 130
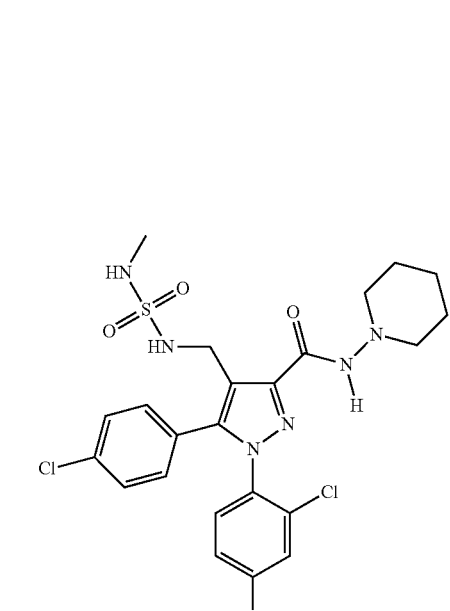
Compound 131
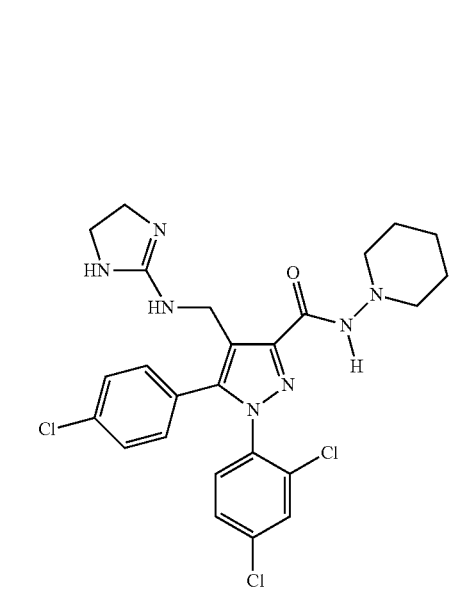

Compound 132
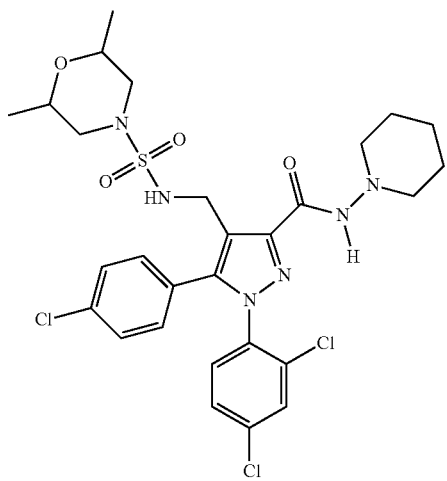
Compound 135
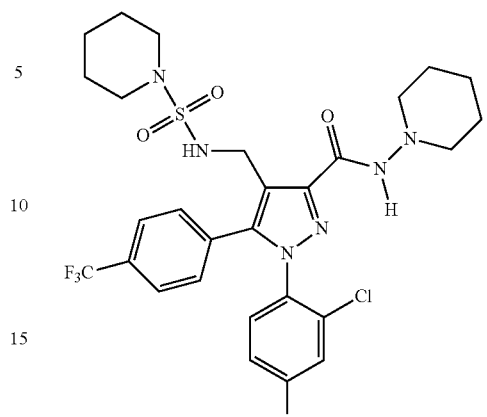
Compound 133
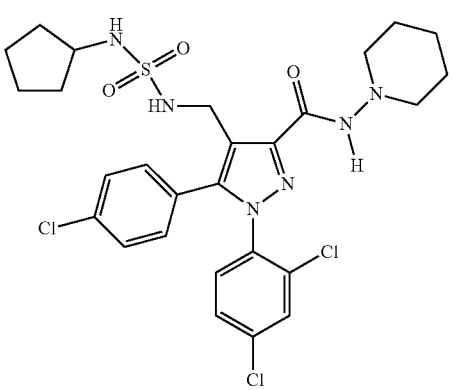
Compound 136
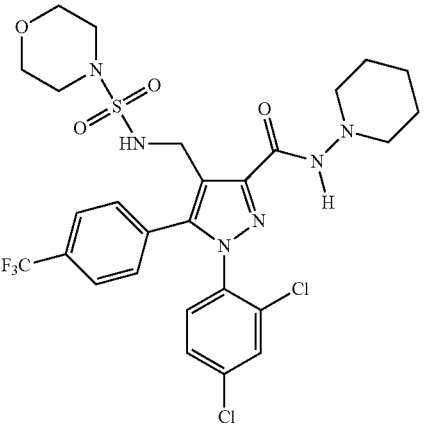
Compound 134
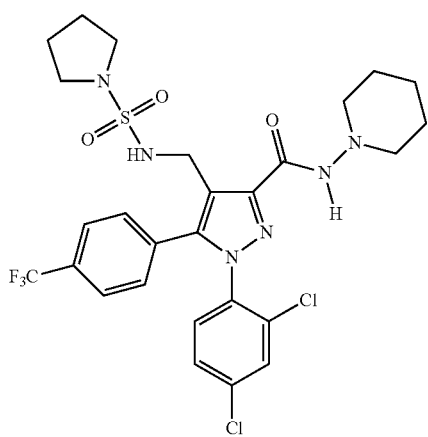
Compound 137
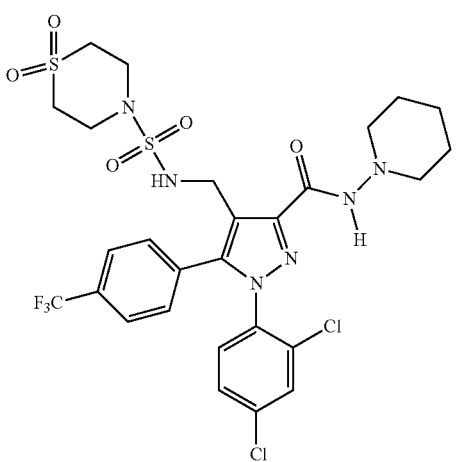

Compound 138
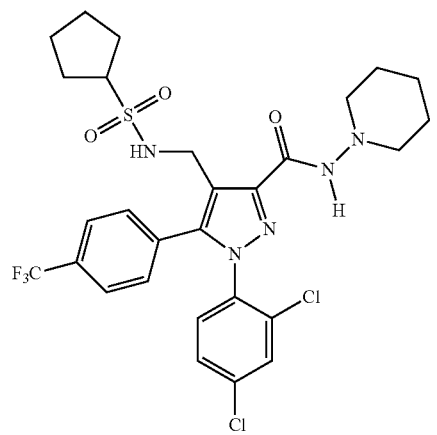
Compound 139
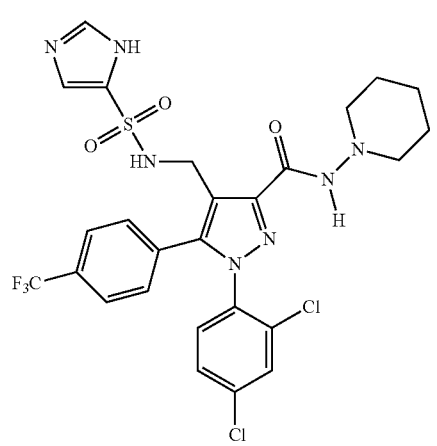
Compound 140
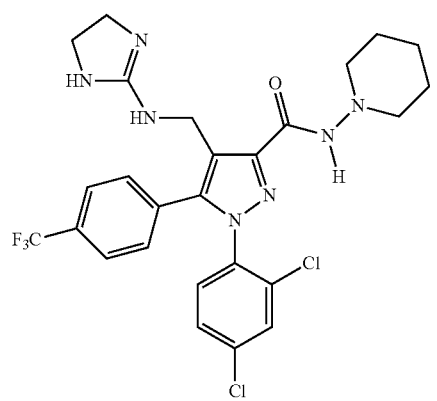
Compound 141
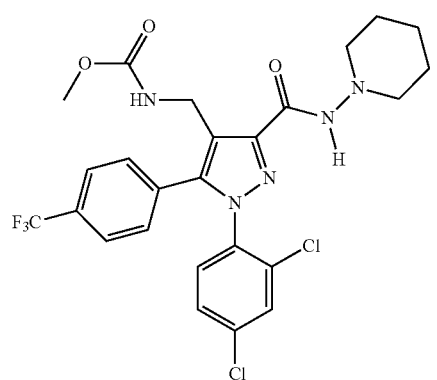
Compound 142
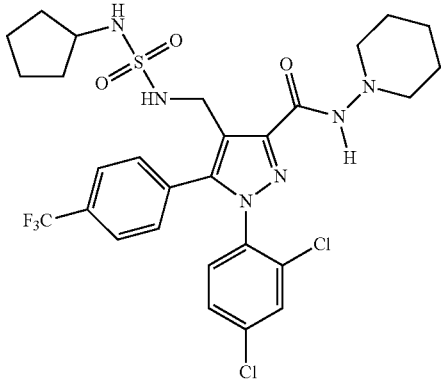
Compound 143
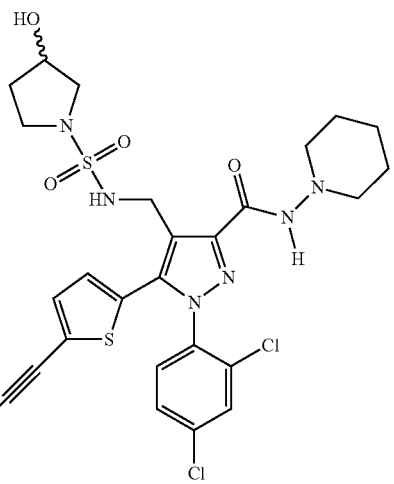
Compound 144
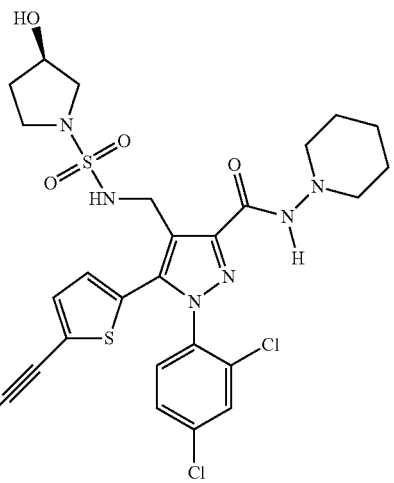

Compound 145
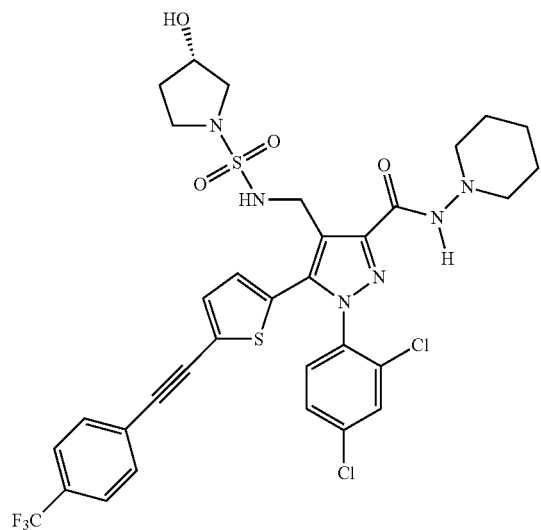
Compound 146
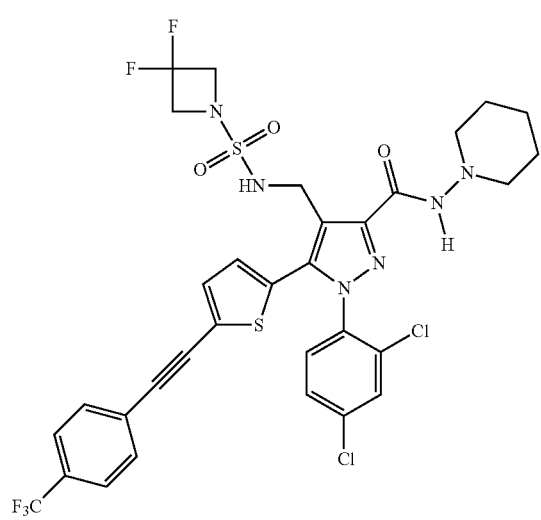
Compound 147
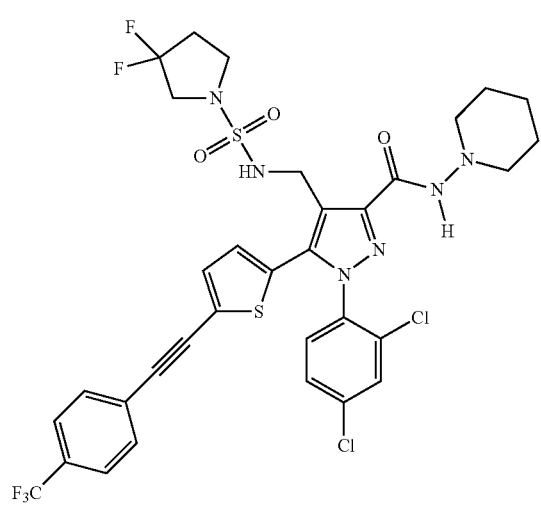
Compound 148
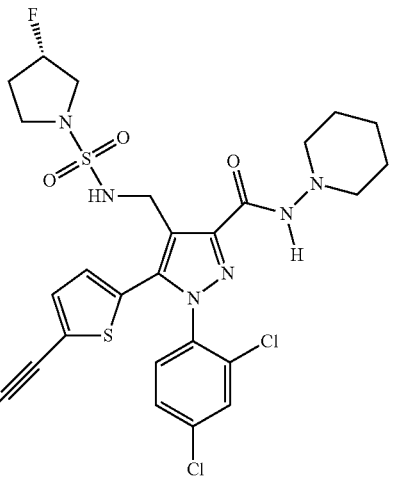
Compound 149
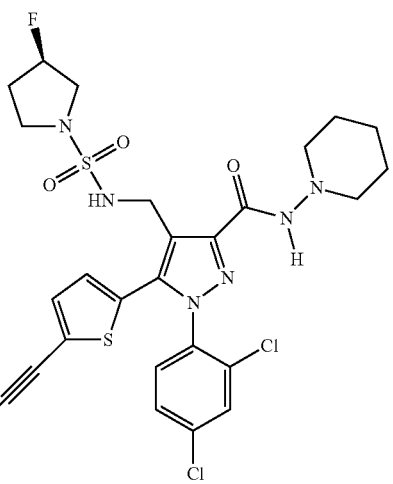
Compound 150
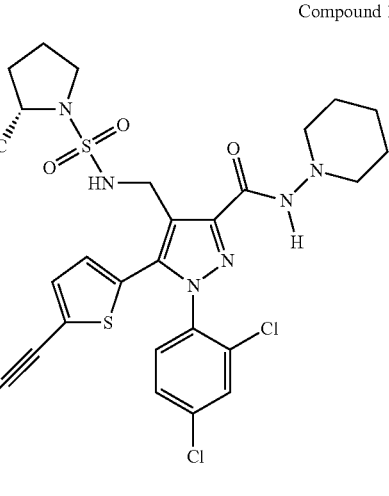

Compound 151
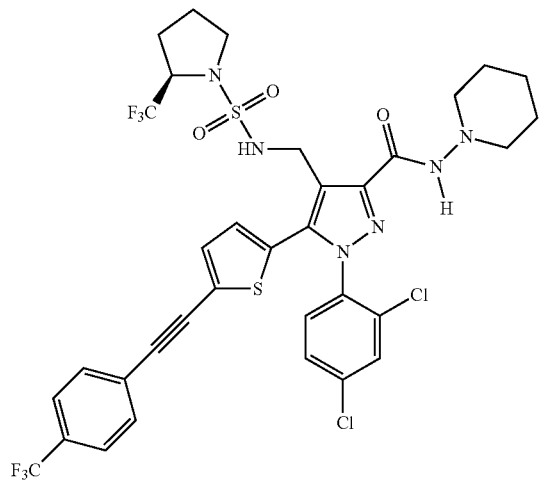
Compound 152
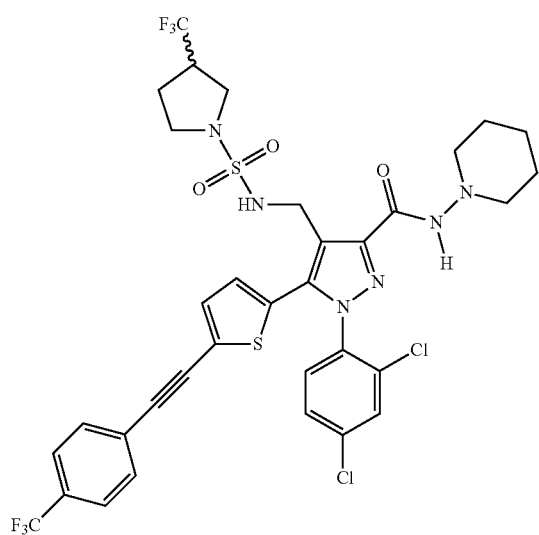
Compound 153
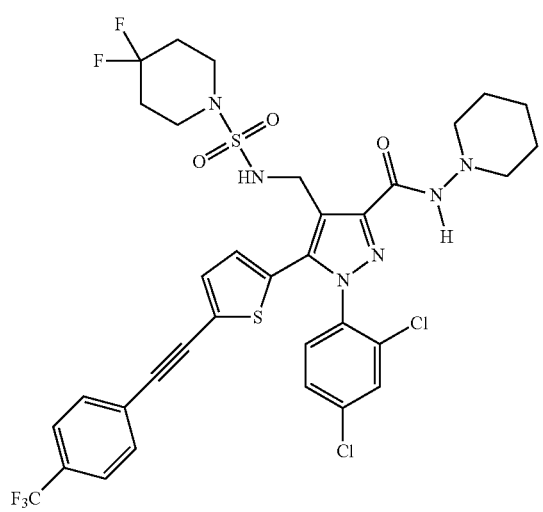
Compound 154
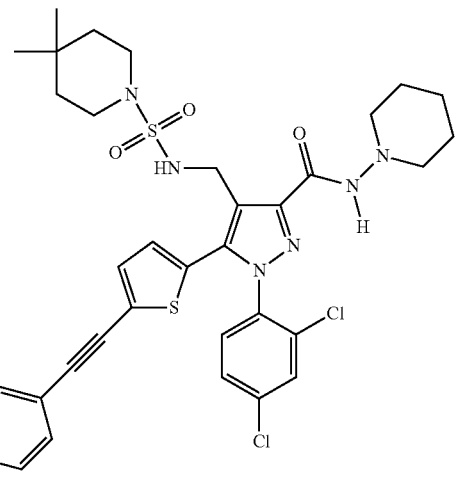
Compound 155
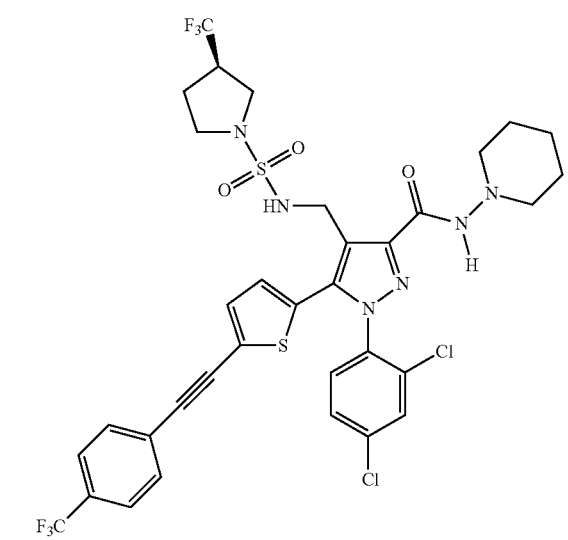
Compound 156
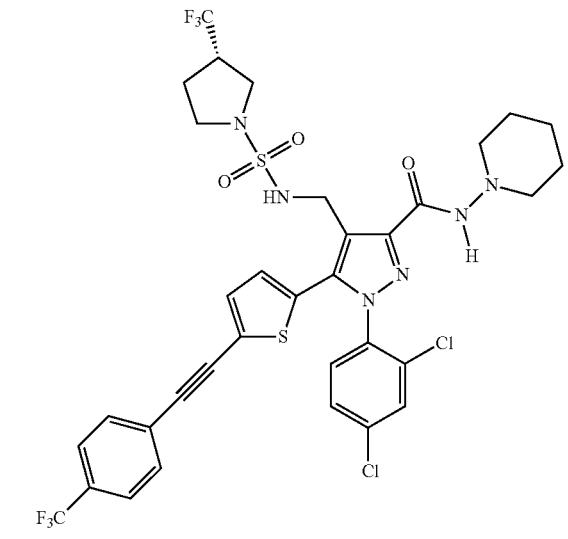

Compound 157
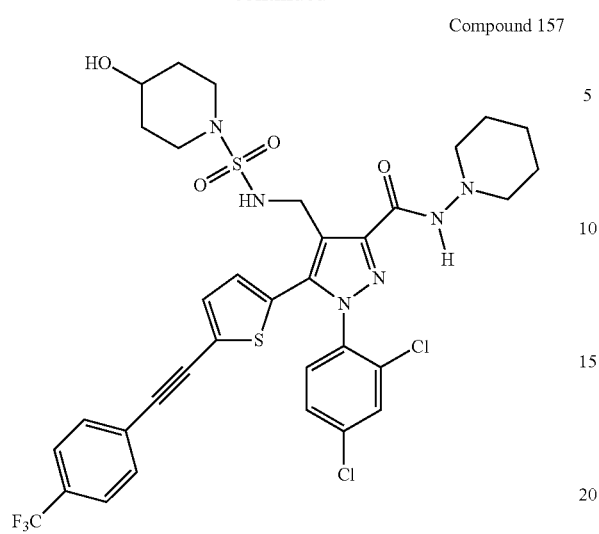
The pyrazole compounds described herein can be prepared by methods well known in the art. The route shown in Scheme I below exemplifies synthesis of pyrazole compounds of this invention.
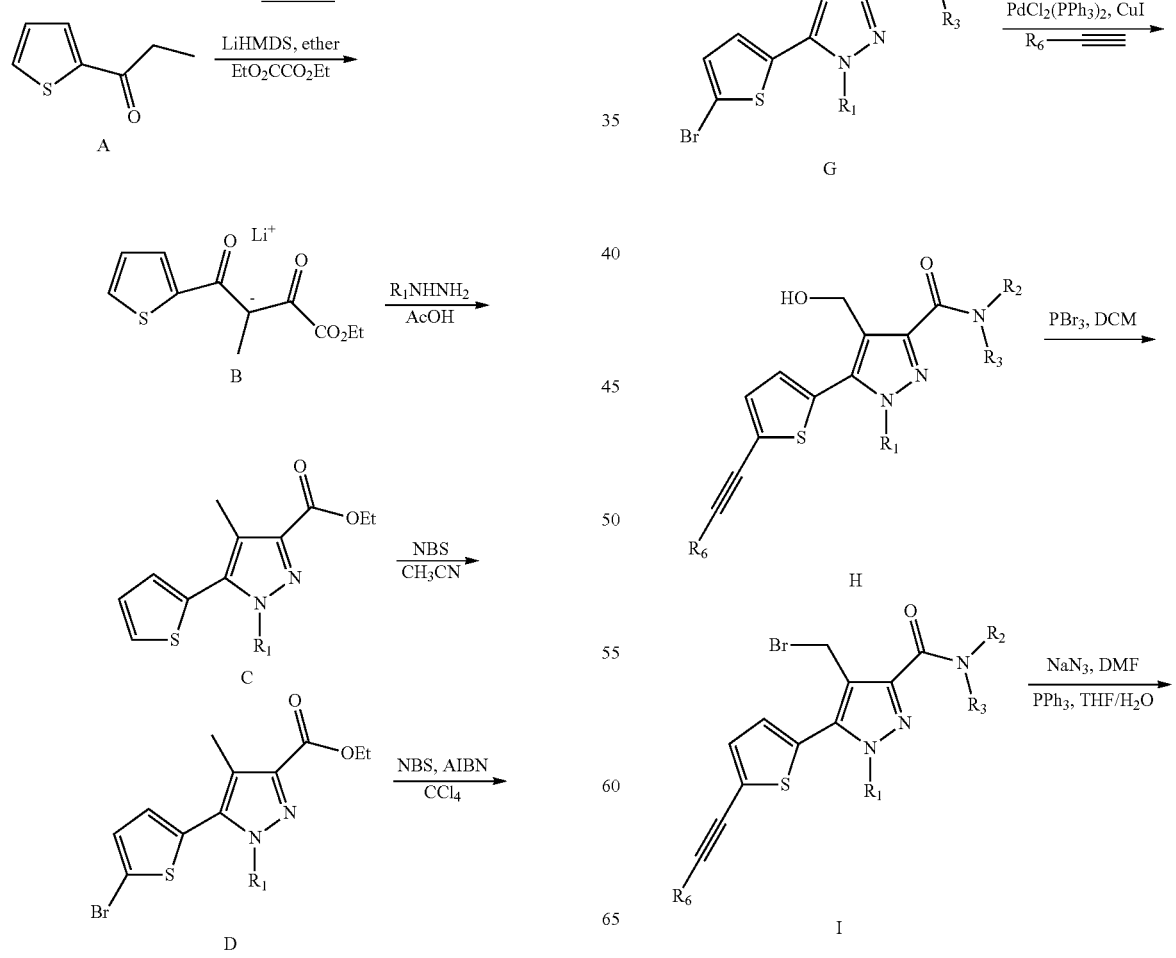

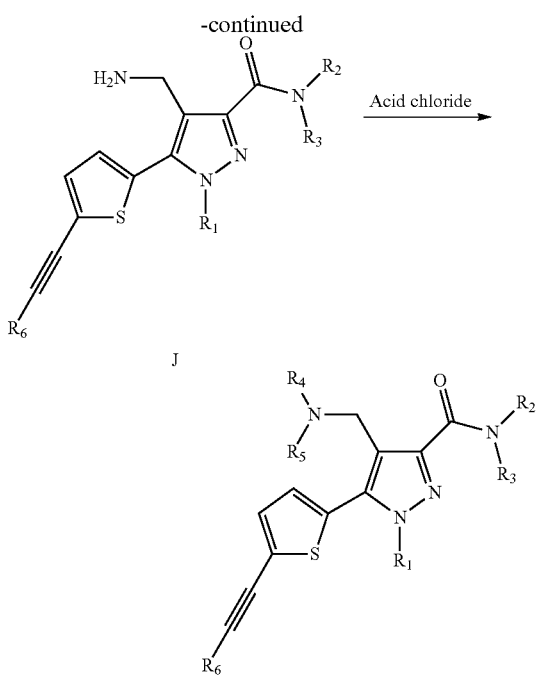

Specifically, a thiophene compound containing a ketone group (compound A) can react with an oxalate compound (diethyl oxalate) in the presence of a base to form a 1,3-dione compound containing an ester group (compound B). The 1,3-dione compound can be coupled with a hydrazine followed by intramolecular cyclization under refluxing acetic acid to provide a pyrazole compound containing an ester group (compound C). Regioselective bromination of the pyrazole compound can be achieved by using N-bromosuccinimide in THF at room temperature to afford the corresponding 5-bromo compound (compound D). This compound can be further brominated to yield a dibromide compound (compound E), which in turn is treated with silver nitrate in acetone/water (1:1) to obtain a hydroxyl bromide compound (compound F). It can react with different amines under various reaction conditions (in the presence of aluminium chloride) to formamide (compound G). The bromo group on the amide can subsequently be converted into an alkyne group by using Pd(PPh$_3$)$_2$Cl$_2$ and CuI as catalysts. The hydroxyl group on the compound thus formed (compound H) is subjected to bromination (PBr$_3$) to form a bromide (compound I).

Compound I can react with sodium azide followed by Staudinger reduction (PPh$_3$) to afford the corresponding primary amine (compound J), which can be coupled with different acid chloride (e.g., sulfonyl chloride) to obtain certain compounds of the invention (e.g., compounds 10-85). Optionally, compound I can directly undergo $S_N2$ substitution to form other compounds of the invention (e.g., compounds 87-113).

A pyrazole compound thus synthesized can be purified by any suitable method, such as column chromatography, high-pressure liquid chromatography, or recrystallization.

Other pyrazole compounds of this invention (e.g., compounds 119-142) can be prepared using other suitable starting materials through the above-described synthetic routes and others known in the art. The methods set forth above may also additionally include steps to add or remove suitable protecting groups in order to ultimately allow synthesis of the pyrazole compounds. In addition, various synthetic steps may be performed in an alternate sequence or order to give the desired compounds. Synthetic chemistry transformations and protecting group methodologies (protection and deprotection) useful in synthesizing applicable pyrazole compounds are known in the art and include, for example, those described in R. Larock, *Comprehensive Organic Transformations*, VCH Publishers (1989); T. W. Greene and P. G. M. Wuts, *Protective Groups in Organic Synthesis,* 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The pyrazole compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one pyrazole compound described above and a pharmaceutical acceptable carrier.

Further, this invention covers a method of administering an effective amount of one or more of the pyrazole compounds to a patient having a disease described in the summary section above. "An effective amount" refers to the amount of an active pyrazole compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more pyrazole compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active pyrazole compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active pyrazole compound. Examples of other carriers include colloidal silicon oxide, magnesium stearate, cellulose, sodium lauryl sulfate, and D&C Yellow #10.

The pyrazole compounds described above can be preliminarily screened for their efficacy in treating above-described diseases by an in vitro assay and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of Compounds 10-85 and 143-157

The general procedure is illustrated immediately below using compound 10 as a specific example.

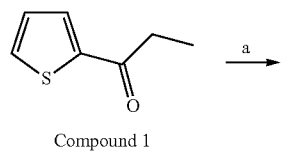

Compound 1

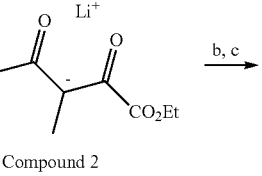

Compound 2

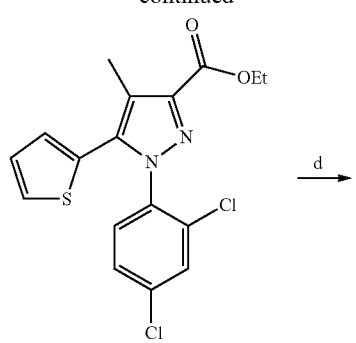

Compound 3

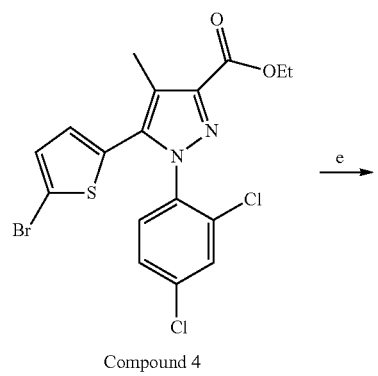

Compound 4

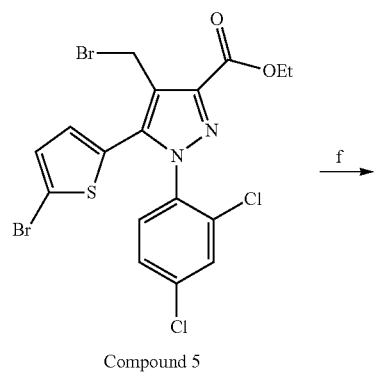

Compound 5

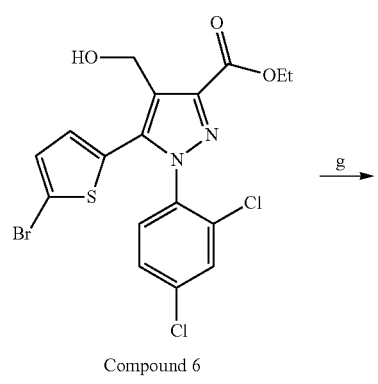

Compound 6

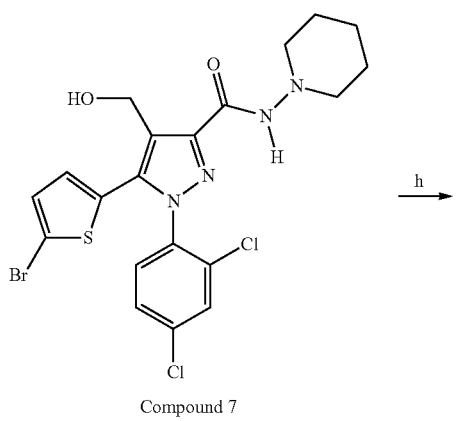

Compound 7 h →

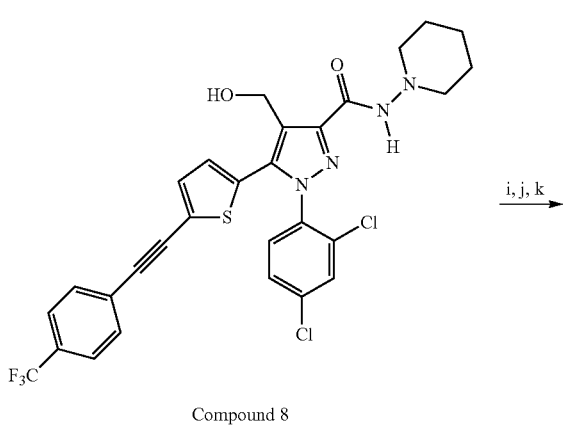

Compound 8 i, j, k →

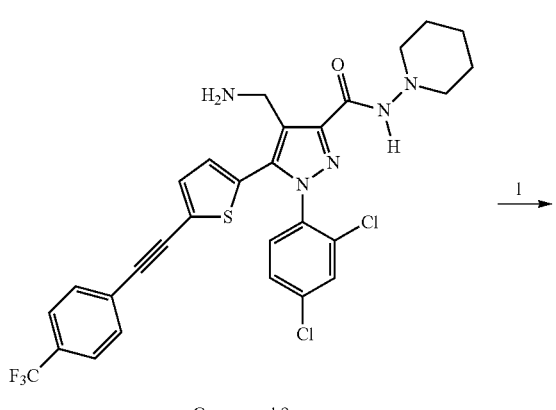

Compound 9 l →

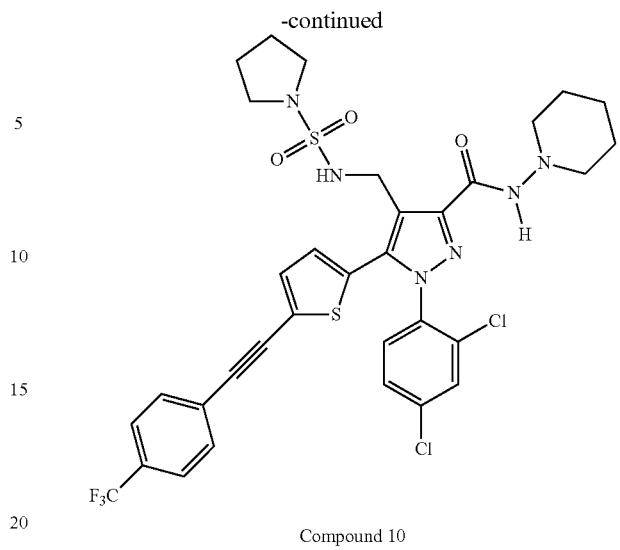

Compound 10

Reagents and conditions: (a) LiHMDS, diethyl oxalate, THF/Et$_2$O, −78° C. to rt, 20 h, 85%; (b) 2,4-dichlorophenylhydrazine hydrochloride, EtOH, rt, 22h; (c) AcOH, 120° C., 24 h, 50% over two steps; (d) NBS, CH$_3$CN, 0° C. to rt, 16 h, 95%; (e) NBS, AIBN, CCl$_4$, 80° C., 16 h; (f) AgNO$_3$, Acetone/H$_2$O = 1/1, 60° C., 16 h, 68% over two steps; (g) AlCl$_3$, 1-aminopiperidine, DCE, rt, 16 h, 97%; (h) PdCl$_2$(PPh$_3$)$_2$, CuI, 1-ethynyl-4-(trifluromethyl) benzene, 2-ethanolamine, THF/H$_2$O (1/1), 80° C., 12 h, 70%; (i) PBr$_3$, CH$_2$Cl$_2$, 0° C. to rt, 2 h; (j) NaN$_3$, DMF, rt, 3h; (k) PPh$_3$, THF/H$_2$O (1/1), rt, 16 h, 66% over three steps; (l) Pyrrolidine-1-sulfonyl chloride, Et$_3$N, DMF, 0°C. to rt, 16 h; 87%.

Lithium salt of ethyl 3-methyl-2,4-dioxo-4-thiophen-2-yl-butanonate (Compound 2)

To a magnetic stirred solution of lithium bis-(trimethylsilyl)amide (22.2 mL, 22.20 mmol, 1.0 M in THF) in diethyl ether (40 mL) at −78° C. was added 1-(2-thienyl)-1-propanone (2.81 g, 20.04 mmol) in diethyl ether (15 mL) dropwise under an argon atmosphere. After the mixture was stirred at the same temperature for additional 45 min, diethyl oxalate (3.3 mL, 24.40 mmol) was added dropwise. The reaction mixture was allowed to warm up to room temperature and stirred for another 16 h. The reaction precipitate was filtered, washed with diethyl ether, and dried under vacuum to afford the crude lithium salt 2 (4.21 g, 85%) as a pale yellow solid.

1-(2,4-Dichlorophenyl)-4-methyl-5-thiophen-2-yl-1H-pyrazole-3-carboxylic acid ethyl ester (Compound 3)

To a solution of lithium salt 2 (3.21 g, 13.04 mmol) in ethanol (35 mL) was added 2,4-dichlorophenylhydrazine hydrochloride (3.01 g, 14.05 mmol) in one portion at room temperature under nitrogen. The resulting mixture was stirred at the same temperature for 22 h. After reaction was completed, the precipitate was filtered, washed with ethanol and diethyl ether, dried under vacuum to give a light yellow solid (3.31 g). This crude solid, without purification, was dissolved in acetic acid (30 mL) and heated to reflux for 24 h. The reaction mixture was poured into ice water and extracted with ethyl acetate (2 ×30 mL). The combined extracts were washed with water, saturated aqueous sodium bicarbonate, and brine, dried over anhydrous sodium sulfate, filtered, and evaporated. Purification by flash chromatography on silica gel with n-hexane/ethyl acetate (9:1) gave ester 3 (2.49 g, 50% over two steps) as a white solid: mp 121-122° C.; $^1$H NMR (CDCl$_3$) δ 7.43 (d, J=2.1 Hz, 1H), 7.39-7.34 (m, 2H), 7.32 (d, J=3.6 Hz, 1H), 7.00 (dd, J=5.1, 3.6 Hz, 1H), 6.89 (d, J=5.1 Hz, 1H), 4.45 (q, J=7.2 Hz, 2H), 2.44 (s, 3H), 1.42 (t, J=7.2 Hz, 3H); $^{13}$C NMR (CDCl$_3$) δ 162.7, 142.8, 137.8, 136.3, 136.0, 133.9, 131.0, 129.6, 128.8, 128.5, 127.7, 127.6, 127.2, 119.9, 60.9, 14.4, 9.9; ESMS m/z: 381.0 (M+1), 403.0 (M+23).

5-(5-Bromothiophen-2-yl)-1-(2,4-dichlorophenyl)-4-methyl-1H-pyrazole-3-carboxylic acid ethyl ester (Compound 4)

To a magnetically stirred solution of 3 (2.21 g, 5.79 mmol) in acetonitrile (20 mL) was added NBS (1.24 g, 6.96 mmol) in small portions under argon at 0° C. The resulting mixture was then warmed to room temperature and stirred for 16 h. The reaction was quenched with saturated aqueous sodium thiosulfate and concentrated under reduced pressure to remove acetonitrile. The aqueous layer was extracted with ethyl acetate (2×40 mL). The organic layers were combined, washed with water, brine, dried over anhydrous sodium sulfate, filtered and concentrated to give crude residue, which was purified by flash chromatography eluting with n-hexane/ethyl acetate (9:1) to afford 5-bromo ester 4 (2.53 g, 95%) as a white solid: mp 93-94° C.; $^1$H NMR (CDCl$_3$) δ 7.46 (d, J=1.8 Hz, 1H), 7.36-7.35 (m, 1H), 7.34 (d, J=1.8 Hz, 1H), 6.96 (d, J=3.9 Hz, 1H), 6.64 (d, J=3.9 Hz, 1H), 4.44 (q, J=7.2 Hz, 2H), 2.42 (s, 3H), 1.42 (t, J=7.2 Hz, 3H); $^{13}$C NMR (CDCl$_3$) δ 161.7, 142.2, 136.1, 135.8, 134.9, 133.0, 130.3, 129.5, 129.3, 128.6, 127.2, 119.5, 114.2, 114.1, 60.2, 13.8, 9.3; ESMS m/z: 460.9 (M+1), 482.9 (M+23);

Ethyl 4-(bromomethyl)-5-(5-bromothiophen-2-yl)-1-(2,4-dichlorophenyl)-1H-pyrazole-3-carboxylate (Compound 5)

To a magnetically stirred solution of 4 (2.20 g, 4.78 mmol) in CCl$_4$ (22 mL) was added NBS (1.1 g, 6.21 mmol) and AIBN (0.05 g, 0.33 mmol). The resulting mixture was refluxed for 16 h. After cooling to room temperature, the precipitate was filtered. The solvent was removed from the filtrate under reduced pressure to give dibromide 5 as a pale yellow liquid; $^1$H NMR (CDCl$_3$) δ 7.48 (d, J=2.0 Hz, 1H), 7.38-7.32 (m, 2H), 7.01 (d, J=3.6 Hz, 1H), 6.99 (d, J=3.6 Hz, 1H), 4.77 (s, 2H), 4.48 (q, J=7.2 Hz, 2H), 1.43 (t, J=7.2 Hz, 3H); $^{13}$C NMR (CDCl$_3$) δ 161.5, 142.2, 138.4, 137.1, 135.0, 133.8, 130.8, 130.5, 130.3, 130.2, 128.2, 128.0, 120.6, 116.4, 61.6, 22.4, 14.3; ESMS m/z: 538.8 (M+1).

Ethyl 5-(5-bromothiophen-2-yl)-1-(2,4-dichlorophenyl)-4-(hydroxymethyl)-1H-pyrazole-3-carboxylate (Compound 6)

To a magnetically stirred solution of silver nitrate (3.25 g, 19.12 mmol) in 100 mL of 50% aqueous acetone at room temperature was added a suspension of crude compound 5 in 70% aqueous acetone (50 mL). The mixture was stirred at 60° C. overnight. After cooling to room temperature, the insoluble residue was filtered off and the filtrate was concentrated under vacuum to remove acetone. The mixture was extracted with CH$_2$Cl$_2$, and the combined organic extracts were washed with water, dried over anhydrous magnesium sulfate, filtered and concentrated to give crude residue, which was purified by flash chromatography eluting with n-hexane/ ethyl acetate (2:1) to afford hydroxy ester 6 (1.55 g, 68% over two steps) as a white solid: $^1$H NMR (CDCl$_3$) δ 7.46 (dd, J=1.2, 1.2 Hz, 1H), 7.33 (d, J=1.2 Hz, 2H), 6.96 (d, J=3.6 Hz, 1H), 6.76 (d, J=3.6 Hz, 1H), 4.71 (d, J=7.2 Hz, 2H), 4.48 (q, J=7.2 Hz, 2H), 3.76 (t, J=7.2 Hz, 1H), 1.42 (t, J=7.2 Hz, 3H); $^{13}$C NMR (CDCl$_3$) δ 163.3, 142.9, 137.3, 136.8, 135.0, 133.7, 130.7, 130.4, 130.3, 130.1, 128.4, 127.8, 124.2, 115.8, 61.9, 54.5, 14.2; ESMS m/z: 498.9 (M+23).

5-(5-Bromothiophen-2-yl)-1-(2,4-dichlorophenyl)-4-(hydroxymethyl)-N-(piperidin-1-yl)-1H-pyrazole-3-carboxamide (Compound 7)

To a magnetically stirred solution of 6 (4.40 g, 9.24 mmol) and aluminum trichloride (2.46 g, 18.48 mmol) in dichloride ethane (88 mL) was added 1-aminopiperidine (3.70 g, 36.96 mmol) slowly under argon at 0° C. The resulting mixture was allowed to warm up to room temperature and stirred for 16 h, then quenched with ice water. The aqueous phase was extracted with CH$_2$Cl$_2$ (2×40 mL). The combined organic extracts were washed with water and brine, dried over anhydrous sodium sulfate, filtered, and concentrated under reduced pressure to give crude residue, which was purified by flash chromatography eluting with n-hexane/ethyl acetate (1:1) to afford Compound 7 (4.75 g, 97%) as a white solid: $^1$H NMR (CDCl$_3$) δ 7.73 (s, 1H), 7.49 (d, J=2.4 Hz, 1H), 7.35 (dd, J=8.4, 2.4 Hz, 1H), 7.28 (d, J=8.4 Hz, 1H), 6.95 (d, J=4.0 Hz, 1H), 6.69 (d, J=4.0 Hz, 1H), 5.17 (t, J=7.2 Hz, 1H), 4.67 (d, J=7.2 Hz, 2H), 2.83 (brs, 4H), 1.78-1.73 (m, 4H), 1.42 (brs, 2H); $^{13}$C NMR (CDCl$_3$) δ 160.0, 144.7, 136.9, 136.6, 135.0, 133.6, 130.7, 130.3, 130.2, 128.6, 128.1, 124.0, 115.8, 57.1, 54.7, 25.3, 23.2; ESMS m/z: 529.1 (M+1).

1-(2,4-Dichlorophenyl)-5-(5-(2-(4-(trifluoromethyl)phenyl)ethynyl)thiophen-2-yl)-4-(hydroxymethyl)-N-(piperidin-1-yl)-1H-pyrazole-3-carboxamide (Compound 8)

A solution of bromothiophene 7 (1.20 g, 2.26 mmol), PdCl$_2$(PPh$_3$)$_2$ (0.16 g, 0.23 mmol), CuI (0.06 g, 0.28 mmol) and 2-ethanolamine (0.5 M(aq), 14 mL, 6.78 mmol) in THF (50 mL) was stirred and degassed under argon in a pressure vessel for 10 min, at which time 1-ethynyl-4-(trifluoromethyl)benzene (0.58 g, 3.39 mmol) was added in one portion. The resulting mixture was heated at 80° C. in an oil bath for 12 h. After cooling to room temperature, the reaction mixture was poured into water (20 mL) and the aqueous layer was extracted with ethyl acetate (2×40 mL). The combined organic extracts were washed with water and brine, dried over anhydrous sodium sulfate, filtered, and concentrated under reduced pressure to give crude residue, which was purified by flash chromatography with n-hexane/ethyl acetate (1:1) to afford compound 8 (0.98 g, 70%) as a white solid: $^1$H NMR (CDCl$_3$) δ 7.75 (s, 1H), 7.57 (s, 1H), 7.50 (d, J=2.0 Hz, 1H), 7.36 (dd, J=8.4, 2.0 Hz, 1H), 7.32 (d, J=8.4 Hz, 1H), 7.18 (d, J=4.0 Hz, 1H), 6.84 (d, J=4.0 Hz, 1H), 5.21 (t, J=3.2 Hz, 1H), 4.73 (d, J=3.2 Hz, 2H), 2.83 (brs, 4H), 1.77-1.75 (m, 4H), 1.43 (brs, 2H); $^{13}$C NMR (CDCl$_3$) δ 160.0, 144.8, 136.8, 136.6, 135.1, 133.6, 132.6, 131.5, 130.7, 130.2 (q, J$_{C-F}$=32.6 Hz), 130.3, 129.7, 129.1, 128.0, 126.1, 125.7, 125.3 (q, J$_{C-F}$=3.6 Hz), 123.7 (q, J$_{C-F}$=270.9 Hz), 93.6, 83.7, 57.1, 54.8, 25.3, 23.1; ESMS m/z: 619.1 (M+1).

4-(Aminomethyl)-1-(2,4-dichlorophenyl)-5-(5-(2-(4-(trifluoromethyl)phenyl)ethynyl)thiophen-2-yl)-N-(piperidin-1-yl)-1H-pyrazole-3-carboxamide (Compound 9)

To a magnetically stirred solution of compound 8 (1.00 g, 1.62 mmol) in CH$_2$Cl$_2$ (50 mL) at 0° C. was added PBr$_3$ (0.87 g, 3.23 mmol) dropwise. The resulting mixture was allowed to warm up to room temperature and stirred for 2 h, and then quenched with ice water. The aqueous phase was extracted with CH$_2$Cl$_2$ (2×20 mL). The combined organic extracts were washed with water and brine, dried over anhydrous sodium sulfate, filtered, and concentrated under reduced pressure to give the corresponding bromide, which in turn, without purification, was allowed to react with NaN$_3$ (0.53 g, 8.08 mmol) in DMF (10 mL) at room temperature for 3 h. The reaction mixture was poured into water (10 mL) and the aqueous layer was extracted with ethyl acetate (2×20 mL). The combined organic extracts were washed with water and brine, dried over anhydrous sodium sulfate, filtered, and concentrated under reduced pressure to yield the corresponding azide. This azido compound, without purification, was further treated with PPh$_3$ (0.51 g, 1.94 mmol) in THF/H$_2$O (1/1) (20 mL) at room temperature for 16 h to afford compound 9 (0.66 g, 66% over three steps) as a pale yellow solid after chromatographic purification (CH$_2$Cl$_2$:MeOH=9:1): $^1$H NMR (CDCl$_3$) δ 7.85 (brs, 1H), 7.62-7.56 (m, 4H), 7.51 (d, J=1.8 Hz, 1H), 7.38-7.32 (m, 2H), 7.19 (d, J=3.9 Hz, 1H), 6.91 (d, J=3.9 Hz, 1H), 3.99 (s, 2H), 2.87-2.79 (m, 4H), 2.01 (s, 1H), 1.76 (quintet, J=5.4 Hz, 4H), 1.49-1.38 (m, 2H); ESMS m/z: 618.0 (M+1).

1-(2,4-Dichlorophenyl)-N-(piperidin-1-yl)-4-((pyrrolidine-1-sulfonamido) methyl)-5-(5-((4-(trifluoromethyl)phenyl)ethynyl)thiophen-2-yl)-1H-pyrazole-3-carboxamide (Compound 10)

To a magnetically stirred solution of Compound 9 (1.15 g, 1.86 mmol) and Et$_3$N (0.38 g, 3.72 mmol) in DMF (10 mL) at 0° C. was added pyrrolidine-1-sulfonyl chloride (0.47 g, 2.79 mmol) dropwise. The resulting mixture was allowed to warm up to room temperature for 16 h, and then quenched with water. The aqueous phase was extracted with ethyl acetate (2×20 mL), and the combined organic extracts were washed with water and brine, dried over anhydrous sodium sulfate, filtered, and concentrated under reduced pressure to give crude residue, which was purified by flash chromatography with n-hexane/ethyl acetate (1:1) as eluting solvent to afford the desired product 10 (1.21 g, 87%) as a white solid: mp 163-164° C.; $^1$H NMR (CDCl$_3$) δ 7.71 (s, 1H), 7.61-7.56 (m, 4H), 7.53 (d, J=2.0 Hz, 1H), 7.40-7.33 (m, 2H), 7.23 (d, J=3.6 Hz, 1H), 7.22 (d, J=3.6 Hz, 1H), 6.50 (t, J=6.8 Hz, 1H), 4.34 (d, J=6.8 Hz, 2H), 3.28-3.25 (m, 4H), 2.87-2.81 (m, 4H), 1.86 (quintet, J=3.6 Hz, 4H), 1.78 (quintet, J=5.6 Hz, 4H), 1.48-1.42 (m, 2H); $^{13}$C NMR (CDCl$_3$) δ 159.2, 144.3, 137.4, 136.7, 134.8, 133.3, 132.7, 131.3, 130.6, 130.2, 130.1, 130.0 (q, J$_{C-F}$=33.0 Hz), 128.5, 127.9, 125.9, 125.6, 125.0 (q, J$_{C-F}$=4.0 Hz), 123.5 (q, J$_{C-F}$=270.5 Hz), 119.7, 93.4, 83.7, 56.9, 47.7, 37.2, 25.3, 25.0, 22.9; ESMS m/z: 751.0 (M+1).

(Z)-4-((2-Cyano-3-cyclopropylguanidino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 11)

ES-MS (M+1): 725.1.

(E)-4-((1-Amino-2-nitrovinylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 12)

ES-MS (M+1): 704.1.

(E)-1-(2,4-Dichlorophenyl)-4-((1-(methylamino)-2-nitrovinylamino)methyl)-N-(piperidin-1-yl)-5-(5-((4-(trifluoromethyl)phenyl)ethynyl)thiophen-2-yl)-1H-pyrazole-3-carboxamide (Compound 13)

ES-MS (M+1): 718.1.

1-(2,4-Dichlorophenyl)-4-(guanidinomethyl)-N-(piperidin-1-yl)-5-(5-((4-(trifluoromethyl)phenyl)ethynyl)thiophen-2-yl)-1H-pyrazole-3-carboxamide (Compound 14)

ES-MS (M+1): 660.2.

1-(2,4-Dichlorophenyl)-4-((3-methylguanidino)methyl)-N-(piperidin-1-yl)-5-(5-((4-(trifluoromethyl)phenyl)ethynyl)thiophen-2-yl)-1H-pyrazole-3-carboxamide (Compound 15)

ES-MS (M+1): 674.2.

4-(Acetamidomethyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 16)

ES-MS (M+1): 660.1.

Methyl(1-(2,4-dichlorophenyl)-3-(piperidin-1-ylcarbamoyl)-5-(5-((4-(trifluoromethyl)phenyl)ethynyl)thiophen-2-yl)-1H-pyrazol-4-yl)methylcarbamate (Compound 17)

ES-MS (M+1): 676.1.

Ethyl(1-(2,4-dichlorophenyl)-3-(piperidin-1-ylcarbamoyl)-5-(5-((4-(trifluoromethyl)phenyl)ethynyl)thiophen-2-yl)-1H-pyrazol-4-yl)methylcarbamate (Compound 18)

ES-MS (M+1): 690.1.

1-(2,4-Dichlorophenyl)-4-((3-ethylureido)methyl)-N-(piperidin-1-yl)-5-(5-((4-(trifluoromethyl)phenyl)ethynyl)thiophen-2-yl)-1H-pyrazole-3-carboxamide (Compound 19)

ES-MS (M+1): 689.1.

4-((3-Cyclopropylureido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 20)

ES-MS (M+1): 701.1.

1-(2,4-Dichlorophenyl)-4-((3-methylthioureido)methyl)-N-(piperidin-1-yl)-5-(5-((4-(trifluoromethyl)phenyl)ethynyl)thiophen-2-yl)-1H-pyrazole-3-carboxamide (Compound 21)

ES-MS (M+1): 691.1.

4-((3-Cyclopropylthioureido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 22)

ES-MS (M+1): 717.1.

1-(2,4-Dichlorophenyl)-4-((4,5-dihydro-1H-imidazol-2-ylamino)methyl)-N-(piperidin-1-yl)-5-(5-((4-(trifluoromethyl)phenyl)ethynyl)thiophen-2-yl)-1H-pyrazole-3-carboxamide (Compound 23)

ES-MS (M+1): 686.1.

(E)-4-((2-Cyano-3-methylguanidino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 24)

ES-MS (M+1): 699.1.

1-(2,4-Dichlorophenyl)-4-(methylsulfonamidomethyl)-N-(piperidin-1-yl)-5-(5-((4-(trifluoromethyl)phenyl)ethynyl)thiophen-2-yl)-1H-pyrazole-3-carboxamide (Compound 25)

ES-MS (M+1): 696.0.

1-(2,4-Dichlorophenyl)-4-((1-methylethylsulfonamido)methyl)-N-(piperidin-1-yl)-5-(5-((4-(trifluoromethyl)phenyl)ethynyl)thiophen-2-yl)-1H-pyrazole-3-carboxamide (Compound 26)

ES-MS (M+1): 724.1.

1-(2,4-Dichlorophenyl)-4-((N,N-dimethylsulfamoylamino)methyl)-N-(piperidin-1-yl)-5-(5-((4-(trifluoromethyl)phenyl)ethynyl)thiophen-2-yl)-1H-pyrazole-3-carboxamide (Compound 27)

ES-MS (M+1): 725.1.

1-(2,4-Dichlorophenyl)-4-((N-methylsulfamoylamino)methyl)-N-(piperidin-1-yl)-5-(5-((4-(trifluoromethyl)phenyl)ethynyl)thiophen-2-yl)-1H-pyrazole-3-carboxamide (Compound 28)

ES-MS (M+1): 711.0.

1-(2,4-Dichlorophenyl)-4-((N-isopropylsulfamoylamino)methyl)-N-(piperidin-1-yl)-5-(5-((4-(trifluoromethyl)phenyl)ethynyl)thiophen-2-yl)-1H-pyrazole-3-carboxamide (Compound 29)

ES-MS (M+1): 739.1.

4-((N-tert-Butylsulfamoylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 30)

ES-MS (M+1): 753.1.

4-(Cyclopentanesulfonamidomethyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 31)

ES-MS (M+1): 750.1.

4-((1H-Imidazole-5-sulfonamido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 32)

ES-MS (M+1): 748.0.

1-(2,4-Dichlorophenyl)-4-((4-ethylpiperazine-1-sulfonamido)methyl)-N-(piperidin-1-yl)-5-(5-((4-(trifluoromethyl)phenyl)ethynyl)thiophen-2-yl)-1H-pyrazole-3-carboxamide (Compound 33)

ES-MS (M+1): 794.1.

1-(2,4-Dichlorophenyl)-N-(piperidin-1-yl)-4-((piperidine-1-sulfonamido)methyl)-5-(5-((4-(trifluoromethyl)phenyl)ethynyl)thiophen-2-yl)-1H-pyrazole-3-carboxamide (Compound 34)

ES-MS (M+1): 765.1.

1-(2,4-Dichlorophenyl)-4-((morpholine-4-sulfonamido)methyl)-N-(piperidin-1-yl)-5-(5-((4-(trifluoromethyl)phenyl)ethynyl)thiophen-2-yl)-1H-pyrazole-3-carboxamide (Compound 35)

ES-MS (M+1): 767.1.

1-(2,4-Dichlorophenyl)-4-(3,5-dimethylpiperidine-1-sulfonamido)methyl)-N-(piperidin-1-yl)-5-(5-((4-(trifluoromethyl)phenyl)ethynyl)thiophen-2-yl)-1H-pyrazole-3-carboxamide (Compound 36)

ES-MS (M+1): 793.1.

1-(2,4-Dichlorophenyl)-4-(2,6-dimethylmorpholine-4-sulfonamido)methyl)-N-(piperidin-1-yl)-5-(5-((4-(trifluoromethyl)phenyl)ethynyl)thiophen-2-yl)-1H-pyrazole-3-carboxamide (Compound 37)

ES-MS (M+1): 795.1.

1-(2,4-Dichlorophenyl)-4-({[(1,1-dioxidothiomorpholin-4-yl)sulfonyl]amino}methyl)-N-(piperidin-1-yl)-5-(5-{[4-(trifluoromethyl)phenyl]ethynyl}thiophen-2-yl)-1H-pyrazole-3-carboxamide (Compound 38)

ES-MS (M+1): 815.0.

1-(2,4-Dichlorophenyl)-4-(6-methyl-2,4-dioxo-1,2,3,4-tetrahydropyrimidine-5-sulfonamido)methyl)-N-(piperidin-1-yl)-5-(5-((4-(trifluoromethyl)phenyl)ethynyl) thiophen-2-yl)-1H-pyrazole-3-carboxamide (Compound 39)

ES-MS (M+1): 806.1.

1-(2,4-Dichlorophenyl)-N-(piperidin-1-yl)-4-((thiophene-2-sulfonamido)methyl)-5-(5-((4-(trifluoromethyl)phenyl)ethynyl)thiophen-2-yl)-1H-pyrazole-3-carboxamide (Compound 40)

ES-MS (M+1): 764.0.

1-(2,4-Dichlorophenyl)-4-((4-methylpiperazine-1-sulfonamido)methyl)-N-(piperidin-1-yl)-5-(5-((4-(trifluoromethyl)phenyl)ethynyl)thiophen-2-yl)-1H-pyrazole-3-carboxamide (Compound 41)

ES-MS (M+1): 780.1.

4-((N-Cyclopropylsulfamoylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 42)

ES-MS (M+1): 737.1.

4-((N-Cyclopentylsulfamoylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 43)

ES-MS (M+1): 765.1.

4-((N-Cyclohexylsulfamoylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 44)

ES-MS (M+1): 779.1.

4-((N-Cycloheptylsulfamoylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 45)

ES-MS (M+1): 793.1.

4-((Aziridine-1-sulfonamido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 46)

ES-MS (M+1): 723.1.

4-((Azetidine-1-sulfonamido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 47)

ES-MS (M+1): 737.1.

4-((1,3-Oxazetidine-3-sulfonamido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 48)

ES-MS (M+1): 739.1.

4-{[(7-Azabicyclo[2.2.1]hept-7-ylsulfonyl)amino]methyl}-1-(2,4-dichlorophenyl)-N-(piperidin-1-yl)-5-(5-{[4-(trifluoromethyl)phenyl]ethynyl}thiophen-2-yl)-1H-pyrazole-3-carboxamide (Compound 49)

ES-MS (M+1): 777.1.

4-((2-Aza-bicyclo[2.2.1]heptane-2-sulfonamido)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 50)

ES-MS (M+1): 737.1.

4-(Cyclopropanesulfonamidomethyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 51)

ES-MS (M+1): 722.1.

4-(Cyclohexanesulfonamidomethyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 52)

ES-MS (M+1): 764.1.

4-((1H-Imidazole-5-sulfonamido)methyl)-5-(5-((4-chlorophenyl)ethynyl)thiophen-2-yl)-1-(2,4-dichlorophenyl)-N-(piperidin-1-yl)-1H-pyrazole-3-carboxamide (Compound 53)

ES-MS (M+1): 716.1.

5-(5-((4-Chlorophenyl)ethynyl)thiophen-2-yl)-1-(2,4-dichlorophenyl)-N-(piperidin-1-yl)-4-((pyrrolidine-1-sulfonamido)methyl)-1H-pyrazole-3-carboxamide (Compound 54)

ES-MS (M+1): 719.1.

5-(5-((4-Chlorophenyl)ethynyl)thiophen-2-yl)-1-(2,4-dichlorophenyl)-N-(piperidin-1-yl)-4-((piperidine-1-sulfonamido)methyl)-1H-pyrazole-3-carboxamide (Compound 55)

ES-MS (M+1): 733.1.

5-(5-((4-Chlorophenyl)ethynyl)thiophen-2-yl)-4-((N-cyclopentylsulfamoylamino) methyl)-1-(2,4-dichlorophenyl)-N-(piperidin-1-yl)-1H-pyrazole-3-carboxamide (Compound 56)

ES-MS (M+1): 733.1.

5-(5-((4-Chlorophenyl)ethynyl)thiophen-2-yl)-4-((N-cyclopropylsulfamoylamino) methyl)-1-(2,4-dichlorophenyl)-N-(piperidin-1-yl)-1H-pyrazole-3-carboxamide (Compound 57)

ES-MS (M+1): 705.0.

5-(5-((4-Chlorophenyl)ethynyl)thiophen-2-yl)-1-(2,4-dichlorophenyl)-4-((2,6-dimethylmorpholine-4-sulfonamido)methyl)-N-(piperidin-1-yl)-1H-pyrazole-3-carboxamide (Compound 58)

ES-MS (M+1): 763.1.

5-(5-((4-Chlorophenyl)ethynyl)thiophen-2-yl)-1-(2,4-dichlorophenyl)-4-((N-methylsulfamoylamino)methyl)-N-(piperidin-1-yl)-1H-pyrazole-3-carboxamide (Compound 59)

ES-MS (M+1): 679.1.

4-((Azetidine-1-sulfonamido)methyl)-5-(5-((4-chlorophenyl)ethynyl)thiophen-2-yl)-1-(2,4-dichlorophenyl)-N-(piperidin-1-yl)-1H-pyrazole-3-carboxamide (Compound 60)

ES-MS (M+1): 705.0.

4-((1,3-Oxazetidine-3-sulfonamido)methyl)-5-(5-((4-chlorophenyl)ethynyl)thiophen-2-yl)-1-(2,4-dichlorophenyl)-N-(piperidin-1-yl)-1H-pyrazole-3-carboxamide (Compound 61)

ES-MS (M+1): 707.1.

1-(2,4-Dichlorophenyl)-5-(5-(pent-1-ynyl)thiophen-2-yl)-N-(piperidin-1-yl)-4-((pyrrolidine-1-sulfonamido)methyl)-1H-pyrazole-3-carboxamide (Compound 62)

ES-MS (M+1): 649.2.

1-(2,4-Dichlorophenyl)-5-(5-(pent-1-ynyl)thiophen-2-yl)-N-(piperidin-1-yl)-4-((piperidine-1-sulfonamido)methyl)-1H-pyrazole-3-carboxamide (Compound 63)

ES-MS (M+1): 663.1.

1-(2,4-Dichlorophenyl)-4-((morpholine-4-sulfonamido)methyl)-5-(5-(pent-1-ynyl)thiophen-2-yl)-N-(piperidin-1-yl)-1H-pyrazole-3-carboxamide (Compound 64)

ES-MS (M+1): 665.1.

1-(2,4-Dichlorophenyl)-4-({[(1,1-dioxidothiomorpholin-4-yl)sulfonyl]amino}methyl)-5-[5-(pent-1-yn-1-yl)thiophen-2-yl]-N-(piperidin-1-yl)-1H-pyrazole-3-carboxamide (Compound 65)

ES-MS (M+1): 713.1.

4-(Cyclopentanesulfonamidomethyl)-1-(2,4-dichlorophenyl)-5-(5-(pent-1-ynyl)thiophen-2-yl)-N-(piperidin-1-yl)-1H-pyrazole-3-carboxamide (Compound 66)

ES-MS (M+1): 648.2.

4-((1H-Imidazole-5-sulfonamido)methyl)-1-(2,4-dichlorophenyl)-5-(5-(pent-1-ynyl)thiophen-2-yl)-N-(piperidin-1-yl)-1H-pyrazole-3-carboxamide (Compound 67)

ES-MS (M+1): 646.1.

1-(2,4-Dichlorophenyl)-4-(3-ethylthioureido)methyl)-5-(5-(pent-1-ynyl)thiophen-2-yl)-N-(piperidin-1-yl)-1H-pyrazole-3-carboxamide (Compound 68)

ES-MS (M+1): 603.2.

Methyl(1-(2,4-dichlorophenyl)-5-(5-(pent-1-ynyl)thiophen-2-yl)-3-(piperidin-1-ylcarbamoyl)-1H-pyrazol-4-yl)methylcarbamate (Compound 69)

ES-MS (M+1): 574.1.

4-((3-Cyclopropylureido)methyl)-1-(2,4-dichlorophenyl)-5-(5-(pent-1-ynyl)thiophen-2-yl)-N-(piperidin-1-yl)-1H-pyrazole-3-carboxamide (Compound 70)

ES-MS (M+1): 599.1.

1-(2,4-Dichlorophenyl)-5-(5-(pent-1-ynyl)thiophen-2-yl)-N-(piperidin-1-yl)-4-(propionamidomethyl)-1H-pyrazole-3-carboxamide (Compound 71)

ES-MS (M+1): 572.1.

1-(2,4-Dichlorophenyl)-4-((N,N-dimethylsulfamoylamino)methyl)-5-(5-(pent-1-ynyl)thiophen-2-yl)-N-(piperidin-1-yl)-1H-pyrazole-3-carboxamide (Compound 72)

ES-MS (M+1): 623.1.

1-(2,4-Dichlorophenyl)-4-((N-methylsulfamoylamino)methyl)-5-(5-(pent-1-ynyl)thiophen-2-yl)-N-(piperidin-1-yl)-1H-pyrazole-3-carboxamide (Compound 73)

ES-MS (M+1): 609.1.

5-(5-(Cyclopentylethynyl)thiophen-2-yl)-1-(2,4-dichlorophenyl)-N-(piperidin-1-yl)-4-((pyrrolidine-1-sulfonamido)methyl)-1H-pyrazole-3-carboxamide (Compound 74)

ES-MS (M+1): 675.1.

5-(5-(Cyclopentylethynyl)thiophen-2-yl)-1-(2,4-dichlorophenyl)-N-(piperidin-1-yl)-4-((piperidine-1-sulfonamido)methyl)-1H-pyrazole-3-carboxamide (Compound 75)

ES-MS (M+1): 689.1.

5-(5-(Cyclopentylethynyl)thiophen-2-yl)-1-(2,4-dichlorophenyl)-4-((morpholine-4-sulfonamido)methyl)-N-(piperidin-1-yl)-1H-pyrazole-3-carboxamide (Compound 76)

ES-MS (M+1): 691.1.

5-[5-(Cyclopentylethynyl)thiophen-2-yl]-1-(2,4-dichlorophenyl)-4-({[(1,1-dioxidothiomorpholin-4-yl)sulfonyl]amino}methyl)-N-(piperidin-1-yl)-1H-pyrazole-3-carboxamide (Compound 77)

ES-MS (M+1): 739.1.

4-(Cyclopentanesulfonamidomethyl)-5-(5-(cyclopentylethynyl)thiophen-2-yl)-1-(2,4-dichlorophenyl)-N-(piperidin-1-yl)-1H-pyrazole-3-carboxamide (Compound 78)

ES-MS (M+1): 674.1.

4-((1H-Imidazole-5-sulfonamido)methyl)-5-(5-(cyclopentylethynyl)thiophen-2-yl)-1-(2,4-dichlorophenyl)-N-(piperidin-1-yl)-1H-pyrazole-3-carboxamide (Compound 79)

ES-MS (M+1): 672.1.

5-(5-(Cyclopentylethynyl)thiophen-2-yl)-1-(2,4-dichlorophenyl)-4-((3-ethylthioureido)methyl)-N-(piperidin-1-yl)-1H-pyrazole-3-carboxamide (Compound 80)

ES-MS (M+1): 629.1.

Methyl(5-(5-(cyclopentylethynyl)thiophen-2-yl)-1-(2,4-dichlorophenyl)-3-(piperidin-1-ylcarbamoyl)-1H-pyrazol-4-yl)methylcarbamate (Compound 81)

ES-MS (M+1): 600.1.

5-(5-(Cyclopentylethynyl)thiophen-2-yl)-4-((3-cyclopropylureido)methyl)-1-(2,4-dichlorophenyl)-N-(piperidin-1-yl)-1H-pyrazole-3-carboxamide (Compound 82)

ES-MS (M+1): 625.1.

5-(5-(Cyclopentylethynyl)thiophen-2-yl)-1-(2,4-dichlorophenyl)-N-(piperidin-1-yl)-4-(propionamidomethyl)-1H-pyrazole-3-carboxamide (Compound 83)

ES-MS (M+1): 598.1.

5-(5-(Cyclopentylethynyl)thiophen-2-yl)-1-(2,4-dichlorophenyl)-4-((N,N-dimethylsulfamoylamino)methyl)-N-(piperidin-1-yl)-1H-pyrazole-3-carboxamide (Compound 84)

ES-MS (M+1): 649.1.

5-(5-(Cyclopentylethynyl)thiophen-2-yl)-1-(2,4-dichlorophenyl)-4-((N-methyl sulfamoylamino)methyl)-N-(piperidin-1-yl)-1H-pyrazole-3-carboxamide (Compound 85)

ES-MS (M+1): 635.1.

1-(2,4-dichlorophenyl)-4-((3-hydroxypyrrolidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 143)

ES-MS (M+1): 767.0.

1-(2,4-dichlorophenyl)-4-(((R)-3-hydroxypyrrolidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 144)

ES-MS (M+1): 767.0.

1-(2,4-dichlorophenyl)-4-(((S)-3-hydroxypyrrolidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 145)

ES-MS (M+1): 767.0.

1-(2,4-dichlorophenyl)-4-((3-fluoro-3-methylazetidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 146)

ES-MS (M+1): 772.9.

1-(2,4-dichlorophenyl)-4-((3,3-difluoropyrrolidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 147)

ES-MS (M+1): 786.9.

1-(2,4-dichlorophenyl)-4-(((S)-3-fluoropyrrolidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 148)

ES-MS (M+1): 769.0.

1-(2,4-dichlorophenyl)-4-(((R)-3-fluoropyrrolidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 149)

ES-MS (M+1): 769.0.

1-(2,4-dichlorophenyl)-N-(piperidin-1-yl)-5-(5-((4-(trifluoromethyl)phenyl)ethynyl)thiophen-2-yl)-4-(((S)-2-(trifluoromethyl)pyrrolidine-1-sulfonamido)methyl)-1H-pyrazole-3-carboxamide (compound 150)

ES-MS (M+1): 819.0.

1-(2,4-dichlorophenyl)-N-(piperidin-1-yl)-5-(5-((4-(trifluoromethyl)phenyl)ethynyl)thiophen-2-yl)-4-(((R)-2-(trifluoromethyl)pyrrolidine-1-sulfonamido)methyl)-1H-pyrazole-3-carboxamide (compound 151)

ES-MS (M+1): 819.0.

1-(2,4-dichlorophenyl)-N-(piperidin-1-yl)-5-(5-((4-(trifluoromethyl)phenyl)ethynyl)thiophen-2-yl)-4-((3-(trifluoromethyl)pyrrolidine-1-sulfonamido)methyl)-1H-pyrazole-3-carboxamide (compound 152)

ES-MS (M+1): 819.0.

1-(2,4-dichlorophenyl)-4-((4,4-difluoropiperidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 153)

ES-MS (M+1): 800.9.

1-(2,4-dichlorophenyl)-4-((4,4-dimethylpiperidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 154)

ES-MS (M+1): 793.1.

1-(2,4-dichlorophenyl)-N-(piperidin-1-yl)-5-(5-((4-(trifluoromethyl)phenyl)ethynyl)thiophen-2-yl)-4-(((R)-3-(trifluoromethyl)pyrrolidine-1-sulfonamido)methyl)-1H-pyrazole-3-carboxamide (compound 155)

ES-MS (M+1): 819.0.

1-(2,4-dichlorophenyl)-N-(piperidin-1-yl)-5-(5-((4-(trifluoromethyl)phenyl)ethynyl)thiophen-2-yl)-4-(((S)-3-(trifluoromethyl)pyrrolidine-1-sulfonamido)methyl)-1H-pyrazole-3-carboxamide (compound 156)

ES-MS (M+1): 819.0.

1-(2,4-dichlorophenyl)-4-((4-hydroxypiperidine-1-sulfonamido)methyl)-N-(piperidin-1-yl)-5-(5-((4-(trifluoromethyl)phenyl)ethynyl)thiophen-2-yl)-1H-pyrazole-3-carboxamide (compound 157)

ES-MS (M+1): 781.0

EXAMPLE 2

Synthesis of Compounds 87-113

The general procedure is illustrated immediately below using compound 87 as a specific example.

4-(Bromomethyl)-1-(2,4-dichlorophenyl)-N-(piperidin-1-yl)-5-(5-((4-(trifluoro methyl)phenyl)ethynyl)thiophen-2-yl)-1H-pyrazole-3-carboxamide (Compound 86)

To a magnetically stirred solution of compound 8 (0.15 g, 0.24 mmol) in $CH_2Cl_2$ (5 mL) at 0° C. was added $PBr_3$ (0.13 g, 0.48 mmol) dropwise. The resulting mixture was allowed to warm up to room temperature for 2 h, and then quenched with ice water. The aqueous phase was extracted with $CH_2Cl_2$ (2×10 mL). The combined organic extracts were washed with water and brine, dried over anhydrous sodium sulfate, filtered, and concentrated under reduced pressure to give bromide 86 as a pale yellow solid. $^1$H NMR (CDCl$_3$) δ 7.58 (m, 4H), 7.53-7.52 (m, 1H), 7.38-7.37 (m, 2H), 7.23 (d, J=4.0 Hz, 1H), 7.17 (d, J=4.0 Hz, 1H), 4.92 (s, 2H), 2.85 (brs, 4H), 1.77-1.71 (m, 4H), 1.42 (brs, 2H); ESMS m/z: 681.1 (M+1).

1-(2,4-Dichlorophenyl)-4-[(1,1-dioxidothiomorpholin-4-yl)methyl]-N-(piperidin-1-yl)-5-(5-{[4-(trifluoromethyl)phenyl]ethynyl}thiophen-2-yl)-1H-pyrazole-3-carboxamide (Compound 87)

To a magnetically stirred solution of bromide 86 (0.16 g, 0.24 mmol) in DMF (3 mL) at room temperature was added thiomorpholine 1,1-dioxide (0.07 g, 0.48 mmol) in one portion. The resulting mixture was heated to 60° C. for 16 h, and then quenched with water. The aqueous phase was extracted with ethyl acetate (2×10 mL). The combined organic extracts were washed with water and brine, dried over anhydrous sodium sulfate, filtered, and concentrated under reduced pressure to give crude residue, which was subjected to purification by flash chromatography on silica gel with n-hexane/ethyl acetate (1:1) to afford the desired product 87 (0.14 g, 79% over two steps) as a white solid: $^1$H NMR (CDCl$_3$) δ 7.72 (s, 1H), 7.61 (m, 4H), 7.52 (d, J=1.8 Hz, 1H), 7.41 (d, J=1.8 Hz, 1H), 7.17 (d, J=3.9 Hz, 1H), 6.92 (d, J=3.9 Hz, 1H), 4.03 (s, 2H), 3.14-3.05 (m, 8H), 2.85-2.82 (m, 4H), 1.79-1.74 (m, 4H), 1.44-1.40 (m, 2H); ESMS m/z: 735.8 (M+1).

1-(2,4-Dichlorophenyl)-4-((methylamino)methyl)-N-(piperidin-1-yl)-5-(5-((4-(trifluoromethyl)phenyl)ethynyl)thiophen-2-yl)-1H-pyrazole-3-carboxamide (Compound 88)

ES-MS (M+1): 632.1.

4-((Cyclopropylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 89)

ES-MS (M+1): 658.1.

1-(2,4-Dichlorophenyl)-4-((isopropylamino)methyl)-N-(piperidin-1-yl)-5-(5-((4-(trifluoromethyl)phenyl)ethynyl)thiophen-2-yl)-1H-pyrazole-3-carboxamide (Compound 90)

ES-MS (M+1): 660.1.

1-(2,4-Dichlorophenyl)-4-((3-hydroxyazetidin-1-yl)methyl)-N-(piperidin-1-yl)-5-(5-((4-(trifluoromethyl)phenyl)ethynyl)thiophen-2-yl)-1H-pyrazole-3-carboxamide (Compound 91)

ES-MS (M+1): 674.1.

1-(2,4-Dichlorophenyl)-4-((3-fluoroazetidin-1-yl)methyl)-N-(piperidin-1-yl)-5-(5-((4-(trifluoromethyl)phenyl)ethynyl)thiophen-2-yl)-1H-pyrazole-3-carboxamide (Compound 92)

ES-MS (M+1): 676.1.

1-(2,4-Dichlorophenyl)-4-((oxetan-3-ylamino)methyl)-N-(piperidin-1-yl)-5-(5-((4-(trifluoromethyl)phenyl)ethynyl)thiophen-2-yl)-1H-pyrazole-3-carboxamide (Compound 93)

ES-MS (M+1): 674.1.

1-(2,4-Dichlorophenyl)-4-((3-methyloxetan-3-ylamino)methyl)-N-(piperidin-1-yl)-5-(5-((4-(trifluoromethyl)phenyl)ethynyl)thiophen-2-yl)-1H-pyrazole-3-carboxamide (Compound 94)

ES-MS (M+1): 688.1.

1-(2,4-Dichlorophenyl)-4-((methyl(oxetan-3-yl)amino)methyl)-N-(piperidin-1-yl)-5-(5-((4-(trifluoromethyl)phenyl)ethynyl)thiophen-2-yl)-1H-pyrazole-3-carboxamide (Compound 95)

ES-MS (M+1): 688.1.

1-(2,4-Dichlorophenyl)-4-((oxetan-3-ylmethylamino)methyl)-N-(piperidin-1-yl)-5-(5-((4-(trifluoromethyl)phenyl)ethynyl)thiophen-2-yl)-1H-pyrazole-3-carboxamide (Compound 96)

ES-MS (M+1): 688.1.

1-(2,4-Dichlorophenyl)-N-(piperidin-1-yl)-4-((prop-2-ynylamino)methyl)-5-(5-((4-(trifluoromethyl)phenyl)ethynyl)thiophen-2-yl)-1H-pyrazole-3-carboxamide (Compound 97)

ES-MS (M+1): 656.1.

1-(2,4-Dichlorophenyl)-4-((methyl(prop-2-ynyl)amino)methyl)-N-(piperidin-1-yl)-5-(5-((4-(trifluoromethyl)phenyl)ethynyl)thiophen-2-yl)-1H-pyrazole-3-carboxamide (Compound 98)

ES-MS (M+1): 670.1.

1-(2,4-Dichlorophenyl)-4-(((R)-2-hydroxypropylamino)methyl)-N-(piperidin-1-yl)-5-(5-((4-(trifluoromethyl)phenyl)ethynyl)thiophen-2-yl)-1H-pyrazole-3-carboxamide (Compound 99)

ES-MS (M+1): 676.1.

1-(2,4-Dichlorophenyl)-4-(((S)-3-hydroxypyrrolidin-1-yl)methyl)-N-(piperidin-1-yl)-5-(5-((4-(trifluoromethyl)phenyl)ethynyl)thiophen-2-yl)-1H-pyrazole-3-carboxamide (Compound 100)

ES-MS (M+1): 688.1.

1-(2,4-Dichlorophenyl)-4-(((S)-2-(hydroxymethyl)pyrrolidin-1-yl)methyl)-N-(piperidin-1-yl)-5-(5-((4-(trifluoromethyl)phenyl)ethynyl)thiophen-2-yl)-1H-pyrazole-3-carboxamide (Compound 101)

ES-MS (M+1): 702.1.

1-(2,4-Dichlorophenyl)-4-(((R)-2-(hydroxymethyl)pyrrolidin-1-yl)methyl)-N-(piperidin-1-yl)-5-(5-((4-(trifluoromethyl)phenyl)ethynyl)thiophen-2-yl)-1H-pyrazole-3-carboxamide (Compound 102)

ES-MS (M+1): 702.1.

4-(((R)-2-Cyanopyrrolidin-1-yl)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 103)

ES-MS (M+1): 697.1.

1-(2,4-Dichlorophenyl)-4-[(1,1-difluoro-5-azaspiro[2.4]hept-5-yl)methyl]-N-(piperidin-1-yl)-5-(5-{[4-(trifluoromethyl)phenyl]ethynyl}thiophen-2-yl)-1H-pyrazole-3-carboxamide (Compound 104)

ES-MS (M+1): 734.1.

1-(2,4-Dichlorophenyl)-4-((6,6-difluoro-3-aza-bicyclo[3.1.0]hexan-3-yl)methyl)-N-(piperidin-1-yl)-5-(5-((4-(trifluoromethyl)phenyl)ethynyl)thiophen-2-yl)-1H-pyrazole-3-carboxamide (Compound 105)

ES-MS (M+1): 720.2.

1-(2,4-Dichlorophenyl)-4-((3,3-difluoropyrrolidin-1-yl)methyl)-N-(piperidin-1-yl)-5-(5-((4-(trifluoromethyl)phenyl)ethynyl)thiophen-2-yl)-1H-pyrazole-3-carboxamide (Compound 106)

ES-MS (M+1): 708.1.

1-(2,4-Dichlorophenyl)-N-(piperidin-1-yl)-5-(5-((4-(trifluoromethyl)phenyl)ethynyl)thiophen-2-yl)-4-(3-(trifluoromethyl)pyrrolidin-1-yl)methyl)-1H-pyrazole-3-carboxamide (Compound 107)

ES-MS (M+1): 740.1.

4-((1-Cyanocyclopropylamino)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 108)

ES-MS (M+1): 683.1.

1-(2,4-Dichlorophenyl)-4-(piperazin-1-ylmethyl)-N-(piperidin-1-yl)-5-(5-((4-(trifluoromethyl)phenyl)ethynyl)thiophen-2-yl)-1H-pyrazole-3-carboxamide (Compound 109)

ES-MS (M+1): 687.1.

1-(2,4-Dichlorophenyl)-4-((4-methylpiperazin-1-yl)methyl)-N-(piperidin-1-yl)-5-(5-((4-(trifluoromethyl)phenyl)ethynyl)thiophen-2-yl)-1H-pyrazole-3-carboxamide (Compound 110)

ES-MS (M+1): 701.1.

4-((1H-1,2,4-Triazol-1-yl)methyl)-1-(2,4-dichlorophenyl)-N-(piperidin-1-yl)-5-(5-((4-(trifluoromethyl)phenyl)ethynyl)thiophen-2-yl)-1H-pyrazole-3-carboxamide (Compound 111)

ES-MS (M+1): 670.1.

4-(Azidomethyl)-1-(2,4-dichlorophenyl)-N-(piperidin-1-yl)-5-(5-((4-(trifluoro methyl)phenyl)ethynyl)thiophen-2-yl)-1H-pyrazole-3-carboxamide (Compound 112)

ES-MS (M+1): 644.2.

4-(Cyanomethyl)-1-(2,4-dichlorophenyl)-N-(piperidin-1-yl)-5-(5-((4-(trifluoro methyl)phenyl)ethynyl)thiophen-2-yl)-1H-pyrazole-3-carboxamide (Compound 113)

ES-MS (M+1): 628.1.

EXAMPLE 3

Synthesis of Compounds 119-142

Compounds 119-142 were prepared according to a general synthetic method illustrated below using Compound 119 as an example.

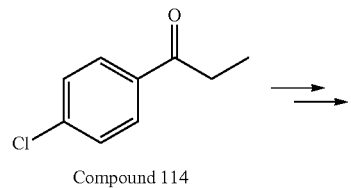
Compound 114

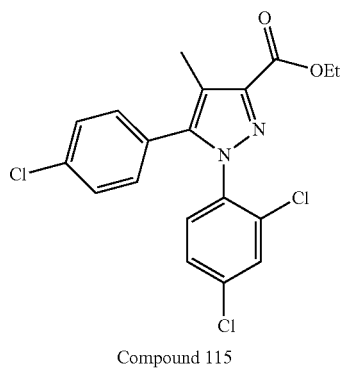
Compound 115

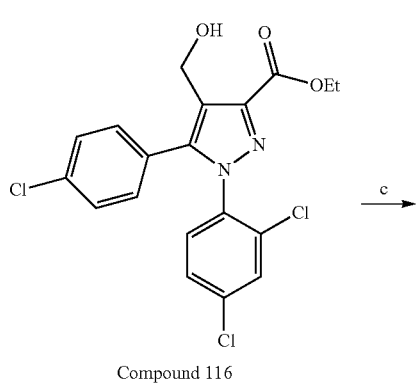
Compound 116

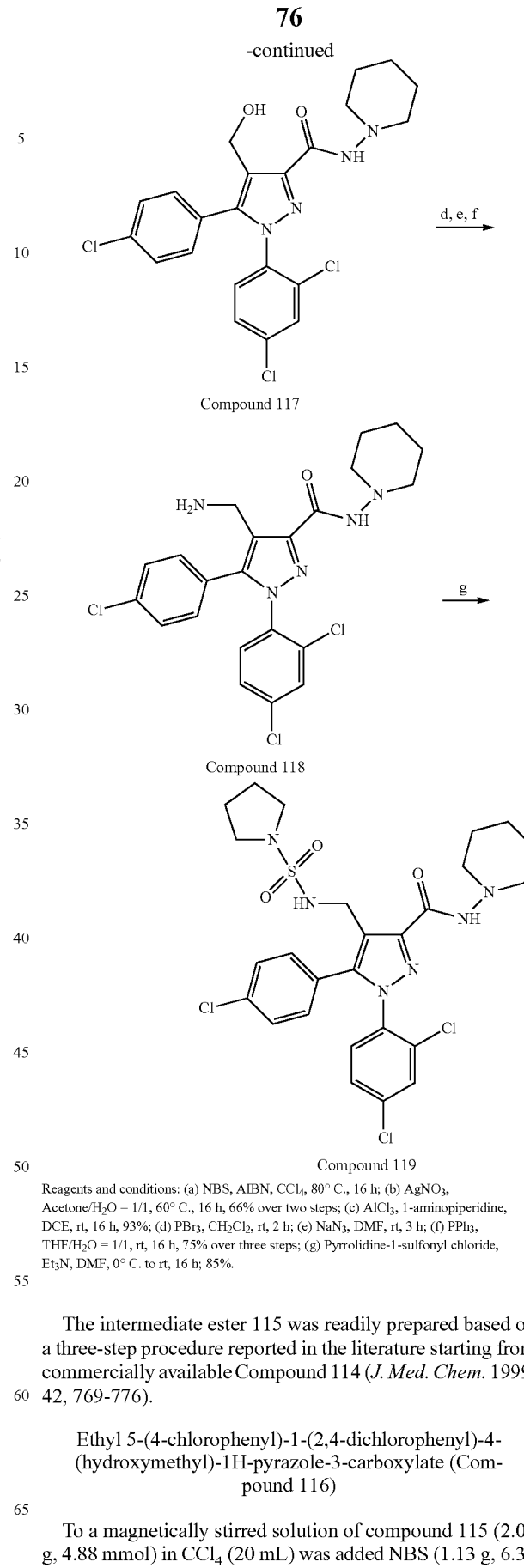

Reagents and conditions: (a) NBS, AIBN, CCl₄, 80° C., 16 h; (b) AgNO₃, Acetone/H₂O = 1/1, 60° C., 16 h, 66% over two steps; (c) AlCl₃, 1-aminopiperidine, DCE, rt, 16 h, 93%; (d) PBr₃, CH₂Cl₂, rt, 2 h; (e) NaN₃, DMF, rt, 3 h; (f) PPh₃, THF/H₂O = 1/1, rt, 16 h, 75% over three steps; (g) Pyrrolidine-1-sulfonyl chloride, Et₃N, DMF, 0° C. to rt, 16 h; 85%.

The intermediate ester 115 was readily prepared based on a three-step procedure reported in the literature starting from commercially available Compound 114 (*J. Med. Chem.* 1999, 42, 769-776).

Ethyl 5-(4-chlorophenyl)-1-(2,4-dichlorophenyl)-4-(hydroxymethyl)-1H-pyrazole-3-carboxylate (Compound 116)

To a magnetically stirred solution of compound 115 (2.00 g, 4.88 mmol) in CCl₄ (20 mL) was added NBS (1.13 g, 6.34 mmol) and AIBN (0.06 g, 0.39 mmol). The resulting mixture was refluxed for 16 h. After cooling to room temperature, the precipitate was filtered. The solvent was removed from the filtrate under reduced pressure to give crude bromide as a pale yellow liquid. To a magnetically stirred solution of silver nitrate (3.32 g, 19.52 mmol) in 100 mL of 50% aqueous acetone at room temperature was added a suspension of bromide in 70% aqueous acetone. The mixture was stirred at 60° C. overnight. After cooling to room temperature, the insoluble residue was filtered off and the resulting filtrate was concentrated under vacuum to remove acetone. The mixture was extracted with $CH_2Cl_2$, and the combined organic layer was washed with water, dried over anhydrous magnesium sulfate, filtered and concentrated to give crude residue, which was subjected to purification by flash chromatography on silica gel with n-hexane/ethyl acetate (1:1) to afford ester 116 (1.37 g, 66% over two steps) as a white solid: $^1$H NMR ($CDCl_3$) δ 7.41 (d, J=1.8 Hz, 1H), 7.34-7.27 (m, 4H), 7.13-7.10 (m, 2H), 4.63 (d, J=6.9 Hz, 2H), 4.60 (q, J=6.9 Hz, 2H), 3.84 (t, J=7.2 Hz, 1H), 1.45 (t, J=6.9 Hz, 3H); ESMS m/z: 447.0 (M+1).

5-(4-Chlorophenyl)-1-(2,4-dichlorophenyl)-4-(hydroxymethyl)-N-(piperidin-1-yl)-1H-pyrazole-3-carboxamide (Compound 117)

To a magnetically stirred solution of 116 (1.21 g, 2.84 mmol) and aluminum trichloride (1.52 g, 11.36 mmol) in dichloride ethane (20 mL) was added 1-amino piperidine (1.14 g, 11.36 mmol) slowly under argon at 0° C. The resulting mixture was allowed to warm up to room temperature for 16 h, and then quenched with ice water and the aqueous phase was extracted with $CH_2Cl_2$ (2×20 mL). The combined organic extracts were washed with water and brine, dried over anhydrous sodium sulfate, filtered, and concentrated under reduced pressure to give crude residue, which was subjected to purification by flash chromatography on silica gel with n-hexane/ethyl acetate (1:1) to afford compound 117 (1.27 g, 93%) as a white solid: $^1$H NMR ($CDCl_3$) δ 7.78 (brs, 1H), 7.44 (d, J=2.4 Hz, 1H), 7.33-7.20 (m, 4H), 7.08-7.03 (m, 2H), 5.16 (t, J=6.9 Hz, 1H), 4.60 (d, J=6.9 Hz, 2H), 2.88-2.80 (m, 4H), 1.78 (quintet, J=5.4 Hz, 4H), 1.50-1.40 (m, 2H); ESMS m/z: 479.0 (M+1).

4-(Aminomethyl)-5-(4-chlorophenyl)-1-(2,4-dichlorophenyl)-N-(piperidin-1-yl)-1H-pyrazole-3-carboxamide (Compound 118)

To a magnetically stirred solution of 117 (0.34 g, 0.72 mmol) in $CH_2Cl_2$ (20 mL) at 0° C. was added $PBr_3$ (0.39 g, 1.43 mmol) dropwise. The resulting mixture was allowed to warm up to room temperature for 2 h, and then quenched with water. The aqueous phase was extracted with $CH_2Cl_2$ (2×10 mL). The combined organic extracts were washed with water and brine, dried over anhydrous sodium sulfate, filtered, and concentrated under reduced pressure to give the corresponding bromide as a pale yellow solid. Without purification, the bromo compound thus obtained was treated with $NaN_3$ (0.23 g, 3.58 mmol) in DMF (5 mL) at room temperature for 3 h. The reaction mixture was poured into water (10 mL) and the aqueous layer was extracted with ethyl acetate (2×20 mL). The combined organic extracts were washed with water and brine, dried over anhydrous sodium sulfate, filtered, and concentrated under reduced pressure to yield the crude azide which without purification was further treated with $PPh_3$ (0.38 g, 1.43 mmol) in $THF/H_2O$ (1/1) (7 mL) at room temperature for 16 h. The reaction mixture was extracted with ethyl acetate (2×20 mL). The combined organic extracts were washed with water and brine, dried over anhydrous sodium sulfate, filtered, and concentrated under reduced pressure to afford crude residue, which was subjected to purification by flash chromatography on silica gel with $CH_2Cl_2$/MeOH (9:1) to afford compound 118 (0.26 g, 75% over three steps) as a white solid: $^1$H NMR ($CDCl_3$) δ 7.84 (brs, 1H), 7.44 (d, J=1.8 Hz, 1H), 7.30 (d, J=8.1 Hz, 2H), 7.28-7.24 (m, 2H), 7.14 (d, J=8.1 Hz, 2H), 3.87 (s, 2H), 2.88-2.80 (m, 4H), 1.83 (brs, 1H), 1.83-1.71 (m, 4H), 1.48-1.38 (m, 2H); ESMS m/z: 478.0 (M+1).

5-(4-Chlorophenyl)-1-(2,4-dichlorophenyl)-N-(piperidin-1-yl)-4-((pyrrolidine-1-sulfonamido)methyl)-1H-pyrazole-3-carboxamide (Compound 119)

To a magnetically stirred solution of 118 (0.26 g, 0.54 mmol) and $Et_3N$ (0.11 g, 1.08 mmol) in DMF (3 mL) at 0° C. was added pyrrolidine-1-sulfonyl chloride (0.14 g, 0.81 mmol) dropwise. The resulting mixture was allowed to warm up to room temperature for 16 h, and then quenched with water. The aqueous phase was extracted with ethyl acetate (2×10 mL), and the combined organic extracts were washed with water and brine, dried over anhydrous sodium sulfate, filtered, and concentrated under reduced pressure to give crude residue, which was purified by flash chromatography with n-hexane/ethyl acetate (1:1) to afford the desired product 119 (0.28 g, 85%) as a white solid: $^1$H NMR ($CDCl_3$) δ 7.72 (s, 1H), 7.45 (d, J=2.0 Hz, 1H), 7.34-7.29 (m, 3H), 7.24-7.19 (m, 3H), 6.52 (t, J=6.8 Hz, 1H), 4.19 (d, J=6.8 Hz, 2H), 3.26-3.22 (m, 4H), 2.88-2.80 (m, 4H), 1.85 (quintet, J=3.6 Hz, 4H), 1.78 (quintet, J=5.6 Hz, 4H), 1.48-1.41 (m, 2H); ESMS m/z: 611.1 (M+1).

5-(4-Chlorophenyl)-1-(2,4-dichlorophenyl)-N-(piperidin-1-yl)-4-((piperidine-1-sulfonamido)methyl)-1H-pyrazole-3-carboxamide (Compound 120)

ES-MS (M+1): 627.1.

5-(4-Chlorophenyl)-1-(2,4-dichlorophenyl)-4-((morpholine-4-sulfonamido) methyl)-N-(piperidin-1-yl)-1H-pyrazole-3-carboxamide (Compound 121)

ES-MS (M+1): 629.1.

5-(4-Chlorophenyl)-1-(2,4-dichlorophenyl)-4-({[(1,1-dioxidothiomorpholin-4-yl) sulfonyl]amino}methyl)-N-(piperidin-1-yl)-1H-pyrazole-3-carboxamide (Compound 122)

ES-MS (M+1): 677.1.

5-(4-Chlorophenyl)-4-(cyclopentanesulfonamidomethyl)-1-(2,4-dichlorophenyl)-N-(piperidin-1-yl)-1H-pyrazole-3-carboxamide (Compound 123)

ES-MS (M+1): 612.1.

4-((1H-Imidazole-5-sulfonamido)methyl)-5-(4-chlorophenyl)-1-(2,4-dichloro phenyl)-N-(piperidin-1-yl)-1H-pyrazole-3-carboxamide (Compound 124)

ES-MS (M+1): 610.1.

5-(4-Chlorophenyl)-1-(2,4-dichlorophenyl)-4-((3-ethylthioureido)methyl)-N-(piperidin-1-yl)-1H-pyrazole-3-carboxamide (Compound 125)

ES-MS (M+1): 567.1.

Methyl(5-(4-chlorophenyl)-1-(2,4-dichlorophenyl)-3-(piperidin-1-ylcarbamoyl)-1H-pyrazol-4-yl)methylcarbamate (Compound 126)

ES-MS (M+1): 536.1.

5-(4-Chlorophenyl)-4-((3-cyclopropylureido)methyl)-1-(2,4-dichlorophenyl)-N-(piperidin-1-yl)-1H-pyrazole-3-carboxamide (Compound 127)

ES-MS (M+1): 561.1.

5-(4-Chlorophenyl)-1-(2,4-dichlorophenyl)-N-(piperidin-1-yl)-4-(propionamido methyl)-1H-pyrazole-3-carboxamide (Compound 128)

ES-MS (M+1): 534.1.

5-(4-Chlorophenyl)-1-(2,4-dichlorophenyl)-4-((N,N-dimethylsulfamoylamino) methyl)-N-(piperidin-1-yl)-1H-pyrazole-3-carboxamide (Compound 129)

ES-MS (M+1): 587.1.

5-(4-Chlorophenyl)-1-(2,4-dichlorophenyl)-4-((N-methylsulfamoylamino) methyl)-N-(piperidin-1-yl)-1H-pyrazole-3-carboxamide (Compound 130)

ES-MS (M+1): 573.1.

5-(4-Chlorophenyl)-1-(2,4-dichlorophenyl)-4-((4,5-dihydro-1H-imidazol-2-ylamino)methyl)-N-(piperidin-1-yl)-1H-pyrazole-3-carboxamide (Compound 131)

ES-MS (M+1): 546.1.

5-(4-Chlorophenyl)-1-(2,4-dichlorophenyl)-4-((2,6-dimethylmorpholine-4-sulfonamido)methyl)-N-(piperidin-1-yl)-1H-pyrazole-3-carboxamide (Compound 132)

ES-MS (M+1): 655.1.

5-(4-Chlorophenyl)-4-((N-cyclopentylsulfamoylamino)methyl)-1-(2,4-dichlorophenyl)-N-(piperidin-1-yl)-1H-pyrazole-3-carboxamide (Compound 133)

ES-MS (M+1): 625.1.

1-(2,4-Dichlorophenyl)-N-(piperidin-1-yl)-4-((pyrrolidine-1-sulfonamido) methyl)-5-(4-(trifluoromethyl)phenyl)-1H-pyrazole-3-carboxamide (Compound 134)

ES-MS (M+1): 645.1.

1-(2,4-Dichlorophenyl)-N-(piperidin-1-yl)-4-((piperidine-1-sulfonamido)methyl)-5-(4-(trifluoromethyl)phenyl)-1H-pyrazole-3-carboxamide (Compound 135)

ES-MS (M+1): 659.2.

1-(2,4-Dichlorophenyl)-4-((morpholine-4-sulfonamido)methyl)-N-(piperidin-1-yl)-5-(4-(trifluoromethyl)phenyl)-1H-pyrazole-3-carboxamide (Compound 136)

ES-MS (M+1): 661.1.

1-(2,4-Dichlorophenyl)-4-({[(1,1-dioxidothiomorpholin-4-yl)sulfonyl]amino}methyl)-N-(piperidin-1-yl)-5-[4-(trifluoromethyl)phenyl]-1H-pyrazole-3-carboxamide (Compound 137)

ES-MS (M+1): 709.1.

4-(Cyclopentanesulfonamidomethyl)-1-(2,4-dichlorophenyl)-N-(piperidin-1-yl)-5-(4-(trifluoromethyl)phenyl)-1H-pyrazole-3-carboxamide (Compound 138)

ES-MS (M+1): 644.1.

4-((1H-Imidazole-5-sulfonamido)methyl)-1-(2,4-dichlorophenyl)-N-(piperidin-1-yl)-5-(4-(trifluoromethyl)phenyl)-1H-pyrazole-3-carboxamide (Compound 139)

ES-MS (M+1): 642.1.

1-(2,4-Dichlorophenyl)-4-((4,5-dihydro-1H-imidazol-2-ylamino)methyl)-N-(piperidin-1-yl)-5-(4-(trifluoromethyl)phenyl)-1H-pyrazole-3-carboxamide (Compound 140)

ES-MS (M+1): 580.1.

Methyl(1-(2,4-dichlorophenyl)-3-(piperidin-1-ylcarbamoyl)-5-(4-(trifluoro methyl)phenyl)-1H-pyrazol-4-yl)methylcarbamate (Compound 141)

ES-MS (M+1): 570.1.

4-((N-Cyclopentylsulfamoylamino)methyl)-1-(2,4-dichlorophenyl)-N-(piperidin-1-yl)-5-(4-(trifluoromethyl)phenyl)-1H-pyrazole-3-carboxamide (Compound 142)

ES-MS (M+1): 659.2.

EXAMPLE 4

Radioligand Binding Assay

Human CB1 and CB2 receptors were obtained from HEK293 cell lines stably expressing CB1 and CB2 receptors. Briefly, cells expressing a CB1 or CB2 receptor were harvested and subjected to sonication. The lyzed cells were centrifuged for 30 minutes at 43,000×g at 4° C. The resultant pellets were re-suspended in a buffer (50 mM Tris, 5 mM $MgCl_2$, 2.5 mM EDTA, pH 7.4, 10% sucrose) and stored at −80° C. The protein concentration of the purified membrane was determined by the Bradford method as described in the manual provided by Bio-Rad Laboratories, Inc. (Hercules, Calif.).

The affinity of towards CB1 and CB2 receptor was determined by an in vitro radioligand binding assay as follows. 0.2-8 µg of membrane fractions prepared from CB1 or CB2-expressing cell lines described above were mixed with a buffer (pH 7.4, 50 mM Tris-HCl, 5 mM $MgCl_2$, 1 mM EDTA, and 0.3% BSA) containing 0.75 nM [$^3$H]CP55,940 (a ligand that specifically binds to CB1 and CB2 receptors) and a test compound. Non-radioactive CP 55,940 (1 µM) was used instead of the test compound in a control assay. The mixture was incubated for 1.5 hours at 30° C. in Multiscreen microplates (Millipore, Billerica, Mass.) to allow the test compound or [$^3$H]CP55,940 to bind to the receptor. The binding reaction was terminated by Manifold filtration, in which the membrane fractions (containing a CB1 or CB2 receptor) were retained on the filters. The filters were then washed with an ice-cold wash buffer (50 mM Tris, pH 7.4, 0.25% BSA) four times to remove free [$^3$H]CP55,940. The radioactivity of the membrane fractions bound to the filters was measured by Topcount (Perkin Elmer Inc.). $IC_{50}$ (the concentration of the test compound required to inhibit 50% of the binding of [$^3$H]CP55,940 to the receptor) were calculated.

Compounds 10-85, 87-113, and 119-157 were tested in this assay. It was unexpected that all of the test compounds have $IC_{50}$ values between 1 nM and 10 •M for inhibiting binding of [$^3$H]CP55,940 towards CB1 and CB2 receptors, respectively.

EXAMPLE 5

DELFIA GTP-Binding Assay

The activity of a test compound in modulating CB1 receptor was determined by the method described in the following paragraph using the DELFIA GTP-binding kit supplied by PerkinElmer Inc. (Boston, Mass.). The DELFIA GTP-binding assay is a time-resolved fluorometric assay based on GDP-GTP exchange on G-protein subunits after activation of a G protein-coupled receptor. Note that stimulation of a CB1 receptor by CP 55,940 resulted in replacement of GDP by GTP on the •-subunit of G-protein, leading to GTP-G • • complex, i.e., the activated form of G-protein. Eu-GTP, a non-hydrolysable GTP labeled with the Europium chelate, was used to monitor agonist-dependent activation of G-protein. See Peltonen et al., Eur. J. Pharmacol. 1998, 355, 275.

Plasma membrane derived from HEK293 cells expressing human CB1 receptor was suspended in an assay buffer (50 mM HEPES, pH 7.4, 100 mM NaCl, 100 µg/mL saponin, 5 mM $MgCl_2$, 2 µM GDP, 0.5% BSA). An aliquot of the membrane was added to each well of AcroPlate (Pall Life Sciences, Ann Arbor, Mich.), together with a test compound (various concentrations in 0.1% DMSO) and CP55,940 (20 nM in the assay buffer). The assay plate was incubated in dark at 30° C. for 60 minutes. Eu-GTP was then added to each well and the plate was incubated for another 30 minutes at 30° C. in dark. The plate was washed four times with a wash solution provided in the assay kit. Binding of Eu-GTP was detected based on the fluorescence signal determined by a Victor 2 multi-label reader. The $EC_{50}$ value (i.e., 50% inhibition of CP55,940-stimulated Eu-GTP binding) for each test compound was determined by a concentration-response curve using nonlinear regression (Prism; GraphPad, San Diego, Calif.).

Compounds 10-85, 87-113, and 119-157 were tested in this assay. Unexpectedly, all of the test compounds have $EC_{50}$ values between 1 nM and 10 µM for inhibiting Eu-GTP binding by modulating CP55,940-stimulated CB1 receptor activation.

EXAMPLE 6

Tetrad Response Test

Body temperature and tail-flick responses were measured by rectal thermometer (Natsume, Japan) and tail-flick analgesia meter RS232 (Columbus, USA), respectively, in male C57BL/6 mice. One hour after oral administration of a test compound dissolved in DMSO/Tween 80/$H_2O$ (1/1/8 by volume), 1 mg/kg of CP55,940 in saline containing 0.5% DMSO was injected intraperitoneally. Body temperature was measured at a time point of 30 and 65 min, and tail flick response was measured at a time point of 35 min after the injection.

Multiple compounds were tested. It was unexpected that, Compounds 10, 63, and 119, did not reverse or slightly reversed both CB1 agonist-induced hypothermia and analgesic responses at an oral dose up to 100 mg/kg in the mice. Conversely, these responses were significantly reversed by rimonabant, a typical central CB1 antagonist, at a dose as low as 2 mg/kg.

EXAMPLE 7

Treatment of Diet-Induced Obese Mice with Test Compounds

Six-week-old C57BL/6 mice were given high-fat diet (Research Diet D 12451; 45% fat, 20% protein, and 35% carbohydrate) for more than 12 weeks before treated with a test compound. Mice weight matched were assigned to different groups and orally gavaged once daily with a vehicle (10% DMSO/10% Tween 80/80% $H_2O$) or a test compound at a defined dosage (e.g., 10 and 20 mg/kg) for at least two weeks. The sum of food taken for each treatment and the body weight were measured daily.

Multiple compounds were tested. Unexpectedly, chronic treatment of diet-induced obese mice with Compound 10 for 21 days led to a relative weight-loss rate of 26.4% (vs 29.1% with rimonabant) and 32.8% for 10 and 20 mg/kg groups, respectively.

EXAMPLE 8

Insulin Sensitivity in db/db Mice

Six-week-old male db/db mice were treated with a test compound at a defined dosage (e.g., 10 or 20 mg/kg) for at least two weeks. The sum of food taken for each treatment and the body weight were measured daily. Mice after treatment were fasted overnight and then injected with glucose (2 g/kg, oral gavage). Glucose levels were measured by a glucometer at 0, 30, 60, 90, and 120 minutes. Blood and urine samples and tissues (e.g., kidney) were collected at the conclusion of the study. After treatment, insulin sensitivity of the mice was significantly improved.

EXAMPLE 9

Treatment of Estrogen Deficiency-Induced Osteoporosis Mice

Three-month-old female mice were subjected to bilateral ovariectomy or sham operation. Two weeks postoperatively, a CB1 antagonist (i.e., compounds 10, 63, and 119) or vehicle was administered 5 days per week for 2, 4, and 8 weeks. Bone mineral density and bone mineral contents in femurs, tibiae, and L1-L5 spine were measured by dual energy x-ray absorptiometry. Trabecular bone microstructure (i.e., trabecular bone volume, thickness, number, separation, porosity, and bone volume index) in femurs, tibiae and spine were analyzed by μCT scanning Mechanical strength of the bones was detected by a material test machine. The results showed both increase of bone mineral density and improvement on microstructure.

EXAMPLE 10

Treating Mice Having Osteoarthritis

Four-month-old male Sprague-Dawley rats were anesthetized using intramuscular atropine (1 mg/kg) and intraperitoneal pentobarbital. The left knees of rats underwent medial parapatellar arthrotomy and transection of the anterior cruciate ligament (ACLT) to induce knee osteoarthritis. The osteoarthritic rats were given a CB1 antagonist (i.e., compounds 10, 63, and 119) or vehicle for 8 weeks. Knee joint radiography was evaluated by a mammography system. Gait profiles of joints in osteoarthritic rats were analyzed by a CatWalk system. Joint morphology was histologically evaluated by a Mankin scoring system. The results showed reduction of the Mankin score.

EXAMPLE 11

Treating Rats Having Nephropathy and Kidney Fibrosis

Three-month-old male Wistar rats were given intraperitoneal streptozotocin (50 mg/kg) to induce diabetes. Two weeks later, diabetic rats that had fasting blood glucose levels of 200-300 mg/mL were selected for studies. Caged in a metabolic cage system, the diabetic rats were administered a CB1 antagonist (i.e., compounds 10, 63, and 119) for 4 weeks while their urine was collected. To evaluate renal function, protein and creatinine levels in urine were measured by ELISA. To evaluate renal fibrosis, kidneys were dissected, fixed, paraffin wax embedded, and sectioned for histologic assessment after periodic acid-Schiff staining. The results showed both decrease of urine albumin level and reduction of kidney fibrosis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

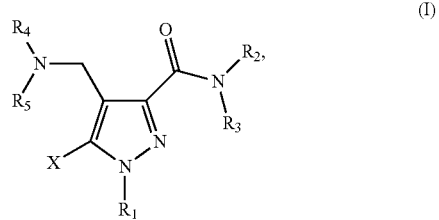

wherein
$R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl;
$R_2$ is H, $C_1$-$C_{10}$ alkyl, $C_3$-$C_{20}$ cycloalkyl, $C_3$-$C_{20}$ heterocycloalkyl, aryl, or heteroaryl;
$R_3$ is $C_3$-$C_{20}$ heterocycloalkyl, aryl, or heteroaryl; or $R_3$, together with $R_2$ and the nitrogen atom to which they are attached, is $C_3$-$C_{20}$ heterocycloalkyl, $C_3$-$C_{20}$ heterocyclo-alkenyl, or heteroaryl;
$R_4$ is H, $C_1$-$C_{10}$ alkyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, heteroaryl, C(O)$R_a$, C(O)O$R_a$, C(O)NR$_a$R$_b$, C(S)NR$_a$R$_b$, C(=NH)NR$_a$R$_b$, C(=N—CN)NR$_a$R$_b$, C(=N—NO$_2$)NR$_a$R$_b$, S(O)$R_a$, S(O$_2$)$R_a$, S(O)NR$_a$R$_b$, or S(O$_2$)NR$_a$R$_b$;
$R_5$ is C(O)$R_a$, C(O)O$R_a$, C(O)NR$_a$R$_b$, C(S)NR$_a$R$_b$, C(=NH)NR$_a$R$_b$, C(=N—CN)NR$_a$R$_b$, C(=N—NO$_2$)NR$_a$R$_b$, S(O)$R_a$, S(O$_2$)$R_a$, S(O)NR$_a$R$_b$, or S(O$_2$)NR$_a$R$_b$; in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl; or $R_a$, together with $R_b$ and the nitrogen atom to which they are attached, is $C_3$-$C_{20}$ heterocycloalkyl, $C_3$-$C_{20}$ heterocycloalkenyl, or heteroaryl; and
X is

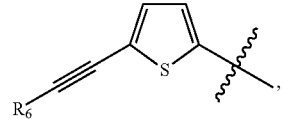

in which $R_6$ is H, $C_1$-$C_{10}$ alkyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, aryl, or heteroaryl.

2. The compound of claim 1, wherein $R_1$ is aryl substituted with halo.

3. The compound of claim 2, wherein $R_1$ is 2,4-dichlorophenyl.

4. The compound of claim 1, wherein $R_2$ is H and $R_3$-is piperidinyl.

5. The compound of claim 1, wherein $R_4$ is H; and $R_5$ is S(O$_2$)NR$_a$R$_b$, in which each of $R_a$ and $R_b$, independently, is H, $C_1$-$C_{10}$ alkyl, $C_3$-$C_{20}$ cycloalkyl, $C_3$-$C_{20}$ heterocycloalkyl, aryl, or heteroaryl; or $R_a$, together with $R_b$ and the nitrogen atom to which they are attached, is $C_3$-$C_{20}$ heterocycloalkyl, $C_3$-$C_{20}$ heterocycloalkenyl, or heteroaryl.

6. The compound of claim 1, wherein $R_a$, together with $R_b$ and the nitrogen atom to which they are attached, is $C_3$-$C_{20}$ heterocycloalkyl, $C_3$-$C_{20}$ heterocycloalkenyl, or heteroaryl.

7. The compound of claim 1, wherein $R_6$ is $C_1$-$C_{10}$ alkyl, $C_3$-$C_{20}$ cycloalkyl, or aryl.

8. The compound of claim 1, wherein the compound is

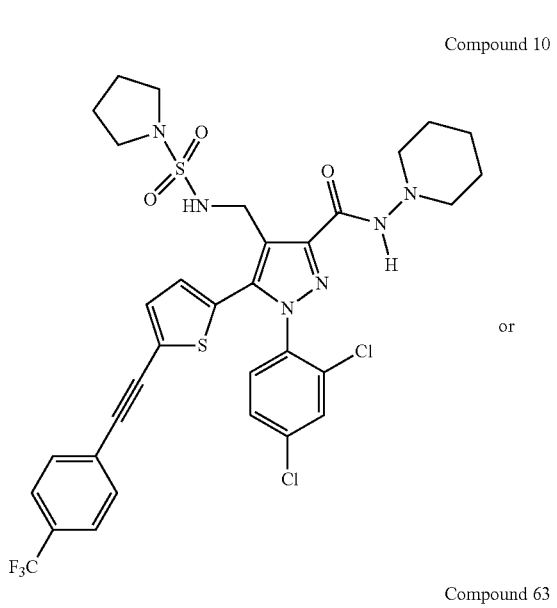

Compound 10 or

Compound 63

9. A method for treating a peripheral cannabinoid 1 receptor mediated disorder, wherein the peripheral cannabinoid 1 receptor mediated disorder is obesity, comprising administering to a subject in need thereof an effective amount of a compound of claim 1.

10. The method of claim 9, wherein the compound is Compound 10 or Compound 63:

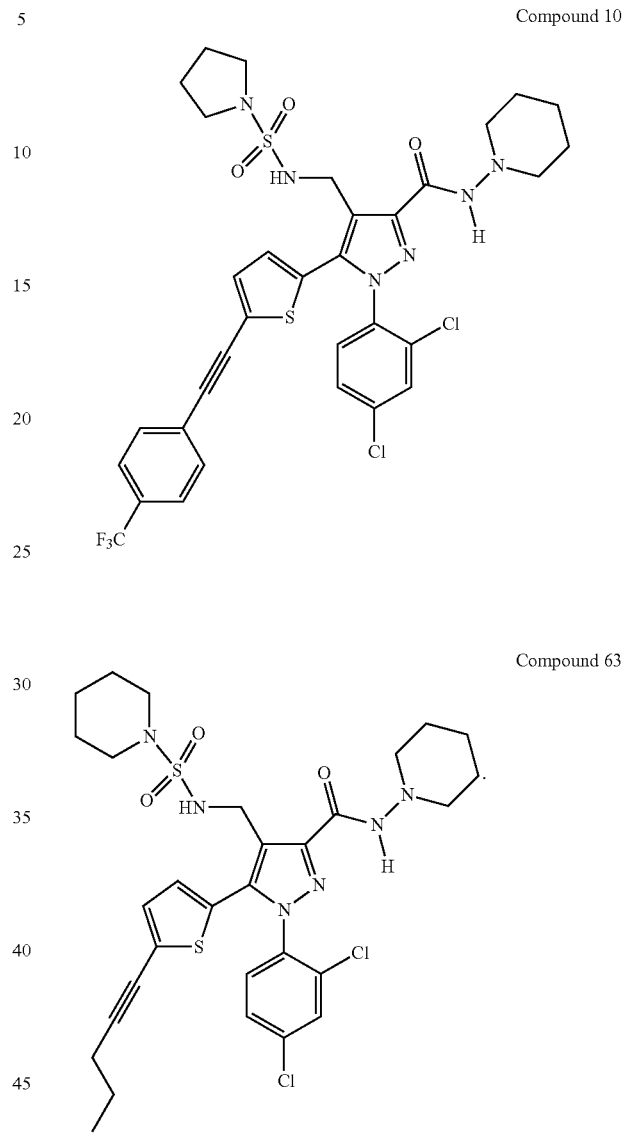

Compound 10

Compound 63

11. A pharmaceutical composition, comprising a pharmaceutically acceptable carrier and a compound of claim 1.

* * * * *